United States Patent
Ren et al.

(10) Patent No.: US 11,612,609 B2
(45) Date of Patent: *Mar. 28, 2023

(54) USES OF OXYGENATED CHOLESTEROL SULFATES (OCS)

(71) Applicants: Virginia Commonwealth University, Richmond, VA (US); Durect Corporation, Cupertino, CA (US)

(72) Inventors: Shunlin Ren, Richmond, VA (US); Felix Theeuwes, Los Altos Hills, CA (US); James E. Brown, Los Gatos, CA (US); WeiQi Lin, Emerald Hills, CA (US)

(73) Assignees: Durect Corporation, Cupertino, CA (US); Virginia Commonwealth University, Richmond, VA (US)

( * ) Notice: Subject to any disclaimer, the term of this patent is extended or adjusted under 35 U.S.C. 154(b) by 10 days.

This patent is subject to a terminal disclaimer.

(21) Appl. No.: 16/983,492

(22) Filed: Aug. 3, 2020

(65) Prior Publication Data
US 2021/0046091 A1   Feb. 18, 2021

Related U.S. Application Data

(63) Continuation of application No. 16/368,553, filed on Mar. 28, 2019, now Pat. No. 10,786,517, which is a
(Continued)

(51) Int. Cl.
*A61K 31/56* (2006.01)
*A61K 31/575* (2006.01)
(Continued)

(52) U.S. Cl.
CPC .......... *A61K 31/575* (2013.01); *A01N 1/0226* (2013.01); *A61K 31/568* (2013.01); *A61K 35/12* (2013.01); *A61P 13/12* (2018.01)

(58) Field of Classification Search
CPC ................ A61K 31/575; A61P 1/16
(Continued)

(56) References Cited

U.S. PATENT DOCUMENTS

| | | | |
|---|---|---|---|
| 3,822,254 | A | 7/1974 | Partridge et al. |
| 3,836,527 | A | 9/1974 | Irmscher et al. |

(Continued)

FOREIGN PATENT DOCUMENTS

| | | |
|---|---|---|
| CN | 1357003 | 7/2002 |
| EP | 0857173 | 11/2003 |

(Continued)

OTHER PUBLICATIONS

Abildayeva et al., "24(S)-Hydroxycholesterol Participates in a Liver X Receptor-controlled Pathway in Astrocytes That Regulates Apolipoprotein E-Mediated Cholesterol Efflux", The Journal of Biological Chemistry, May 5, 2006, pp. 12799-12808, vol. 281, No. 18, American Society for Biochemistry and Molecular Biology, Inc.

(Continued)

*Primary Examiner* — Shengjun Wang
(74) *Attorney, Agent, or Firm* — Khin K. Chin; Bozicevic Field & Francis LLP

(57) ABSTRACT

Methods of preventing and/or treating ischemia, organ dysfunction and/or organ failure, including multiple organ dysfunction syndrome (MODS), and necrosis and apoptosis associated with organ dysfunction/failure, are provided. For instance, the methods involve contacting organ(s) with an oxygenated cholesterol sulfate (OCS), e.g. 5-cholesten-3, 25-diol, 3-sulfate (25H-C3S). The organ(s) may be in vivo (e.g. in a patient that is treated with the OCS) or ex vivo (e.g. an organ that has been harvested from a donor and is to be transplanted).

21 Claims, 20 Drawing Sheets

Related U.S. Application Data continuation of application No. 15/106,883, filed as application No. PCT/US2014/072128 on Dec. 23, 2014, now Pat. No. 10,272,097.

(60) Provisional application No. 61/920,617, filed on Dec. 24, 2013.

(51) Int. Cl.

| A61K 31/568 | (2006.01) |
|---|---|
| A61P 13/12 | (2006.01) |
| A01N 1/02 | (2006.01) |
| A61K 35/12 | (2015.01) |

(58) Field of Classification Search
USPC .......................................................... 514/182
See application file for complete search history.

(56) References Cited

U.S. PATENT DOCUMENTS

| 3,928,397 | A | 12/1975 | Ikekawa et al. |
|---|---|---|---|
| 4,202,891 | A | 5/1980 | Schroepfer et al. |
| 4,225,524 | A | 9/1980 | Ochi et al. |
| 4,264,512 | A | 4/1981 | Okamura et al. |
| 4,427,668 | A | 1/1984 | Javitt |
| 4,743,597 | A | 5/1988 | Javitt et al. |
| 5,599,659 | A | 2/1997 | Brasile et al. |
| 6,645,953 | B2 | 11/2003 | Gronvald et al. |
| 6,923,988 | B2 | 8/2005 | Patel et al. |
| 7,524,493 | B2 | 4/2009 | Flugelman et al. |
| 8,399,441 | B2 | 3/2013 | Ren et al. |
| 9,034,859 | B2 | 5/2015 | Ren et al. |
| 9,321,802 | B2 | 4/2016 | Ren et al. |
| 9,480,692 | B2 | 11/2016 | Ren |
| 10,786,517 | B2 | 9/2020 | Ren et al. |
| 2002/0107233 | A1 | 8/2002 | Liao et al. |
| 2003/0077297 | A1 | 4/2003 | Chen et al. |
| 2003/0153541 | A1 | 8/2003 | Dudley et al. |
| 2004/0048838 | A1 | 3/2004 | Gronvald et al. |
| 2004/0152681 | A1 | 8/2004 | Liao et al. |
| 2005/0101573 | A1 | 5/2005 | Faarup et al. |
| 2006/0025393 | A1 | 2/2006 | Liao et al. |
| 2007/0197484 | A1 | 8/2007 | Song et al. |
| 2007/0275939 | A1 | 11/2007 | Ren et al. |
| 2010/0093687 | A1 | 4/2010 | Song et al. |
| 2010/0273761 | A1 | 10/2010 | Ren et al. |
| 2011/0077245 | A1 | 3/2011 | Van Der Aa et al. |
| 2011/0160174 | A1 | 6/2011 | Song et al. |
| 2012/0264816 | A1 | 10/2012 | Ren et al. |
| 2013/0143854 | A1 | 6/2013 | Ren et al. |
| 2015/0072962 | A1 | 3/2015 | Ren |
| 2016/0355544 | A1 | 12/2016 | Ren |
| 2017/0136038 | A1 | 5/2017 | Ren |
| 2018/0127457 | A1 | 5/2018 | Ren |
| 2018/0346509 | A9 | 12/2018 | Ren et al. |
| 2019/0135856 | A1 | 5/2019 | Ren |
| 2019/0169225 | A1 | 6/2019 | Ren et al. |
| 2019/0269695 | A1 | 9/2019 | Ren et al. |
| 2019/0374554 | A1 | 12/2019 | Ren et al. |
| 2020/0009158 | A1 | 1/2020 | Ren |
| 2020/0157140 | A1 | 5/2020 | Ren |
| 2020/0222430 | A1 | 7/2020 | Miksztal et al. |
| 2021/0147469 | A1 | 5/2021 | Ren et al. |

FOREIGN PATENT DOCUMENTS

| EP | | 2842547 | 3/2015 |
|---|---|---|---|
| EP | | 3639828 | 4/2020 |
| WO | WO | 1993025568 | 12/1993 |
| WO | WO | 1994003177 | 2/1994 |
| WO | WO | 1995015165 | 6/1995 |
| WO | WO | 1997000884 | 1/1997 |
| WO | WO | 1999058549 | 11/1999 |
| WO | WO | 2000066611 | 11/2000 |
| WO | WO | 2001015676 | 3/2001 |
| WO | WO | 2002062302 | 8/2002 |
| WO | WO | 2002090375 | 11/2002 |
| WO | WO | 2003039480 | 5/2003 |
| WO | WO | 2004017897 | 3/2004 |
| WO | WO | 2006047022 | 5/2006 |
| WO | WO | 2008078099 | 7/2008 |
| WO | WO | 2009088192 | 7/2009 |
| WO | WO | 2011077245 | 6/2011 |
| WO | WO | 2012017290 | 2/2012 |
| WO | WO | 2012074244 | 6/2012 |
| WO | WO | 2013036835 | 3/2013 |
| WO | WO | 2013154752 | 10/2013 |
| WO | WO | 2014015024 | 1/2014 |
| WO | WO | 2015100312 | 7/2015 |
| WO | WO | 2016057713 | 4/2016 |
| WO | WO | 2016058000 | 4/2016 |
| WO | WO | 2017019808 | 2/2017 |

OTHER PUBLICATIONS

Accad et al. "Cholesterol homeostasis: A role for oxysterols", Current Biology, 1998, p. R601-R604, vol. 8.

Adams et al., "Cholesterol and 25-Hydroxycholesterol Inhibit Activation of SREPBs by Different Mechanisms, Both Involving SCAP and Insigs", The Journal of Biological Chemistry, Dec. 10, 2004, pp. 52772-52780, vol. 279, No. 50, American Society for Biochemistry and Molecular Biology, Inc.

Agarwal et al., "CTLA-4 gene polymorphism confers susceptibility to primary biliary cirrhosis"; Journal of Hepatology vol. 32, Issue 4, Apr. 2000, pp. 538-541.

Ahmed et al., "PPARs and their Metabolic Modulation: New Mechamsms for Transcriptional Regulation?", Journal of Internal Medicine, 2007, vol. 262, p. 184-198.

Aksoy IA, et al., "Cholesterol Sulfation in human liver. Catalysis by dehydroepiandrosterone sulfotransferase"; Drug Metab Dispos. 21:268-276, 1993.

Australian New Zealand Clinical Trials Registry (ANZCTR), "an Intralesional Injection Study of DUR-928 in Psoriasis Patients" Trial ID ACRTN 12616001077459, Aug. 10, 2016, web.

Australian New Zealand Clinical Trials Registry (ANZCTR), "A Single Infusion of DUR-928 in Healthy Volunteers", Trial ID ACRTN 12616000856415, Jun. 30, 2016, web.

Australian New Zealand Clinical Trials Registry (ANZCTR), "A Single Injection Dose Study of DUR-928 in Patients with Impaired Kidney Function and Healthy Volunteers" Trial ID ACTRN 12616000389404, Jun. 24, 2016, web.

Australian New Zealand Clinical Trials Registry (ANZCTR), "A Single Oral Dose Study of DUR-928 in Nonalcoholic Steatohepatitis (NASH) Patients and Healthy Volunteers", Trial ID ACTRN 12515001355561, Dec. 14, 2015, web.

Australian New Zealand Clinical Trials Registry (ANZCTR), "A Single and Multiple Daily Injection Study of DUR-928 in Healthy Volunteers", Trial ID ACTRN 12615000903583, Aug. 28, 2015, web.

Australian New Zealand Clinical Trials Registry (ANZCTR), "A Multiple Daily Oral Dose Study of DUR-928 in Healthy Volunteers", Trial ID ACTRN 12615000267550, Mar. 20, 2015, web.

Australian New Zealand Clinical Trials Registry (ANZCTR), "First-in-Human, Single Ascending Oral Dose Study of DV-928 in Healthy Volunteers", Trial ID ACTRN 12614001022651, Sep. 24, 2014, web.

Axelson and Larsson, "27-Hydroxylated Low Density Lipoprotein (LDL) Cholesterol Can Be Converted to 7[alpha],27-3 Dihydroxy-4-cholesten-3-one (Cytosterone) before Suppressing Cholesterol Production in Normal Human Fibroblasts", The Journal of Biological Chemistry, May 31, 1996, pp. 12724-12736, vol. 271, No. 22, The American Society for D Biochemistry and Molecular Biology, Inc.

Babaev et al., "Macrophage expression of peroxisome proliferator-activated receptor-alpha reduces atherosclerosis in low-density lipoprotein receptor-deficient mice", CIRCULATION, 2007, pp. 1404-1412, vol. 116.

(56) References Cited

OTHER PUBLICATIONS

Bai et al., "Oxysterol sulfation by cytosolic sulfotransferase suppresses liver X receptor/sterol regulatory element binding protein-1c signaling pathway and reduces serum and hepatic lipids in mouse models of nonalcoholic fatty liver disease", Metabolism, 2012, pp. 836-845, vol. 61, Elsevier.

Bai Q, et al., "Sulfation of 25-hydroxycholesterol by SULT2B1b decreases cellular lipids via the LXR/SREBP-1c signaling pathway in human aortic endothelial cells"; Atherosclerosis. Feb. 2011; 214(2): 350-356.

Basra and Anand (2011) "Definition, epidemiology and magnitude of alcoholic hepatitis"; World J Hepatol. 3(5); pp. 108-113.

Beltowski, "Liver X Receptors (LXR) as Therapeutic Targets in Dyslipidemia", Cardiovascular Therapy, 2008, pp. 279-316, vol. 26.

Beaven SW, et al.; "Reciprocal Regulation of Hepatic and Adipose Lipogenesis by Liver X Receptors in Obesity and Insulin Resistance"; Cell Metabolism. 2013; 18, 106-117.

Bjoerkem, "Are side-chain oxidized oxysterols regulators also in vivo?", The Journal of Lipid Research, Apr. 2009, pp. S213-S218, vol. 50, American Society for Biochemistry and Molecular Biology, Inc.

Blaton, "Dyslipidemia at chronic renal failure," International Federation of Clinical Chemistry and Laboratory Medicine, 2009, vol. 20, No. 1, pp. 59-60 Ejifcc 20/01 http://www.ifcc.org.

Bocher V, et al., "Liver X Receptors: New Players in Atherogenesis?"; Current Opinion in Lipidology. 2003; 14(2):137-143.

Carey MC et al., "Solution properties of sulfated monohydroxy bile salts. Relative insolubility of the disodium salt of glycolithocholate sulfate"; Biochim.Biophys Acta 575:16-26, 1979.

Cases et al., "Dyslipidemia and the progression of renal disease in chronic renal failure patients," Kidney International, 2005, vol. 68, supplement 99, pp. s87-s93.

Cerpnjak K, et al (2013) "Lipid-based systems as a promising approach for enhancing the bioavailability of poorly water-soluble drugs"; Acta Pharm. 63(4); pp. 427-445.

Cha and Repa "The liver X receptor (LXR) and hepatic lipogenesis. The carbohydrate-response element-binding protein is a target gene of LXR", Journal of Biological Chemistry, Jan. 5, 2007, pp. 743-751, vol. 282, No. 1.

Cha and Kim "Sulfated oxysterol 25HC3S as a therapeutic target of non-alcoholic fatty liver disease", Metabolism, 2012, pp. 1055-1057, vol. 61, Elsevier.

Chang RK, et al (2013) "Generic development of topical dermatologic products: formulation development, process development, and testing of topical dermatologic products"; AAPS J. 15(1); pp. 41-52.

Chapman E. et al., "Sulfotransferases: Structure, mechanism, biological activity, inhibition, and synthetic utility"; Angew.Chem. Int. Ed Engl 43:3526-3548, 2004.

Chayanupatkul and Liangpunsakul (2014) "Alcoholic hepatitis: a comprehensive review of pathogenesis and treatment"; World J Gastroenterol. 20(20); pp. 6279-6286.

Chen et al., "Enzymatic Reduction of Oxysterols Impairs LXR Signaling in Cultured Cells and the Livers of Mice", Cell Metab., Jan. 2007, pp. 73-79, vol. 5, No. 1, Elsevier.

Chen et al. "Influenza A virus infection activities cholesterol sulfotransferase (Sul T2B1 b) in the lung of female C57BU6 mice". Biol. Chem., Oct. 2011, pp. 869-876, vol. 392.

Considine et al., "Serum immunoreactive-leptin concentration in normal-weight and obese humans," The New England Journal of Medicine, 1996, vol. 334, No. 5, pp. 292-295.

Cook et al. (2009) "24-Hydroxycholesterol Sulfation by Human Sytosolic Sulfotransferases: Formation of Monosulfates and Disulfates, Molecular Modeling, Sulfatase Sensitivity, and Inhibition of Liver X Receptor Activation", Drug Metabolism and Disposition, vol. 37, No. 10; pp. 2069-2078, , The American Society for Pharmacology and Experimental Therapeutics.

Corsini et al. "Effects of 26-Aminocholesterol. 27-Hydroxycholesterol, and 25-Hydroxycholesterol on Proliferation and Cholesterol Homeostasis in Arterial Myocytes", Arteriosclerosis, Thrombosis, and Vascular Biology, 1995, pp. 420-428, vol. 15, American Heart Association.

Crabb DW, et al (2020) "Diagnosis and Treatment of Alcohol-Associated Liver Diseases: 2019 Practice Guidance From the American Association for the Study of Liver Diseases"; Hepatology 71(1); pp. 306-333.

Crabb DW, et al (2016) "Standard Definitions and Common Data Elements for Clinical Trials in Patients With Alcoholic Hepatitis: Recommendation From the NIAAA Alcoholic Hepatitis Consortia"; Gastroenterology. 150(4); pp. 785-790.

Dao and Rangnekar (2018) "Steroids for Severe Alcoholic Hepatitis: More Risk Than Reward?"; Clin Liver Dis (Hoboken) 12(6); pp. 151-153.

DePass, et al; "In Vivo Tissue Distribution and Elimination of DUR-928, a First in Class Therapeutic for Treatment of Hepatic and Renal Disease"; Abstract #3355/Poster Board #P137, Late Breaking SOT Poster, Toxicokinetics, 57thAnnual Meeting of the Society of Toxicology, San Antonio, Texas, Mar. 11-15, 2018.

DePass, et al; "A 14-Day Intravenous Infusion Toxicity and Toxicokinetic Study of DUR-928, a Novel, First in Class, Investigational Therapeutic in Sprague-DawleyRats"; American College of Toxicology's 39th Annual Meeting, West Palm Beach, Florida, Nov. 4-7, 2018.

Diczfalusy U. "On the Formation and Possible Biological Role of 25-hydroxycholesterol"; Biochimie. 2013; 95 (3):455-460.

Drinane and Shah (2013) "Alcoholic Hepatitis: Diagnosis and Prognosis"; Clinical Liver Disease, vol. 2, No. 2,; pp. 8-83.

Ducheix S, et al., "The Liver X Receptor: A Master Regulator of the Gut-Liver Axis and a Target for Non Alcoholic Fatty Liver Disease"; Biochemical Pharmacology. 2013; 86(1): 96-105.

Durect, (2018) "A Research Study to Assess the Safety, Pharmacokinetics and Pharmacodynamics of DUR-928 in Patients With Alcoholic Hepatitis (AH)"; U.S. National Library of Medicine, ClinicalTrials.gov Identifier: NCT03432260; 14 pages.

Durect (2018) "A Research Study to Evaluate Safety and Efficacy of DUR-928 in Subjects With Primary Sclerosing Cholangitis (PSC)"; U.S. National Library of Medicine, ClinicalTrials.gov Identifier: NCT03394781; 13 pages.

Duvnjak et al., "Pathogenesis and management issues for non-alcoholic fatty liver disease"; World journal of gastroenterology, 13(34). pp. 4539-4550. 2007.

Englund et al., "25-hydroxycholesterol induces lipopolysaccharide-lolerance and decreases a lipopolysaccharide-induced TNF-[gamma] secretion inmacrophages", Atherosclerosis, 2001, pp. 61-71, vol. 158, Elsevier.

European Association for the Study of Liver (2012) "EASL Clinical Practical Guidelines: Management of Alcoholic Liver Disease"; Journal of Hepatology vol. 57; pp. 399-420.

Falany CN., Sulfation and sulfotransferases. Introduction: changing view of sulfation and the cytosolic sulfotranferases, FASEB J. 11" 1-2, 1997.

Feng et al., "The role of leptin in obesity and the potential for leptin replacement therapy" Endocrine, 2013, vol. 44, pp. 33-39 (Year: 2013).

Fuda et al., "Mutational Analysis of Human Hydroxy steroid Sulfotransferase SUL T2B1 1soforms Reveals That Exon IB of the SULT2B1 Gene Produces Cholesterol Sulfotransferase, whereas Exon 1A Yields Pregnenolone Sulfotransferase", The Journal of Biological Chemistry, Sep. 27, 2002, pp. 36161-36166, vol. 277, No. 39, American Society for Biochemistry and Molecular Biology, Inc.

Fuda et al., "Oxysterols are substrates for cholesterol sulfotransferase", The Journal of Lipid Research, Mar. 2007, pp. 1343-1352, vol. 48, American Society for Biochemistry and Molecular Biology, Inc.

Geese and Raftogianis, "Biochemical Characterization and Tissue Distribution of Human SULT2B1", Biochemical and Biophysical Research Communications, 2001, pp. 280-289, vol. 288, Academic Press.

Gill et al., "Sterol regulators of cholesterol homeostasis and beyond: The oxysterol hypothesis revisited and revised", Progress in Lipid Research, 2008, pp. 391-404, vol. 47, Elsevier.

Grefhorst et al., "Stimulation of Lipogenesis by Pharmacological Activation of the Liver X Receptor Leads to Production of Large, Triglyceride-rich Very Low Density Lipoprotein Particles", Lipids and Lipoproteins, Sep. 13, 2002, pp. 34182-34190, vol. 277, No. 37.

(56) References Cited

OTHER PUBLICATIONS

Griffett K, et al, "A Liver-Selective LXR Inverse Agonist that Suppresses Hepatic Steatosis"; ACS Chemical Biology. 2013; 8(3):559-567.

Gross et al., Quality of Life Before and After Liver Transplantation for Cholestatic Liver Disease. H Epatology 1999;29:356-364 (Year: 1999).

Hassanein, et al (2019) "Safety and Efficacy of DUR-928: A Potential New Therapy for Acute Alcoholic Hepatitis" AASLD; Abstract LB-09 (Durect C928-010 Trail); 1 page.

Hassanein, et al (2019) "Safety and Efficacy of DUR-928: A Potential New Therapy for Acute Alcoholic Hepatitis"; AASLD; 22 pages.

He et al., "Identification and immunohistochemical localization of Sulfotransferase 2B1b (SULT2B1b) in human lung'"; Biochimica et Biophysica Acta, Apr. 12, 2005, pp. 119-126, vol. 1724, Elsevier.

He D., et al, "Inhibition of SULT2B1B expression alters effects of 3 beta-hydroxysteroids on cell proliferation and steroid hormone receptor in human LNCaP prostate cancer cells"; Prostate 67-1318-1329, 2007.

Higashi et al., "Expression of Cholesterol Sulfotransferase (SULT2B1b) in Human Skin and Primary Cultures of Human Epidermal Keralinocytes", The Journal of Investigative Dermatology, 2004, pp. 1207-1212, vol. 122, The Society for Investigative Dermatology.

Horton J, et al "SREBPs: activators of the complete program of cholesterol and fatty acid synthesis in the liver"; The Journal of Clinical Investigation. 2002; 109(9):1125-1131.

Horton J, et al. "Combined analysis of oligonucleotide microarray data from transgenic and knockout mice identifies direct SREBP target genes"; PNAS. 2003; 100(21): 12027-12032.

Ikegami et al., "Increased serum liver X receptor ligand oxysterols in patients with non-alcoholic fatty liver disease", J Gastroenterol, May 9, 2010, pp. 1257-1266, vol. 47, SPRINGER.

Itoh, et al (1999) "Synthesis of 6- and 7-hydroxyestradiol 17-sulfates: The potential metabolites of estradiol 17-sulfate by female rat liver microsomes"; Steroids 64; pp. 363-370.

Janout et al., "An Upside Down View of Cholesterol's Condensing Effect: Does Surface Occupancy Play a Role?", Langmuir, Apr. 20, 2010, pp. 5316-5318, vol. 26, No. 8.

Janowski et al., "An oxysterol signalling pathway mediated by the nuclear receptor LXR alpha"; Letters To Nature, Oct. 24, 1996, pp. 728-731, vol. 383.

Janowski et al., "Structural requirements of ligands for the oxysterol liver X receptors LXRα and LXRβ", Proc Natl Acad Sci U S A. Jan. 5, 1999;96(1):266-71.

Javitt et al., "Cholesterol and hydroxycholesterol sulfotransferases: Identification, distinction from dehydroepiandrosterone sulfotransferase, and differential tissue expression". Endocrinology, vol. 142, pp. 2978-2984, 2001.

Ji et al., "Human Hydroxysteroid Sulfotransferase SULT2B1 Pharmacogenomics: Gene Sequence Variation and Functional Genomics", The Journal of Pharmacology and Experimental Therapeutics, 2007, pp. 529-540, vol. 322, No. 2, The American Society for Pharmacology and Experimental Therapeutics.

Jinjuvadia and Liangpunsakul (2015) "Trends in Alcoholic Hepatitis-related Hospitalizations, Financial Burden, and Mortality in the United States"; J Clin Gastroenterol. 49(6); pp. 506-511.

Jones et al., Hepatocellular Carcinoma in Primary Biliary Cirrhosis and its impact on outcomes. Hepatology, 1997, 26:1138-1142 (Year:1997).

Kase et al., "Liver X receptor antagonist reduces lipid formation and increases glucose metabolism in myotubes from lean, obese and type 2 diabetic individuals", Diabetologia, 2007, pp. 2171-2180, vol. 50, Springer-Verlag.

Kasakabe, Toru, et al (2010) "Congenital deficiency of leptin and its receptor in humans"; Japanese Journal of Clinical Medicine, vol. 68, extra issue 2, p. 486-490.

Kawata et al.,"Effect of pravastatin on survival in patients with advanced hepatocellular carcinoma. A randomized controlled trial"; British Journal of Cancer (2001) 84(7), 886-891 (Year:2001).

Kay and Fausto, Liver regeneration: prospects for therapy based on new technologies; Molecular Medicine Today, Mar. 1997, pp. 108-115.

Kemp, W., "Safety and pharmacokinetics of DUR-928 in patients with non-alcoholic steatohepatitis—A Phase 1b study", EASL The International Liver Congress; Apr. 2017.

Khan and Glenton (2008) "Calcium oxalate crystal deposition in kidneys of hypercalciuric mice with disrupted type IIa sodium-phosphate cotransporter"; Am J Physiol Renal Physiol. 294(5):F1109-15.

Kim, Mee J., "DUR-928, an endogenous regulatory molecule, exhibits anti-inflammatory and antifibrotic activity in a mouse model of NASH", AASLD's Emerging Trends in NAFLD, Washington DC; Mar. 17-18, 2017.

Kim MJ, et al; "Attenuation of Renal Ischemic Reperfusion Injury in Rats with DUR-928, a Novel, First-in-Class Therapeutic in Development for Renal Disease"; Poster #: SA-PO650, Kidney Week, San Diego, CA-Oct. 23-28, 2018.

Kim and Kim (2014) "Severe alcoholic hepatitis-current concepts, diagnosis and treatment options"; World J Hepatol. 6(10); pp. 688-695.

Landis et al., "Oxysterol Activators of Liver X Receptor and 9-cis-Retinoic Acid Promote Sequential Steps in the Synthesis and Secretion of Tumor Necrosis Factor-alpha from Human Monocytes", Journal of Biological Chemistry, Feb. 15, 2002, pp. 4713-4721, vol. 277, No. 7.

Lappano et al., "The Cholesterol Metabolite 25-Hydroxycholesterol Activates Estrogen Receptor a-Mediated Signaling in Cancer Cells and in Cardiomyocytes", PloS ONE, Jan. 31, 2011, pp. e16631-e16631, vol. 6, No. 1.

Lee YC. et al., "Sp1 elements in SULT2B1b promoter and 5'-untranslated region of mRNA: Sp1/Sp2 induction and augmentation by histone deacetylase inhibition"; FEBS Lett. 579:3639-3645, 2005.

Lehmann et al., "Activation of the Nuclear Receptor LXR by Oxysterols Defines a New Hormone Response Pathway", The Journal of Biological Chemistry, Feb. 7, 1997, pp. 3137-3140, vol. 272, No. 6.

Li et al., "A Novel Metabolic Pathway for the Synthesis of the Newly Discovered Nuclear 5-cholesten-3beta, 25-diol 3-sulphate", Abstract.

Li et al., "Biosynthesis of the regulatory oxysterol, 5-cholesten-3β,25-diol 3-sulfate, in hepatocytes", Journal of Lipid Research, Sep. 21, 2007, pp. 2587-2596, vol. 48.

Li et al., "Enzyme activity assay for cholesterol 27-hydroxylase in mitochondria", Journal of Lipid Research, Apr. 12, 2006, pp. 1507-1412, vol. 47.

Li et al. (1999) "Sterol synthesis. Preparation and characterization of fluorinated and deuterated analogs of oxygenated derivatives of cholesterol"; Chemistry and Physics of Lipids 99; pp. 33-71.

Lindsay, J; et al., (2008) "Structure, function and polymorphism of human cytosolic sulfotransferases"; Curr.Drug Metab 9:99-105.

Liu et al., "Nuclear Transport Modulation Reduces Hypercholesterolemia, Atherosclerosis, and Fatty Liver", Journal of The American Heart Association, Apr. 5, 2013, American Heart Association, Dallas, TX.

Lo Sasso et al., "Down-Regulation of the LXR Transcriptome Provides the Requisite Cholesterol Levels to Proliferating Hepatocytes", Hepatology, 2010, pp. 1334-1344, vol. 51.

Lo Sasso G, et al. (2010). Intestinal Specific LXR Activation Stimulates Reverse Cholesterol Transport and Protects from Atherosclerosis. Cell metabolism. 2010; 12(2), 187-193.

Lopez-Velazquez JA, et al., "Nuclear Receptors in Nonalcoholic Fatty Liver Disease"; Journal of Lipids. 2012.; 2012, Article ID 139875.

Lucey, et al (2009) "Alcoholic hepatitis"; N Engl J Med. 360(26); 2758-2769.

Lund EG. et al., "cDNA cloning of mouse and human cholesterol 25-hydroxylases, polytopic membrane proteins that synthesize a potent oxysterol regulator of lipid metabolism". J. Bio. Chem. 273:34316-34327, 1998.

(56) References Cited

OTHER PUBLICATIONS

Luu W. et al., "Oxysterols: Old Tale, New Twists"; Annu Rev Pharmacol Toxicol. 56:447-67:2016.
Ma et al., "25-Hydroxycholesterol-3-sulfate regulates macrophage lipid metabolism via the LXR/SREBP-1 signaling pathway", Am J Physiol Endocrinol Metab, Oct. 14, 2008, pp. E1369-E1379, vol. 295.
Markus et al., Efficacy of Liver Transplantation in Patients with Primary Biliary Cirrhosis. N Engl J Med 1989; 320:1709-1713.
McClain, Craig J., "Which Therapeutic Targets Will Be The Most Attractive In The Future?", Oct. 2017.
McClain, et al (2019) "DUR-928 Therapy For Acute Alcoholic Hepatitis: A Pilot Study"; AASLD; Poster (Durect Corporation); 1 page.
McCormack and Gregoriadis (1994) "Drugs-in-cyclodextrins-in liposomes:a novel concept in drug delivery"; International Journal of Pharmaceutics 112; pp. 249-258.
McDonald and Russel, "25-Hydroxycholesterol: a new life in immunology", Journal of Leukocyte Biology, Dec. 2010, pp. 1071-1072, vol. 88, Society for Leukocyte Biology.
Meloche and Falany, "Expression and characterization of the human 3[beta]-hydroxysteroid sulfotransferases (SULT2B1a and SULT2B1b)", Journal of Steroid Biochemistry & Molecular Biology, 2001, pp. 261-269, vol. 77, Elsevier.
Millatt et al., "Liver X receptors and the control of cholesterol homeostasis: potential therapeutic targets for the treatment of atherosclerosis", Biochimica Et Biophysica Actia, 2003, pp. 107-118, No. 1631.
Monsalve, et al. Peroxisome Proliferator-Activated Receptor Targets for the Treatment of Metabolic Diseases; Mediators of Inflammation. 2013.
Napodano, Jason et al., Zacks Small-Cap Research, Mar. 4, 2015, pp. 1-14.
Nelson et al., "The Oxysterol, 27-Hydroxycholesterol, Links Cholesterol Metabolism to Bone Homeostasis Through Its Actions on the Estrogen and Liver X Receptors", Endocrinology, Sep. 20, 2011, pp. 1-15, vol. 152, No. 12, The Endocrine Society.
Ning, Yanxia, "Cholesterol metabolites alleviate injured liver function and decrease mortality in an LPS-induced mouse model", Metabolism Clinical and Experimental, 71 (2017), 83-93.
Nograles and Krueger (2011) "Anti-cytokine therapies for psoriasis"; Exp Cell Res; 317(9); pp. 1293-1300.
Ogawa et al., "A facile synthesis of C-24 and C-25 oxysterols by in situ generated ethyl(trifluoromethyl)dioxirane", Steroids, 2009, pp. 81-87, vol. 74, Elsevier.
Okamura et al., "Studies on vitamin D and its analogs. VIII. 3-deoxy-1α,25-dihydroxyvitamin $D_3$, a potent new analog of 1α,25-(OH)2-$D_3$", Biochemical and Biophysical Research Communications, 1975, pp. 24-30, vol. 65, No. 1, Academic Press, Inc.
Okamura et al., "Studies on Vitamin D (Calciferol) and Its Analogues. 13. 3-Deoxy-3α-methyl-1α-hydroxyvitamin $D_3$, 3-Deoxy-3α-methyl-1α,25-dihydroxyvitamin $D_3$, and 1α-Hydroxy-3-epivitamin $D_3$. Analogues with Conformationally Biased A Rings", Journal of Organic Chemistry, 1978, pp. 574-580, vol. 43, No. 4, American Chemical Society.
O'Shea, et al (2010) "Alcoholic Liver Disease"; Hepatology, vol. 51, No. 1; pp. 307-328.
Owens, et al (2016) "Pharmacologic Treatment of Alcoholic Hepatitis: Examining Outcomes Based on Disease Severity Stratification"; J Clin Exp Hepatol. 6(4); pp. 275-281.
Pandak, et al., "Regulation of Oxysterol 7α-Hydroxylase (CYP7B1) in Primary Cultures of Rat Hepatocytes", Hepatology, 2002, pp. 1400-1408, vol. 35, No. 6, American Association for the Study of Liver Diseases.
Pandak, et al., "Transport of Cholesterol into Mitochondria is Rate-limiting for Bile Acid Synthesis via the Alternative Pathway in Primary Rat Hepatocytes", The Journal of Biological Chemistry, Oct. 3, 2002, pp. 48158-48164, vol. 277, No. 50.
Parker and McCune (2013) "Diagnosis and treatment of alcoholic hepatitis"; Frontline Gastroenterology; pp. 1-7.
Peet et al., "Cholesterol and Bile Acid Metabolism Are Impaired in Mice Lacking the Nuclear Oxysterol Receptor LXRα", Cell, May 29, 1998, pp. 693-704, vol. 93, Cell Press.
Peet et al., "The LXRs: a new class of oxysterol receptors", Current Opinions In Genetics And Development, 1998, pp. 571-575, vol. 8.
Perez et al., "Bile-acid-induced cell injury and protection"; World J Gastroenterol Apr. 14, 2009; 15(14): 1677-1689 (Year: 2009).
Pezacki et al. "Transcriptional profiling of the effects of 25-hydroxycholesterol on human hepatocyte metabolism and the antiviral state ii conveys against the hepatitis C virus", BMC Chemical Biology, Jan. 16, 2009, vol. 9, No. 2, BioMed Central Lid.
Picard et al. (2012) "Mitochondrial dysfunction and lipid accumulation in the human diaphragm during mechanical ventilation"; Am J Resp Critical Care Med 186:1140.
Polyzos, et al. "Sulfated oxysterols as candidates for the treatment of nonalcoholic fatty liver disease"; Metabolism, 2012, pp. 755-758, vol. 61, Elsevier.
Quintero P. and Arrese M. (2013) "Nuclear Control of Inflammation and Fibrosis in Nonalcoholic Steatohepatitis: Therapeutic Potential of Dual Peroxisome Proliferator—Activated Receptor Alpha/Delta Agonism"; Hepatology 58(6), pp. 1881-1884.
Reboldi A. et al., "Inflammation 25-Hydraxycholesterol suppresses interleukin-1-driven inflammation downstream of type I interferon"; Science 345:679-684, 2014.
Ren et al., "Identification of A Novel Regulatory Nuclear Oxysterol", Abstract, 56rd Annual Meeting of the American Association for the Study of Liver Diseased, Nov. 11-15, 2005.
Ren et al., "25-hydroxycholesterol and 25-hydroxycholesterol 3-sulfate reciprocally regulate lipid metabolism and inflammation in hepatocytes and macrophages", Abstract, The Liver Meeting, the 60th Annual Meeting of the American Association for the Study of Liver Diseases, Oct. 30-Nov. 3, 2009.
Ren et al., "25-Hydroxycholesterol sulfation regulates lipid metabolism in vivo in mice", Jun. 13-14, 2008; Abstract.
Ren et al., "Discovery of a Novel Oxysterol, 5-Cholesten-3beta, 25-Diol 3-Sulfonate, in Nuclei and Mitochondria Following Overexpression of the Gene Encoding StarD1", Bile Acids: Biological Actions and Clinical Relevance, 2007 pp. 20-35, Kluwer Academic Publishers.
Ren et al., "Discovery of a Novel Oxysterol, 5-Cholesten-3beta, 25-Diol 3-Sulfonate, in Nuclei and Mitochondria Following Overexpression of the Gene Encoding StarD1", Abstract, International Bile Acid Meeting, XIII Falk Liver Week, Falk Symposia 155, Oct. 6-11, 2006.
Ren et al., "Discovery of a Novel Regulatory Pathway for Maintenance of Intracellular Cholesterol Homeostasis", Abstract, DOW Annual Meeting 2007, May 19-25, 2007.
Ren et al., "Identification of Novel Regulatory Cholesterol Metabolite, 5-Cholesten, 3β,25-Diol, Disulfate" PLOS One, Jul. 2014, vol. 9. No. 7, p. 1-11.
Ren et al. "Identification of a novel sulfonated oxysterol, 5-cholesten-3β,25-diol 3-sulfonate, in hepatocyte nuclei and mitochondria"; Journal of Lipid Research, Feb. 27, 2006, pp. 1081-1090, vol. 47, American Society for Biochemistry and Molecular Biology, Inc.
Ren, Shunlin, "Novel Oxysterol Sulfates Alleviate Injured Liver Function and Decrease Mortality in Mouse Models", Nov. 2017.
Ren et al., "Overexpression of Cholesterol Transporter StAR Increases In Vivo Rates of Bile Acid Synthesis in the Rat and Mouse"; Liver Biology and Pathobiology, Aug. 20, 2004, pp. 910-917, vol. 40, No. 4.
Ren et al., "Regulation of Hepatocyte Lipid Metabolism by 25-Hydroxycholesterol-3-Sulfate (25HC3S) Is Mediated Via the LXR/SREBP-1 Signaling Pathway"; Abstract, DOW Annual Meeting 2008, May 17-23, 2008.
Ren S., et al., "Sulfated oxsterol, 25HC3S, is a potent regulator of lipid metabolism in human hepatocytes", ScienceDirect, BBRC, 360 (2007) pp. 802-808.
Ren and Ning, "Sulfation of 25-hydroxycholesterol regulates lipid metabolism, inflammatory responses, and cell proliferation", Am J Physiol Endocrinol Metab, Dec. 3, 2013, pp. E123-E130, vol. 306.
Ruan X, et al., "PPARs and the kidney in metabolic syndrome", AJP-Renal Physiol, vol. 294, Jan. 30, 2008.

(56) References Cited

OTHER PUBLICATIONS

Shah, et al; "A Clinical Drug-Drug Interaction Study with Midazolam to Assess the Effect of DUR-928 on CYP3A4"; Meeting of the American College of Clinical Pharmacology, Bethesda, Maryland, Sep. 23-25, 2018; 1 page.

Shah, et al; "Safety and Single Ascending Dose Pharmacokinetic Study of DUR-928 in Patients with Chronic Kidney Disease versus Matched Control Subjects"; Poster #: SA-PO63; Kidney Week, San Diego, CA—Oct. 23-28, 2018; 1 page.

Shah, et al; "Pharmacokinetic and Pharmacodynamic Response in Individual NASH Patients Receiving Two Dose Levels of DUR-928"; Nash Summit-2019, Apr. 22-25, 2019. 1 page.

Shepherd et al., "Effective of intensive lipid lowering with atorvastatin on renal function in patients with coronary heart disease: the treatment of new targets study," Clin. J. Am. Soc. Nephrol. vol. 2, pp. 1131-1139.

Shi et al., "Cholesterol Sulfate and Cholesterol Sulfotransferase Inhibit Gluconeogenesis by Targeting Hepatocyte Nuclear Factor 4α", Molecular and Cellular Biology, Feb. 1, 2014, vol. 34, No. 3, p. 485-497.

Shimizu et al., "Conservation of the Hydroxy steroid Sulfotransferase SULT2B1 Gene Structure in the Mouse: Pre- and Postnatal Expression, Kinetic Analysis of Isoforms, and Comparison with Prototypical SULT2A1"; Endocrinology, Apr. 2003, pp. 1186-1193, vol. 144, No. 4, The Endocrine Society.

Song et al. "Auto-oxidized cholesterol sulfates are antagonistic ligands of liver X receptors: implications for the development and treatment of atherosclerosis". Steroids. 2001. pp. 473-479, vol. 66, Elsevier.

Strott and Higashi, "Cholesterol sulfate in human physiology: what's it all about?", Journal of Lipid Research, 2003, pp. 1268-1278, vol. 44.

Su et al., "Hypercholesterolemia in Primary Biliary Cirrhosis"; N Eng J Med 357;15:1561-1562.

Taddei et al., "High incidence of cholesterol gallstone disease in type 1 Gaucher disease: characterizing the biliary phenotype of type 1 Gaucher disease," J. Inherit Metab Dis. 2010, vol. 33, pp. 291-300).

Tan et al., "Leptin Deficiency contributes to the pathogenesis of alcoholic fatty liver disease in mice", The American Journal of Pathology, 2012, vol. 181, No. 10, pp. 1279-1286 (Year: 2012).

Thakar et al., "Acute kidney injury episodes and chronic kidney disease risk in diabetes mellitus"; Clin. J. Am. Soc. Nephrol. 2011, vol. 6, pp. 2567-2572. (Year: 2011).

Therapeutics, Inc. (2019) "Safety and Efficacy Study of DUR-928 Topical Solution in Subjects With Plaque Psoriasis"; U.S. National Library of Medicine, ClinicalTrials.gov Identifier: NCT03837743; 14 pages.

Teh, et al., "Hepatic Resection of Hepatocellular Carcinoma in Patients with Cirrhosis: Model of End-Stage Liver Disease (MELD) Score Predicts Perioperative Mortality"; Journal of Gastrointestinal Surgery. vol. 9, No. 9, 200-5, pp. 1207-1215 (Year:2005).

Treuter, "New wrestling rules of anti-inflammatory transrepression by oxysterol receptor LXR revealed", Cell Research, 2011, pp. 711-714, vol. 21.

Trousson et al., "25-hydroxycholesterol provokes oligodendrocyte cell line apoptosis and stimulates the secreted phospholipase A2 type IIA via LXR beta and PXR"; Journal of Neurochemistry, 2009, pp. 945-958, vol. 109.

Wagner BL, et al. "Promoter-Specific Roles for Liver X Receptor/Corepressor Complexes in the Regulation of ABCA1 and SREBP-1 Gene Expression"; Mal. Cell. Biol. 2003; 23(16):5780.

Weinberg (2006) "Lipotoxicity"; Kidney International 70:1560.

Williams et al., "Effects of cholesterol sulfate on lipid metabolism in cultured human keratinocytes and fibroblasts"; Journal of Lipid Research, vol. 28, pp. 955-967, 1987.

Wojcicka et al., "Liver X receptors (LXRs). Part I: Structure, function, regulation of activity, and role in lipid metabolism", Postepy Hig Med Dosw., Dec. 3, 2007, pp. 736-759, vol. 61.

Xu et al., "25-Hydroxycholesterol (25HC) and 25HC-3-Sulfate (25HC3S) Mediate Nuclear Orphan Receptors in Opposite Direction in Hepatocytes", Abstract, XX International Bile Acid Meeting, Falk Symposia 165, Jun. 13-14, 2008.

Xu et al.., "25-Hydroxycholesterol-3-sulfate (25HC3S) Attenuates Hepatocyte Intracellular Lipid Levels and Inflammatory Response via LXR/SREBPs and IKBa/NF-KB Pathways", Abstract, DOW Annual Meeting 2008, May 3, 2010.

Xu et al., "25-Hydroxycholesterol-3-sulfate attenuates inflammatory response via PPARγ signaling in human THP-1 macrophages", Am J Physiol Endocrinol Metab, Jan. 24, 2012, pp. E788-E799, vol. 302.

Xu et al.., "25-Hydroxycholesterol-3-Sulfate Decreases Hepatic Steatosis and Inflammation In Mouse Models of Nonalcoholic Fatty Liver Disease by Down-Regulating Sterol Regulatory Element Binding Protein-1c", Abstract, DOW Annual Meeting 2011, May 7-10, 2011.

Xu et al., "Induction of IκBα Expression as a Mechanism Contributing to the Anti-inflammatory Activities of Peroxisome Proliferator-activated Receptor-α Activators", Abstract, DOW Annual Meeting 2011, May 7-10, 2011.

Xu et al., "Induction of IKBα Expression Mediates the Anti-Inflammatory Response to 25-Hydroxycholesterol-3-Sulfate (25HC3S) in Primary Rat Hepatocytes and THP-1 Macrophages"; AASLD Abstract; 2011.

Xu et al., "Regulation of Hepatocyte Lipid Metabolism and inflammatory Response by 25-Hydroxycholesterol and 25-Hydroxycholesterol-3-sulfate", Lipids, 2010, pp. 821-832, vol. 45, AOCS.

Xu et al. "Reversal of Diet-induced Serum and Hepatic Lipid Accumulation by 5-cholesten-3beta.25-diol 3-sulfate in Mouse Models of Nonalcoholic Fatty Liver Diseases"; Hepatology, Jun. 9, 2011.

Xu et al., "5-Cholesten-3β,25-Diol 3-Sulfate Decreases Lipid Accumulation in Diet-Induced Nonalcoholic Fatty Liver Disease Mouse Model", Molecular Pharmacology, Mar. 2013, 648-658, vol. 83.

Zager et al. (2011) "Acute unilateral ischemic renal injury induces progressive renal inflammation, lipid accumulation, histone modification, and "end-stage" kidney disease."; Am J Physiol Renal Physiol 30:F1334.

Zelcer N and Tontonoz P. "Liver X receptors as integrators of metabolic and inflammatory signaling"; J Clin Invest. 2006; 116(3):607-614.

Zhang et al., "Cholesterol metabolite, 5-cholesten-3β-25-diol-3-sulfate, promotes hepatic proliferation in mice"; Journal of Steroid Biochemistry and Molecular Biology, 2012, pp. 262-270, vol. 132, Elsevier.

Zhang et al., "Cytosolic sulfotransferase 2B1b promotes hepatocyte proliferation gene expression in vivo and in vitro", Am J Physiol Gastrointest Liver Physiol, Jun. 7, 2012, pp. G344-G355, vol. 303.

Zhang et al., "Effects of 25-hydroxycholesterol sulfation on liver regeneration in normal and partial hepatectomy (PHX) mouse models", Abstract, DOW Annual Meeting 2011, May 7-10, 2011.

Zhang et al., "Effects of 25-Hydroxycholesterol Sulfation on Liver Regeneration in Normal and Partial Hepatectomy (PHX) Mouse Models"; May 2011, Gastroenterology vol. 140, Issue 5, Supplement 1, p. S-967.

Zhang et al., "SULT2B1b overexpression promotes liver regeneration via inhibiting LXR signaling pathway in mouse with or without Partial Hepatectomy", Poster; 1Departments of Medicine, Virginia Commonwealth University/McGuire Veterans Affairs Medical Center, Richmond, Virginia.

Zhang Hengai et al., "Advances in the research on drugs for the prevention and treatment of renal diseases with PPAR as target site", China Pharmaceutical Journal, vol. 45, No. 7, Apr. 30, 2010.

Zitvogel et al. (2010) "Decoding cell death signals in inflammation and immunity"; Cell 140(6); pp. 798-804.

Zuercher et al., "Discovery of Tertiary Sulfonamides as Potent Liver X Receptor Antagonists", J. Med. Chem., 2010, pp. 3412-3416, vol. 53, No. 8, American Chemical Society.

Bai, et al "Overexpression of Oxy sterol Sulfotransferase (Sult2B1 b) Decreases Intracellular Lipid Levels via SREBPs Signaling Pathway in Primary Human Aorta Endothelial Cells"; Abstract, Arteriosclerosis, Thrombosis, and Vascular Biology 2010 Scientific Sessions, American Heart Association; Apr. 8-10, 2010.

(56) References Cited

OTHER PUBLICATIONS

Ferrante Jr., et al (2001) "Effects of Leptin Deficiency and Short-Term Repletion on Hepatic Gene Expression in Genetically Obese Mice"; Diabetes 50(10); pp. 2268-2278.
Kanjanabuch T, et al (2007) "PPAR-γ agonist protects podocytes from injury"; Kidney Int. 71(12); pp. 1232-1239.
Kasisk, et al (1988) "Pharmacologic treatment of hyperlipidemia reduces glomerular injury in rat 5/6 nephrectomy model of chronic renal failure"; Circulation Research vol. 62, No. 2; pp. 367-374.
Levine, et al (2006) "Argatroban Therapy in Heparin-Induced Thrombocytopenia With Hepatic Dysfunction"; Chest, vol. 129, Issue 5; pp. 1167-1175.
Reel B., et al (2013) "The effects of PPAR-γ agonist pioglitazone on renal ischemia/reperfusion injury in rats"; J Surg Res. 182(1); pp. 176-184.
Ren et al, "25-Hydroxycholesterol-3-sulfate (25HC3S) regulates lipid metabolism by activation/inactivation of receptors in hepatocytes and macrophages", Abstract, XX International Bile Acid Meeting, Falk Symposium 165; Jun. 13-14, 2008.
Ren, et al "25-Hydroxycholesterol-3-Sulfate Activates PPARgamma and Attenuates Inflammatory Responses in Human Macrophages"; Poster Abstract, Arteriosclerosis, Thrombosis, and Vascular Biology Annual Conference 2009, American Heart Association; Apr. 29-May 1, 2009.
Ren S., et al.; "The acidic pathway of bile acid biosynthesis: Role in oxysterol sulfation, lipid metabolism and inflammatory responses"; Poster Abstract, XXII International Bile Acid Meeting, Falk Symposia 184; Sep. 14-15, 2012.
Ren, et al; "Oxysterol sulfates alleviate injured liver function and decrease mortality in mouse models"; Poster Abstract, XXV International Bile Acid Meeting:Bile Acids in Health and Disease, Symposium 211; Jul. 6-7, 2018.
Sivarajah A., et al (2003) "Agonists of peroxisome-proliferator activated receptor-gamma reduce renal ischemia/reperfusion injury"; Am J Nephrol. 23(4); 267-276.
Spahr et al. (2011) "Early liver biopsy, intraparenchymal cholestasis, and prognosis in patients with alcoholic steatohepatitis"; BMC Gastroenterology, 11:115; pp. 2-9.
Stranz, M. "The implications of osmolality, osmolarity and pH"; INS Annual Conference, pp. 1-5, https://piccresource.com/Short%201V%20Insertion%20Sample/Short%201V%201insertion%20Self%20Studydata/downloads/marc%20stranz%202005%20fall%20ins%20handout.pdf Accessed from the internet Jul. 7, 2020 (Year: 2005).
Wang, et al (2020) "High Glucose Induces Lipid Accumulation via 25-Hydroxycholesterol DNA-CpG Methylation"; iScience 23(5); pp. 1-28.
Xu et al., "25-Hydroxycholesterol-3-Sulfate (25HC3S) Suppresses NF-kB Activatioand Inflammatory Response in Human Macrophages and Hepatocytes", Abstract, Arteriosclerosis, Thrombosis, and Vascular Biology 2010 Scientific Sessions, American Heart Association; Apr. 8-10, 2010.
Zaffanello, et al (2009) "Acute non-oliguric kidney failure and cholestatic hepatitis induced by ibuprofen and acetaminophen: a case report"; Acta Paediatr 98(5); pp. 903-905.
Zuo, et al (2012) "Protective effects of PPARγ agonist in acute nephrotic syndrome"; Nephrol Dial Transplant. 27(1); pp. 174-181.
ASBMB Today (2021) "A mechanism of liver disease treatment" *The Member Magazine Of The American Society For Biochemistry And Molecular Biology*, 1 page.
Cal, et al (2008) "Use of cyclodextrins in topical formulations: practical aspects"; Eur J Pharm Biopharm 68(3); pp. 467-478.
Albert Eschenmoser, et al., Enhanced Reactivity in Dioxirane C—H Oxidations via Strain Release, *J. Org. Chem.*, 2013, 78, 4037-4048.
ClinicalTrials.gov: NCT04563026; "A Phase 2b Study in Subjects With Alcoholic Hepatitis to Evaluate Safety andEfficacy of DUR-928 Treatment (AHFIRM)"; Study Details; Durect Corporation; Sep. 24, 2020; 8 pages.
Craig, et al (2010) "Systematic review: prognostic tests of paracetamol-induced acute liver failure"; Aliment Pharmacol Ther 31(10); pp. 1064-1076.

Durect (2015) "Durect Announces Epigenomic Regulator Program including a New NAFLD/NASH and Acute Organ Injury Product Candidate in Development"; News Release, Mar. 2, 2015; 4 pages.
Durect (2015) "Durect Announces Positive Results from DUR-928 Multi-Dose Phase 1 Study"; News Release, May 18, 2015; 4 pages.
Durect (2016) "Durect Announces Positive Phase 1 Data for DUR-928"; News Release, Jan. 6, 2016; 3 pages.
Durect (2016) "Durect Corporation Announces Update on DUR-928 Development Program"; News Release, Oct. 31, 2016; 5 pages.
Durect (2017) "Durect Corporation Announces Update on DUR-928 Development Program"; News Release, Jan. 30, 2017; 4 pages.
Durect (2018) "Durect Announces Amendment to Accelerate Ongoing Phase 2a Trial of DUR-928 in Alcoholic Hepatitis (AH) by Allowing Dosing of Severe AH Patients in Parallel to Moderate AH Patients" News Release, Nov. 19, 2018; 4 pages.
Durect (2018) "Durect Announces Patient Dosing in Phase 2a Trial ofDUR-928 in Alcoholic Hepatitis"; News Release, Apr. 25, 2018; 3 pages.
Durect (2019) "Durect Announces Positive Data from its Phase 2a Clinical Trial of DUR-928 in Alcoholic Hepatitis"; News Release, Sep. 17, 2019; 3 pages.
Durect (2019) "Durect Corporation Announces Preliminary Data from the Ongoing DUR-928 Alcoholic Hepatitis Phase 2a Trial"; News Release, May 7, 2019; 6 pages.
Durect (2020) "Durect Corporation Announces Positive Topline Data from Phase 1b Study of DUR-928 in NASH"; News Release, May 26, 2020; 6 pages.
Durect (2020) "Durect Corporation Announces Top-Line Results from Phase 2a Clinical Trial in Patients with Psoriasis"; News Release, Jan. 2, 2020; 3 pages.
English Translation of Japanese Office Action dated Jul. 23, 2019 for Japanese Patent Application No. 2017-518508.
Lawitz et al., "Efficacy Signals of 4-Week Oral DUR-928 in NASH Subjects;" ePoster at EASL the International Liver Congress; Jun. 23, 2021.
Lawitz et al., "Safety and Efficacy Signals of Daily Oral DUR-928 for 4-Weeks in F1-F3 NASH;" ePoster at AASLD The Liver Meeting; Nov. 13, 2020.
Marlowe et al., Prevalence, Co-Morbidities and In-Hospital Mortality of Hospitalized Alcohol-Associated Hepatitis in US in 2015-2018. AASLD The Liver Meeting®; Nov. 12-15, 2021.
Ren, "Oxysterol Sulfation as Regulatory Signaling Pathway"; McGuire VA Medical CenterNirginia Commonwealth University; (Apr. 2014) 1 page.
Ren, "Sulfation of 25-Hydroxycholesterol Regulates Lipid Metabolism and Inflammatory Responses in Human Aortic Endothelial Cells, Macrophages, and Hepatocytes"; Abstract; Departments of Medicine, McGuire Veterans Affairs Medical CenterNirginia Commonwealth University; (Jan. 2014) 1 page.
Shah et al., "Pharmacokinetics of DUR-928 in Alcoholic Hepatitis Patients—A Phase 2a Study;" ePoster at EASL The European Association for the Study of the Liver; Aug. 27, 2020.
Shah et al., "Safety and Pharmacokinetics of DUR-928 in Hepatic Function Impaired Subjects," ePoster at EASL the International Liver Congress; Jun. 23, 2021.
Wang and Ren "25-Hydroxycholesterol is a Potent Epigenetic Regulator: High Glucose Induces Lipid Accumulation via 25-Hydroxycholesterol DNA-CpG Methylation in Human Hepatocytes"; Department of Internal Medicine, Virginia Commonwealth University/ McGuire VA Medical Centre; AASLD Annual Meeting, Nov. 13-16, 2020, 1 page.
Wang et al. (2021) "25-Hydroxycholesterol 3-sulfate is an endogenous ligand of DNA methyltransferases in hepatocytes"; Journal of Lipid Research. 2021; 62: 100063.
Wang, et al (2021) "25-Hydroxycholesterol 3-Sulfate Recovers Acetaminophen Induced Acute Liver Injury via Stabilizing Mitochondria in Mouse Models" ; Cells 10, 3027; pp. 1-17.
You, et al (2002) "Ethanol Induces Fatty Acid Synthesis Pathways by Activation of Sterol Regulatory Element-binding Protein (SREBP)"; The Journal Of Biological Chemistry, vol. 277, No. 32, pp. 29342-29347.

(56) References Cited

OTHER PUBLICATIONS

Li, et al (2007) "Discovery of a novel regulatory pathway in cholesterol metabolism"; *The FASEB Journal* 21(5); Abstract; 1 page https://doi.org/10.1096/fasebj.21.5.A239-a.

Li, et al (2008) "25-Hydroxycholesterol 3-sulfate regulates lipid metabolism via SREBP-1 in human macrophages"; *The FASEB Journal* 22(S1); Abstract; 1 page. https://doi.org/10.1096/fasebj.22.1_supplement.807.6.

Ma, et al (2009) "Inhibition of cellular lipid biosynthesis by sulfated oxysterol is mediated via the LXR pathway"; *The FASEB Journal* 23(S1); Abstract; 1 page. https://doi.org/10.1096/fasebj.23.1_supplement.522.1.

Ren, et al (2007) "The Nuclear Oxysterol, 5-Cholesten-3β, 25-Diol 3-Sulfate, Decreases Cholesterol Biosynthesis by Inhibiting Expression of HMG CoA Reductase in HepG2 Cells"; *The FASEB Journal* 21(5); Abstract; 1 page. https://doi.org/10.1096/fasebj.21.5.A454-c.

Xu, et al (2009) "Nuclear Oxysterols, 25HC and 25HC3S, Regulate Nuclear Orphan Receptor Activities and Attenuate Intracellular Lipid Levels"; *The FASEB Journal* 23(S1); Abstract; 1 page. https://doi.org/10.1096/fasebj.23.1_supplement.871.1.

Argemi et al. (2019) "Defective HNF4alpha-dependent gene expression as a driver of hepatocellular failure in alcoholic hepatitis"; *Nature Communications*, 10 (3126); pp. 1-19.

Arora, et al (2011) "Acute renal dysfunction in patients with alcoholic hepatitis"; *World J Hepatol* 3(5): pp. 121-124.

Bai, et al (2011) "In Vivo Overexpression of Hydroxysteroid Sulfotransferase SULT2B1b in Mice Reduces Hepatic Lipids and Suppresses SREBP Signaling: Further Evidence for Oxysterol Sulfates as Endogenous Regulators of Hepatic Lipid Metabolism"; *Gastroenterology* 140(5); abstract; 1 page.

Bi, et al (2018) "Regulation of Cholesterol Sulfotransferase SULT2B1b by Hepatocyte Nuclear Factor 4α Constitutes a Negative Feedback Control of Hepatic Gluconeogenesis"; Molecular and Cellular Biology, vol. 38 Issue 7; pp. 1-15.

Clinicaltrials.gov: NCT04447404; DUR-928 in Subjects With SARS-CoV-2 With Acute Lung, Liver or Kidney Injury; Study Results; Durect Corporation; Aug. 5, 2022; 9 pages.

ClinicalTrials.gov: NCT04563026; "A Phase 2b Study in Subjects with Alcoholic Hepatitis to Evaluate Safety and Efficacy of DUR-928 Treatment (AHFIRM)"; Tabular View; Durect Corporation; Sep. 24, 2020; 8 pages.

Clinicaltrials.gov: NCT04563026; A Phase 2b Study in Subjects with Alcoholic Hepatitis to Evaluate Safety and Efficacy of DUR-928 Treatment (AHFIRM); Full Text View; Durect Corporation; (update) Aug. 10, 2022; 7 pages.

Crabb et al (2020) "Diagnosis and Treatment of Alcohol-Associated Liver Diseases: 2019 Practice Guidance From the American Association for the Study of Liver Diseases"; *Hepatology*, vol. 71, No. 1; pp. 306-333.

Drinane and Shah (2013) "Alcoholic Hepatitis: Diagnosis and Prognosis"; *Clinical Liver Disease*, vol. 2, No. 2; pp. 80-83.

Gustot, et al (2017) "Sepsis in alcohol-related liver disease"; *Journal of Hepatology* vol. 67; pp. 1031-1050.

Hughes, et al (2018) "Survival from alcoholic hepatitis has not improved over time"; PLOS One; pp. 1-10.

Kakiyama, et al (2011) "Characterization of Oxysterols and Their Sulfates in Primary Rat Hepatocytes (Prh) Following Increased Expression of the Mitochondrial Cholesterol Delivery Protein, StarD1"; *Gastroenterology* 140(5); Abstract; 1 page.

Marlowe et al (2022) "Prevalence, co-morbidities, and in-hospital mortality of patients hospitalized with alcohol-associated hepatitis in the United States from 2015 to 2019"; *Alcohol Clin Exp Res.*; pp. 1-10.

Ning, et al (2009) "Overexpression of mitochondrial cholesterol delivery protein, StAR, decreases intracellular lipids and inflammatory factors secretion in macrophages"; *Atherosclerosis*. 204(1): pp. 114-120.

Ning, et al (2009) "StAR overexpression decreases serum and tissue lipids in apolipoprotein E-deficient mice"; *Lipids* 44(6); pp. 511-519.

Owens, et al (2016) "Pharmacologic Treatment of Alcoholic Hepatitis: Examining Outcomes Based on Disease Severity Stratification"; *Journal of Clinical and Experimental Hepatology*, vol. 6, No. 4; pp. 275-281.

Ren, et al (2010) "Is 25-Hydroxycholesterol 3Sulfate an Endogenous Ligand of Ppargamma?"; *Gastroenterology* 138(5); Abstract; 1 page.

Ren, et al (2011) "In vivo Oxysterol Sulfation by SULT2B1b Reduces Hepatic Lipid Accumulation and Suppresses SREBP-1c Signaling: Evidence for the Sulfation as a Regulatory Pathway in Lipid Metabolism"; *Departments of Medicine, Virginia Commonwealth University/McGuire Veterans Affairs Medical Center*; poster; 1 page.

Ren, Shunlin; "A Novel Regulatory Pathway: Oxysterol Sulfation in Lipid Metabolism and Inflammatory Responses"; Presentation (Nov. 2011); pp. 1-63.

Ren et al. (2018) "Novel oxysterol sulfates alleviate injured liver function and decrease mortality in LPS-induced mouse model," *J Clin Gastroenterol Hepatol* vol. 2; 1 page.

Ren, et al (2021) "Oxysterol Sulfation"; Encyclopedia Publication; 13 pages.

Shen, et al (2011) "25-Hydroxycholesterol-3Sulfate (25HC3S): A Physiological Ligand of PPARγ?"; *Gastroenterology* 140(5); Abstract; 1 page.

Shukla, et al (2013) "Epigenetic Effects of Ethanol on theLiver and Gastrointestinal System"; *Alcohol Research: Current Reviews*; pp. 47-56.

Thompson, et al (2018) "Mortality and costs associated with alcoholic hepatitis: A claims analysis of a commercially insured population"; *Alcohol* 71; pp. 57-63.

Thursz, et al. (2015) "Prednisolone or Pentoxifylline for Alcoholic Hepatitis" N Engl J 372(17); pp. 1619-1628.

Tornai and Szabo (2020) "Emerging medical therapies for severe alcoholic hepatitis"; *Clinical and Molecular Hepatology* 26; pp. 686-696.

Wang, et al (2021) "Cholesterol Metabolites 25-Hydroxycholesterol and 25-Hydroxycholesterol 3-Sulfate Are Potent Paired Regulators: From Discovery to Clinical Usage"; *Metabolites* 11(1); pp. 2-14.

Yang, et al (2019) "Bindings of PPARγ ligand-binding domain with 5-cholesten-3β, 25-diol, 3-sulfate: accurate prediction by molecular simulation"; *Journal of Biomolecular Structure and Dynamics*; pp. 1-9.

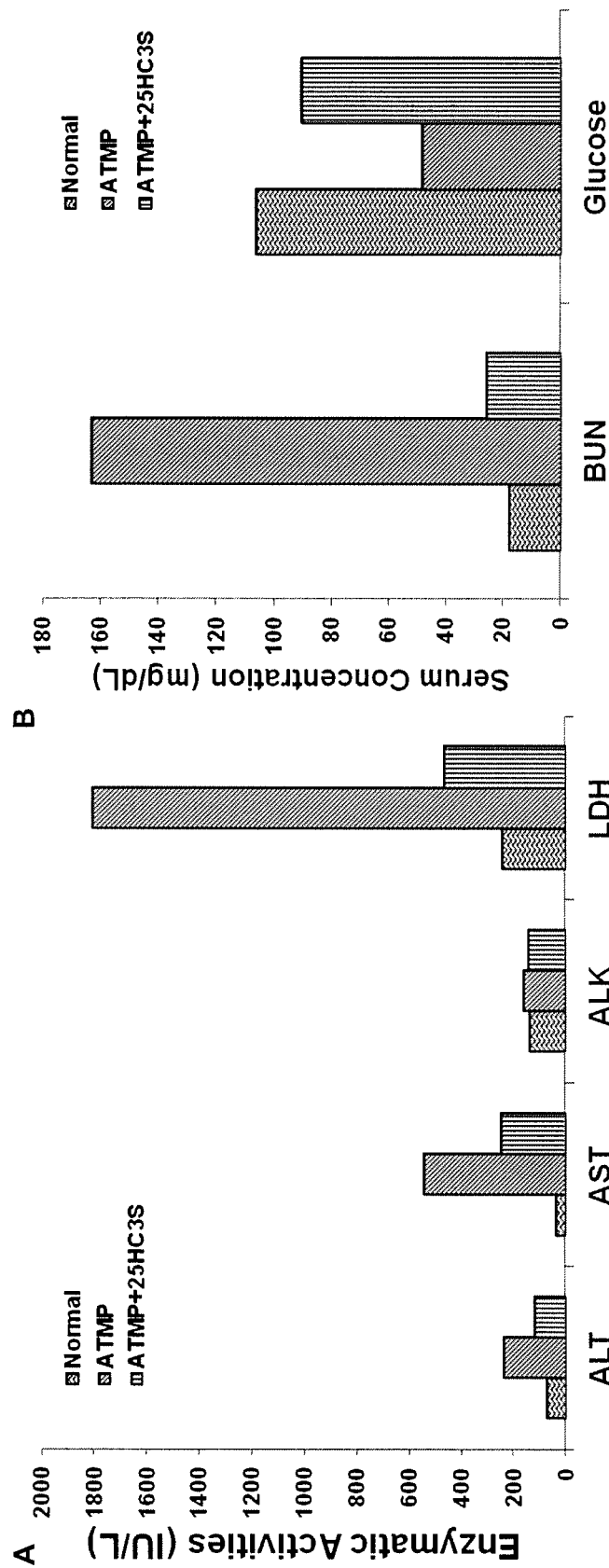
Figure 2A and B

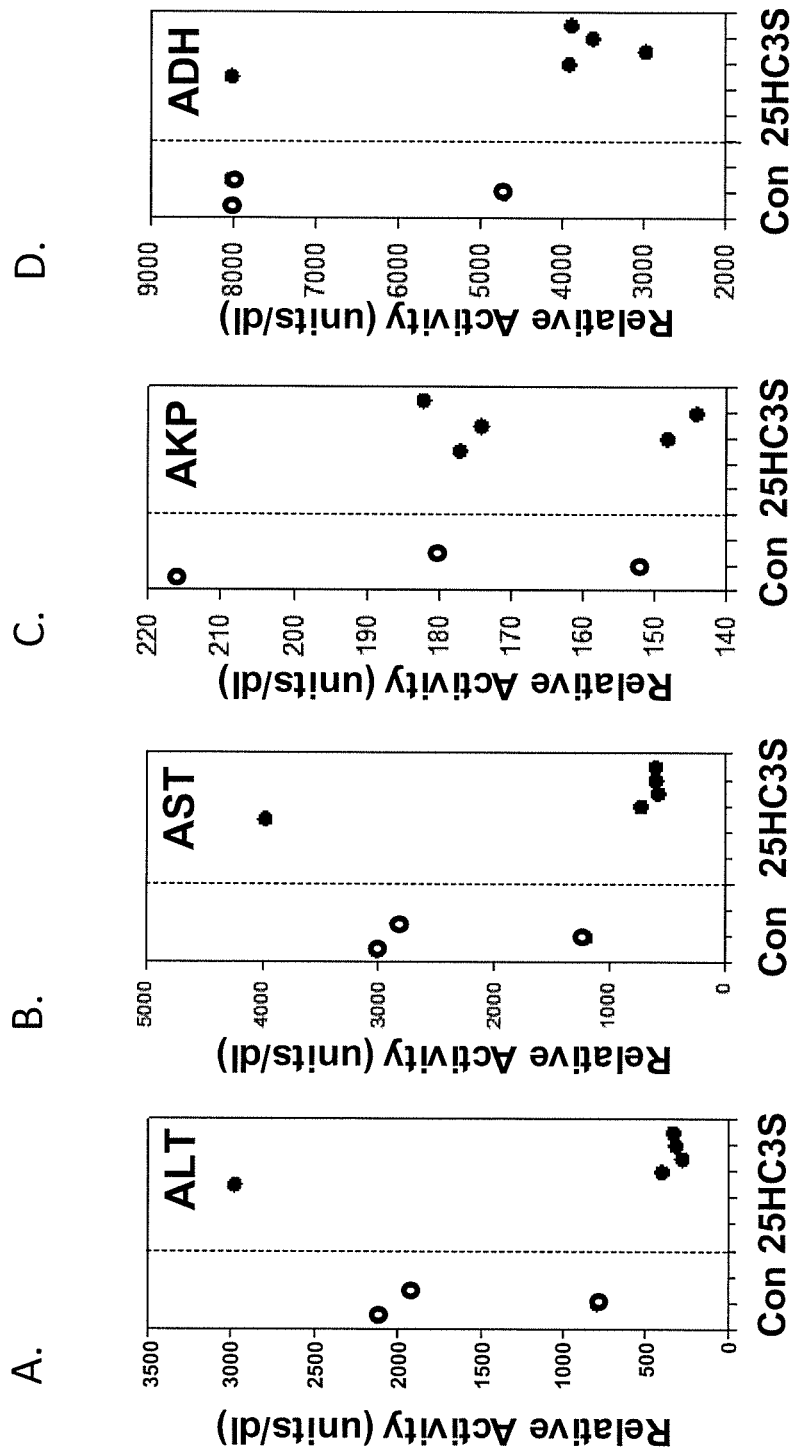
Figure 5A-D

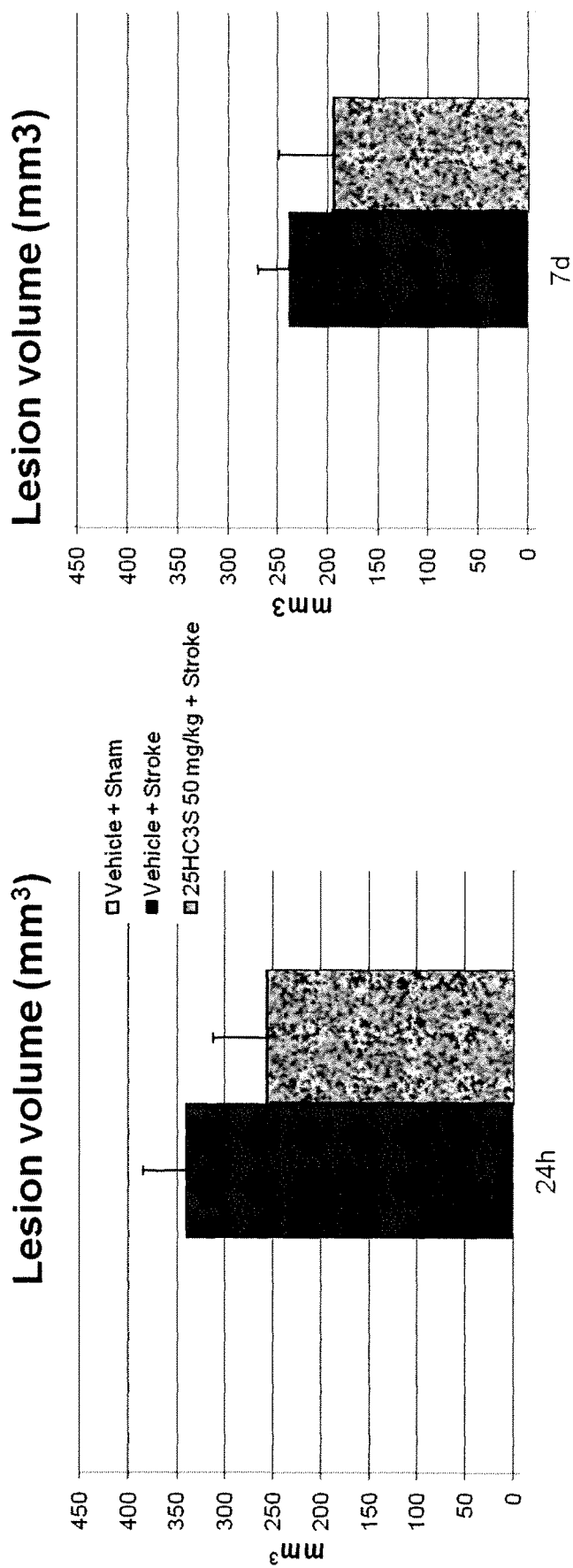
Figure 8D and E

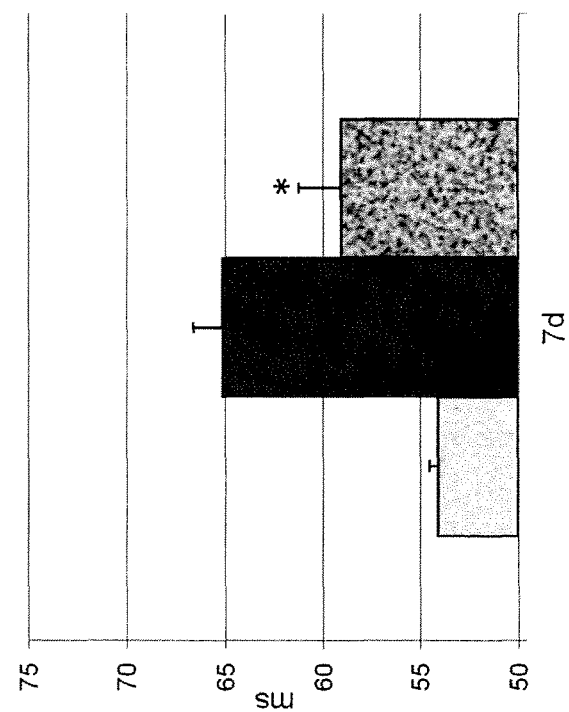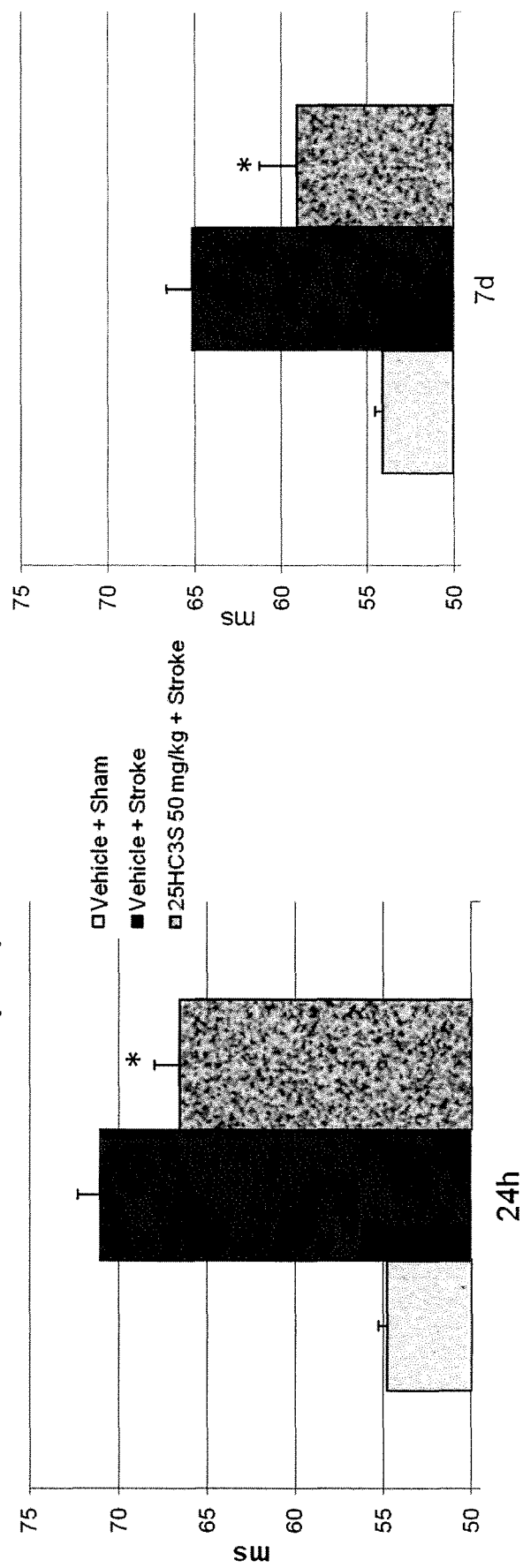
Figure 8J and K

USES OF OXYGENATED CHOLESTEROL SULFATES (OCS)

CROSS-REFERENCE TO RELATED APPLICATION

The present application is a continuation of U.S. patent application Ser. No. 16/368,553 filed Mar. 28, 2019, now U.S. Pat. No. 10,786,517 which is a continuation of U.S. patent application Ser. No. 15/016,883 filed Jun. 21, 2016, now U.S. Pat. No. 10,272,097, which is a 371 of International Patent Application No. PCT/US2014/072128 filed Dec. 23, 2014 which claims priority benefit to U.S. Provisional Application No. 61/920,617, filed Dec. 24, 2013, the applications of which are incorporated herein by reference in their entirety.

FIELD OF THE INVENTION

The present disclosure generally relates to the prevention and/or treatment of ischemia, organ dysfunction and/or organ failure, and necrosis and/or apoptosis associated with organ dysfunction/failure. For instance, the present disclosure provides compositions and methods to prevent/treat dysfunction and/or failure of an organ by contacting the organ with one or more oxygenated cholesterol sulfates (OCS). The organ may be in vivo or ex vivo.

INTRODUCTION

Necrosis is a form of cell injury that results in the premature death of cells in living tissue by autolysis. Necrosis is caused by factors external to the cell or tissue, such as infection, toxins, or trauma, which result in the unregulated digestion of cell components. In contrast, apoptosis is a naturally occurring programmed and targeted cause of cellular death. While apoptosis often provides beneficial effects to the organism, necrosis is almost always detrimental and can be fatal. In some instances, the two are associated in that necrotic cells release factors that elicit apoptosis in surrounding cells and tissues.

Cells that die due to necrosis do not follow the apoptotic signal transduction pathway but rather various receptors are activated that result in the loss of cell membrane integrity and an uncontrolled release of products of cell death into the intracellular space. This initiates in the surrounding tissue an inflammatory response which prevents nearby phagocytes from locating and eliminating the dead cells by phagocytosis. For this reason, it is often necessary to remove necrotic tissue surgically, a procedure known as debridement. Untreated necrosis results in a build-up of decomposing dead tissue and cell debris at or near the site of the cell death. A classic example is gangrene.

Organ dysfunction is a condition in which an organ does not perform its expected, desired or usual function. Organ failure is organ dysfunction to such a degree that normal homeostasis cannot be maintained without external clinical intervention. These two conditions occur on a continuum of incremental degrees of physiologic derangement and vary widely from a mild degree of organ dysfunction to completely irreversible organ failure. Organ dysfunction and failure may be acute, developing rapidly (e.g. as a result of acute insult such as a bacterial infection, severe burns, etc), or may be chronic, developing over a long period or time (e.g. as a result of long-term exposure to an organ-toxic medication). Multiple organ dysfunction syndrome (MODS, previously known as multiple organ failure (MOF) or multisystem organ failure (MSOF)), refers to the failure of two or more organs or organ systems at the same time, for example, the cardiovascular and renal systems. In some cases, a single etiological agent or event can be identified as initiating the disease process but this is not always the case; dysfunction and failure may be caused by multiple factors and/or the causative agent(s) may never be identified. A frequent proximal cause is ischemia followed by inflammation and necrosis.

Organ dysfunction and failure have major clinical and economic impacts. The cost of clinical intervention is extremely high and typically involves intensive life support measures for both acute and chronic disease. In general, mortality ranges from about 30% to about 100% and has not changed significantly since the 1980s. The chance of survival diminishes as the number of organs involved increases, especially if cardiovascular dysfunction is involved. For patients that do survive, a full recovery of normal function may not occur for many years, or may not ever occur.

At present there is no agent available that can reverse established organ failure and therapy is limited to treating the root cause, if known, and supportive care such as safeguarding hemodynamics, fluid levels, pH balance and respiration.

One possible treatment for severe organ failure is the transplantation of an organ from a donor. However, organs that are harvested for transplant can also suffer from dysfunction due to ischemia fluid loss, pH changes, ketoacidosis and other problems associated with removal from the donor and exposure to the ex vivo environment during transport and storage. For instance, high levels of inflammatory cytokines may be present in organs prior to transplant and may cause damage during transport and storage. Even though care may be taken to preserve organ function e.g. by bathing the organ in a specialized fluid during transportation, the preservation of viability is still a major challenge, and alternative and/or improved agents that can maintain the viability of harvested organs are needed. It would be especially advantageous to have available an agent that is fully biologically compatible with donated organs and the bodies of transplant recipients.

There is an urgent need for agents and methods to prevent and treat the dysfunction and/or failure of organs and organ systems, including prevention and treatment of underlying causes and/or symptoms of organ dysfunction and failure, such as sepsis, ischemia, unwanted inflammation and cell death.

SUMMARY

The present disclosure provides a variety of uses for oxygenated cholesterol sulfates (OCS), including methods of preventing and/or treating ischemia (e.g., from surgery), necrosis, apoptosis, organ dysfunction, and/or organ failure for in vivo and ex vivo organs. The methods include contacting an organ of interest with at least one oxygenated cholesterol sulfate (OCS). If the organ of interest is within a patient (in vivo), then contact generally involves administering to a patient harboring the organ an amount of at least one OCS that is effective or sufficient to prevent and/or treat dysfunction and/or failure of the organ. Advantageously, the at least one OCS has been found to be highly bioavailable, even when administered orally. If the organ has already been harvested from a subject (i.e. from a donor), and/or is being prepared for harvest from a donor, then contact generally involves applying at least one OCS to the organ.

In addition, the present disclosure provides methods of preventing and/or treating diseases and conditions which lead to and/or cause, or are otherwise associated with, organ dysfunction/failure in a patient in need thereof, by administering to the patient an amount of at least one OCS that is effective or sufficient to prevent and/or treat the disease or condition.

Aspects of the disclosure provide methods of prophylactically treating or treating ischemia caused by surgery in a subject in need thereof, comprising administering to the subject an amount of 5-cholesten-3,25-diol, 3-sulfate (25HC3S) that is sufficient to prophylactically treat or treat ischemia. In some aspects, the ischemia comprises at least one member selected from cardiac ischemia, brain ischemia, bowel ischemia, limb ischemia, and cutaneous ischemia. In other aspects, the prophylactically treating or treating ischemia comprises reducing one or more of inflammation, tissue necrosis, organ necrosis, risk of stroke, and reperfusion injury in the subject. In additional aspects, the surgery comprises at least one of cardiovascular surgery, heart surgery, and aneurysm surgery. In further aspects, the 25HC3S is administered for not more than seven days prior to surgery, for example on at least a daily basis starting not more than seven days prior to the surgery. In other aspects, the 25HC3S is administered during the surgery. In yet other aspects, the 25HC3S is administered for not more than seven days after the surgery, for example on at least a daily basis for not more than seven days after the surgery. In some aspects, the surgery is not liver surgery. In other aspects, the surgery is not a transplant surgery.

Aspects of the disclosure also provide methods of preventing or treating dysfunction or failure of one or more organs or organ systems in a subject in need thereof, comprising administering to the subject an amount of 5-cholesten-3,25-diol, 3-sulfate (25HC3S) that is sufficient to prevent or treat the dysfunction or failure of the organ or organ system, wherein if the one or more organs comprises a liver, the administering occurs for not more than 14 days (2 weeks). In some aspects, the one or more organs comprises at least one member selected from the liver, the kidney, the heart, the brain, and the pancreas. In additional aspects, the dysfunction or failure is caused by acetaminophen (ATMP). In further aspects, the 25HC3S is administered within one week of administration of the ATMP. In yet other aspects, the dysfunction or failure is Multiple Organ Dysfunction Syndrome (MODS).

Further aspects of the disclosure provide methods of transplanting one of more cells, organs or tissues comprising i) removing the one or more of cells, organs or tissues from a donor, ii) contacting the one or more of cells, organs or tissues with an amount of 5-cholesten-3,25-diol, 3-sulfate (25HC3S) that is sufficient to preserve the one of more cells, organs or tissues; and iii) transplanting the one or more of cells, organs or tissues into a recipient. In further aspects, the one or more of cells, organs or tissues is not a liver cell, a liver organ or liver tissue.

Additional aspects of the disclosure provide methods of preserving an ex vivo cell, organ or tissue, comprising contacting the ex vivo cell, organ or tissue, with an amount of 5-cholesten-3,25-diol, 3-sulfate (25HC3S) that is sufficient to preserve the cell, organ or tissue.

Further aspects of the disclosure provide methods of preventing or treating acute liver failure and/or kidney failure in a subject in need thereof, comprising administering to the subject an amount of 5-cholesten-3,25-diol, 3-sulfate (25HC3S) that is effective in preventing or treating the acute liver failure and/or kidney failure; wherein the acute liver failure and/or kidney failure is caused by acetaminophen (ATMP).

Further aspects of the disclosure:

1. A method of preventing the death of an ex vivo cell, comprising contacting the ex vivo cell with an amount of 5-cholesten-3, 25-diol, 3-sulfate (25HC3S) that is sufficient to prevent the death of the cell.

2. The method of 1, wherein the cell is undergoing apoptosis or necrosis.

3. A method of preventing the death of a cell in a patient, comprising administering to the subject an amount of 5-cholesten-3, 25-diol, 3-sulfate (25HC3S) that is sufficient to prevent the death of the cell.

4. The method of 3, wherein the cell is undergoing apoptosis or necrosis.

5. A method of prophylactically treating or treating ischemia in a subject in need thereof, comprising administering to the subject an amount of 5-cholesten-3, 25-diol, 3-sulfate (25HC3S) that is sufficient to prophylactically treat or treat ischemia.

6. The method of 5, wherein the ischemia comprises at least one member selected from cardiac ischemia, brain ischemia, bowel ischemia, limb ischemia, and cutaneous ischemia.

7. The method of 5 or 6, wherein the prophylactically treating or treating comprises reducing at least one of inflammation, tissue necrosis, organ necrosis, stroke, and reperfusion injury in the subject.

8. The method of any one of 5 to 7, wherein the ischemia is caused by surgery.

9. The method of 8, wherein the surgery comprises at least one of cardiovascular surgery, heart surgery, and aneurysm surgery.

10. The method of 8 or 9, wherein the 25HC3S is administered for not more than seven days prior to the surgery.

11. The method of any one of 8 to 10, wherein the 25HC3S is administered during the surgery.

12. The method of any one of 8 to 11, wherein the 25HC3S is administered for not more than seven days after the surgery.

13. The method of any one of 8 to 12, wherein the surgery is not liver surgery.

14. The method of any one of 8 to 13, wherein the surgery is not a transplant surgery.

15. The method of any one of 5 to 14, wherein the 25HC3S is administered to the subject at a dose ranging from about 0.001 mg/kg/day to about 100 mg/kg/day.

16. A method of prophylactically treating or treating ischemia caused by surgery in a subject in need thereof, comprising
  administering to the subject an amount of 5-cholesten-3, 25-diol, 3-sulfate (25HC3S) that is sufficient to prophylactically treat or treat ischemia.

17. The method of 16, wherein the ischemia comprises at least one member selected from cardiac ischemia, brain ischemia, bowel ischemia, limb ischemia, and cutaneous ischemia.

18. The method of 16 or 17, wherein the prophylactically treating or treating comprises reduction in one or more of inflammation, tissue necrosis, organ necrosis, risk of stroke, and reperfusion injury in the subject.

19. The method of any one of 16 to 18, wherein the surgery comprises at least one of cardiovascular surgery, heart surgery, and aneurysm surgery.

20. The method of any one of 16 to 19, wherein the 25HC3S is administered for not more than seven days prior to the surgery.

21. The method of any one of 16 to 20, wherein the 25HC3S is administered during the surgery.

22. The method of any one of 16 to 21, wherein the 25HC3S is administered for not more than seven days after the surgery.

23. The method of any one of 16 to 22, wherein the surgery is not liver surgery.

24. The method of any one of 16 to 23, wherein the surgery is not a transplant surgery.

25. The method of any one of 16 to 24, wherein the 25HC3S is administered to the subject at a dose ranging from about 0.001 mg/kg/day to about 100 mg/kg/day.

26. A method of preventing or treating necrosis of cells, tissues and/or organs in a subject in need thereof, comprising
administering to the subject an amount of 5-cholesten-3, 25-diol, 3-sulfate (25HC3S) that is sufficient to prevent or treat the necrosis of cells, tissues and/or organs.

27. The method of 26, wherein the cells, tissues and/or organs comprise at least one member selected from the liver, the kidney, the heart, the brain, and the pancreas.

28. A method of preventing the spread of necrosis within a tissue or organ comprising necrotic cells, comprising
administering to the tissue or organ an amount of 5-cholesten-3, 25-diol, 3-sulfate (25HC3S) that is sufficient to prevent the spread of necrosis within the tissue or organ.

29. A method of preventing apoptosis of a cell, comprising
contacting the cell with an amount of 5-cholesten-3, 25-diol, 3-sulfate (25HC3S) that is effective in preventing apoptosis of the cell.

30. A method of minimizing apoptosis of cells in a tissue or organ, comprising
contacting the cells with an amount of 5-cholesten-3, 25-diol, 3-sulfate (25HC3S) that is sufficient to minimize apoptosis of the cells in the tissue or organ.

31. A method of preventing or treating dysfunction or failure of one or more organs or organ systems in a subject in need thereof, comprising
administering to the subject an amount of 5-cholesten-3, 25-diol, 3-sulfate (25HC3S) that is sufficient to prevent or treat the dysfunction or failure of the organ or organ system,
wherein if the one or more organs comprises a liver, the administering occurs for not more than 14 days.

32. The method of 31, wherein the one or more organs comprises at least one member selected from the liver, the kidney, the heart, the brain, and the pancreas.

33. The method of 31 or 32, wherein the dysfunction or failure is caused by acetaminophen (ATMP).

34. The method of 33, wherein the 25HC3S is administered within one week of administration of the ATMP.

35. The method of any one of 31 to 34, wherein the dysfunction or failure is Multiple Organ Dysfunction Syndrome (MODS).

36. The method any one of 31 to 35, wherein the 25HC3S is administered at a dose ranging from about 0.001 mg/kg/day to about 100 mg/kg/day.

37. A method of preventing or treating acute liver failure and/or acute kidney failure in a subject in need thereof, comprising
administering to the subject an amount of 5-cholesten-3, 25-diol, 3-sulfate (25HC3S) that is effective in preventing or treating the acute liver failure and/or kidney failure.

38. The method of 37, wherein the acute liver failure and/or acute kidney failure is caused by acetaminophen (ATMP).

39. The method of 37 or 38, wherein the 25HC3S is administered within one day of onset of the acute liver failure and/or acute kidney failure.

40. The method of any one of 37 to 39, wherein the 25HC3S is administered for up to 2 weeks after diagnosis of the acute liver failure and/or acute kidney failure.

41. The method of any one of 37 to 40, wherein the 25HC3S is administered to the subject at a dose ranging from about 0.001 mg/kg/day to about 100 mg/kg/day.

42. A method of decreasing a risk of mortality in a subject experiencing or at risk of experiencing dysfunction or failure of an organ or organ system, comprising
administering to the subject an amount of 5-cholesten-3, 25-diol, 3-sulfate (25HC3S) that is sufficient to decrease the risk of mortality.

43. A method of preserving an ex vivo cell, organ or tissue, comprising
contacting the ex vivo cell, organ or tissue, with an amount of 5-cholesten -3, 25-diol, 3-sulfate (25HC3S) that is sufficient to preserve the cell, organ or tissue.

44. A method of transplanting one of more cells, organs or tissues comprising
removing the one or more of cells, organs or tissues from a donor,
contacting the one or more of cells, organs or tissues with an amount of 5-cholesten-3, 25-diol, 3-sulfate (25HC3S) that is sufficient to preserve the one of more cells, organs or tissues; and
transplanting the one or more of cells, organs or tissues into a recipient.

45. The method of 44, wherein the one or more of cells, organs or tissues is not a liver cell, a liver organ or liver tissue.

46. A composition comprising
an ex vivo cell, organ or tissue and
5-cholesten-3, 25-diol, 3-sulfate (25HC3S).

47. The composition of 46, further comprising an oxygenated physiologically compatible carrier medium.

48. A composition comprising:
an active agent comprising at least one member selected from ibuprofen, aspirin, and acetaminophen; and
5-cholesten-3, 25-diol, 3-sulfate (25HC3S).

49. A method of prophylactically treating or treating sepsis in a subject in need thereof, comprising
administering to the subject an amount of 5-cholesten-3, 25-diol, 3-sulfate (25HC3S) that is sufficient to prophylactically treat or treat the sepsis.

50. The method of 49, wherein the prophylactically treating or treating sepsis comprises prophylactically treating or treating damage associated with sepsis, wherein the damage is optionally dysfunction or failure of one or more organs.

51. The method of 50, wherein the one or more organs comprises at least one member selected from the liver, the kidney, the heart, the brain, and the pancreas.

52. A method of preventing or treating necrosis and/or apoptosis associated with necrosis of cells or tissue in a subject in need thereof, comprising
administering to the subject an amount of one or both of 5-cholesten-3, 25-diol, 3-sulfate (25HC3S) and 5-cholesten 3, 25-diol, disulfate (25HCDS) that is effective in preventing or treating the necrosis and/or apoptosis.

53. The method of 52, wherein the tissue is liver tissue and/or kidney tissue.

54. The method of 53, wherein the necrosis is caused by acetaminophen (ATMP).

55. A method of preventing or treating acute liver failure and/or kidney failure in a subject in need thereof, comprising administering to the subject an amount of one or both of 5-cholesten-3, 25-diol, 3-sulfate (25HC3S) and 5-cholesten 3, 25-diol, disulfate (25HCDS) that is effective in preventing or treating the acute liver failure and/or kidney failure.

56. The method of 55, wherein the acute liver failure and/or kidney failure is caused by acetaminophen (ATMP).

57. The method of any of 3, 4, 26 to 28, 42, and 49 to 56, wherein the 25HC3S is administered at a dose ranging from about 0.001 mg/kg/day to about 100 mg/kg/day.

58. The method of any of 3 to 28, 31 to 42, and 49 to 57, wherein the administering is performed orally or by injection.

59. The method of any of 3 to 28, 31 to 42, and 49 to 57, wherein the administering is performed from once to 3 times per day.

60. 5-cholesten-3, 25-diol, 3-sulfate (25HC3S) for use in a method of medical treatment that comprises preventing the death of a cell.

61. A method of preventing the death of a cell ex vivo, comprising
   contacting the cell with a an amount of 5-cholesten-3, 25-diol, 3-sulfate (25HC3S) that is sufficient to prevent the death of the cell.

62. 5-cholesten-3, 25-diol, 3-sulfate (25HC3S) for use in a method of prophylactically treating or treating ischemia.

63. 5-cholesten-3, 25-diol, 3-sulfate (25HC3S) for use in a method of prophylactically treating or treating ischemia caused by surgery.

64. 5-cholesten-3, 25-diol, 3-sulfate (25HC3S) for use in a method of preventing or treating necrosis of cells, tissues and/or organs in a subject in need thereof.

65. 5-cholesten-3, 25-diol, 3-sulfate (25HC3S) for use in a method of medical treatment that comprises preventing the spread of necrosis within a tissue or organ comprising necrotic cells.

66. 5-cholesten-3, 25-diol, 3-sulfate (25HC3S) for use in a method of medical treatment that comprises preventing apoptosis of a cell.

67. 5-cholesten-3, 25-diol, 3-sulfate (25HC3S) for use in a method of medical treatment that comprises minimizing apoptosis of cells in a tissue or organ.

68. 5-cholesten-3, 25-diol, 3-sulfate (25HC3S) for use in a method of preventing or treating dysfunction or failure of one or more organs or organ systems in a subject in need thereof, wherein if the one or more organs comprises a liver the method comprises administering the 5-cholesten-3, 25-diol, 3-sulfate (25HC3S) for no more than 14 days.

69. 5-cholesten-3, 25-diol, 3-sulfate (25HC3S) for use in a method of preventing or treating acute liver failure and/or acute kidney failure in a subject in need thereof.

70. 5-cholesten-3, 25-diol, 3-sulfate (25HC3S) for use of 67, wherein the acute liver failure and/or acute kidney failure is caused by acetaminophen (ATMP).

71. 5-cholesten-3, 25-diol, 3-sulfate (25HC3S) for use in a method of decreasing a risk of mortality in a subject experiencing or at risk of experiencing dysfunction or failure of an organ or organ system.

72. 5-cholesten-3, 25-diol, 3-sulfate (25HC3S) for use in a method of treatment comprising: removing, optionally by surgery, one or more of cells, organs or tissues from a donor; and contacting, ex vivo, the one or more cells, organs or tissues with an amount of 5-cholesten-3, 25-diol, 3-sulfate (25HC3S) that is sufficient to preserve the one of more cells, organs or tissues.

73. 5-cholesten-3, 25-diol, 3-sulfate (25HC3S) for use in a method of treatment comprising: contacting, ex vivo, one or more of cells, organs or tissues with an amount of 5-cholesten-3, 25-diol, 3-sulfate (25HC3S) that is sufficient to preserve the one of more cells, organs or tissues; and transplanting, optionally by surgery, the one or more of cells, organs or tissues into a recipient.

74. 5-cholesten-3, 25-diol, 3-sulfate (25HC3S) for use in a method of treatment comprising: removing, optionally by surgery, one or more of cells, organs or tissues from a donor; contacting, ex vivo, the one or more of cells, organs or tissues with an amount of 5-cholesten-3, 25-diol, 3-sulfate (25HC3S) that is sufficient to preserve the one of more cells, organs or tissues; and transplanting, optionally by surgery, the one or more of cells, organs or tissues into a recipient.

75. 5-cholesten-3, 25-diol, 3-sulfate (25HC3S) for use in a method of prophylactically treating or treating sepsis.

76. 5-cholesten-3, 25-diol, 3-sulfate (25HC3S) and/or 5-cholesten 3, 25-diol, disulfate (25HCDS) for use in a method of preventing or treating necrosis and/or apoptosis associated with necrosis of cells or tissue in a subject in need thereof.

77. 5-cholesten-3, 25-diol, 3-sulfate (25HC3S) and/or 5-cholesten 3, 25-diol, disulfate (25HCDS) for use in a method of preventing or treating acute liver failure and/or kidney failure in a subject in need thereof.

BRIEF DESCRIPTION OF THE DRAWINGS

FIGS. 2A and B. Effect of 25HC3S on recovery after administration of acetaminophen (ATMP). Normal represents sera from normal control mice; ATMP, mice treated with ATMP and vehicle; ATMP+25HC3S, mice treated with ATMP and 25HC3S. A, enzyme activities: ALT, alanine aminotransferase; AST, aspartate aminotransferase; ALK, alkaline phosphatase; LDH, lactate dehydrogenase; B, serum concentrations of BUN (blood urea nitrogen) and glucose. Each value represents mean of two animals.

FIG. 5A-D. Relative enzyme activity (units per deciliter of blood) of control vs treated rats for A, alanine aminotransferase (ALT), B, aspartate aminotransferase (AST), C, alkaline phosphatase (AKP) and D, antidiuretic hormone (ADH). Control rats received vehicle; treated rats received 25HC3S.

FIG. 8A-L. Results after brain ischemia injury. A, 7-point neuroscore; B, 20 point neuroscore; C, limb placing; D, 24-hr lesion volume ($mm^3$); E, 7-day lesion volume ($mm^3$); F, 24-hr oedema volume ($mm^3$); G, 7-day oedema volume ($mm^3$); H, 24-hr lesion volume (%); I, 7-day oedema volume (%); J, 24-hr T2 lesion (ms); K, 7-day T2 lesion (ms); L, body weights (vehicle/sham, vehicle/stroke and vehicle/25HC3S).

DETAILED DESCRIPTION OF THE INVENTION

Figures 1A, 1B, 1C, 1D:
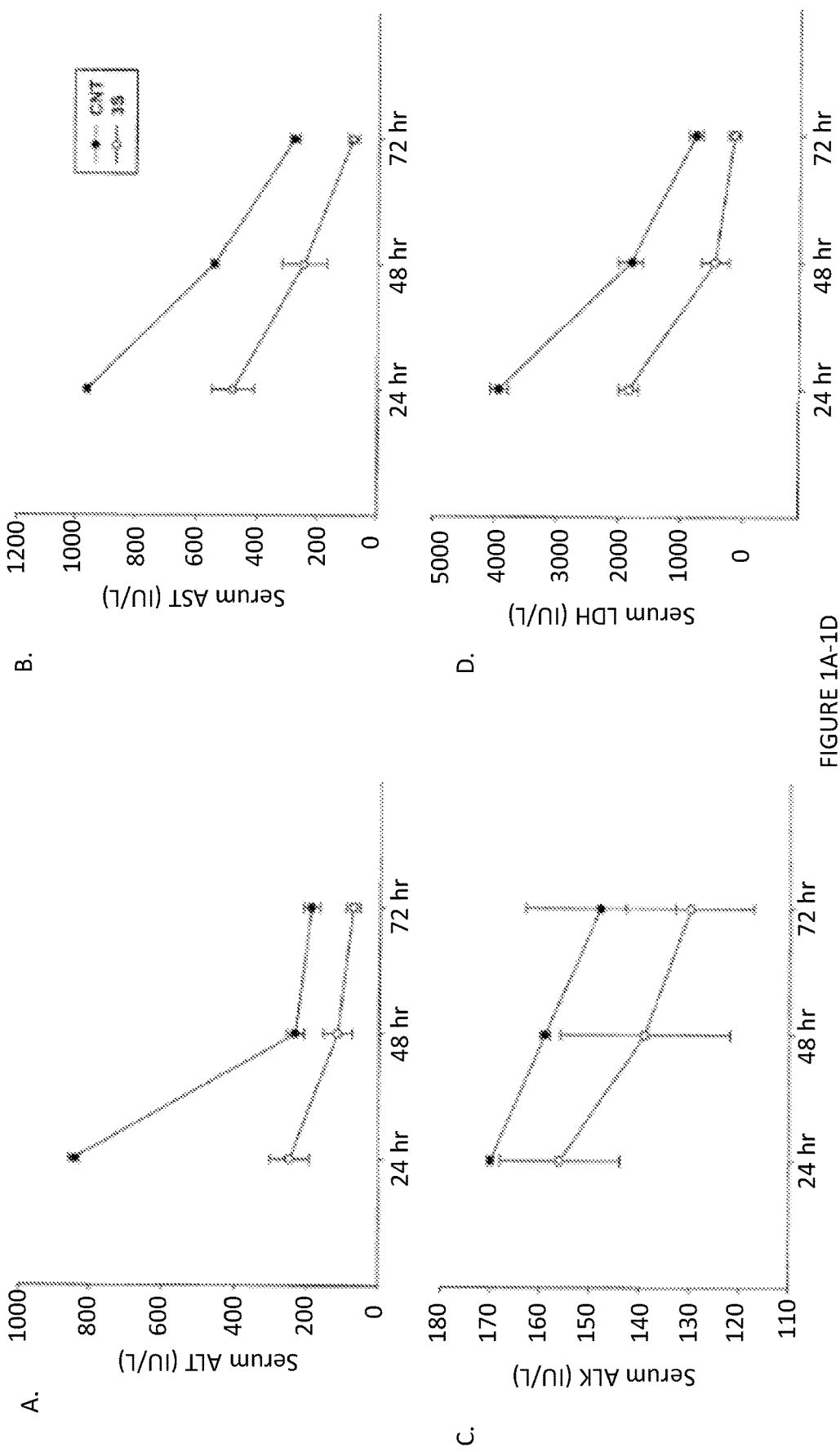
FIG. 1A-D. Effect of 25HC3S on recovery of acute liver failure induced by acetaminophen. Normal represents sera from normal control mice; ATMP, from mice treated with acetaminophen and vesicle injection; ATMP +25HC3S, from mice with acetaminophen and 25HC3S injection. A, ALT represents alanine aminotransferase; B, AST aspartate aminotransferase; C, ALK, alkaline phosphatase; D, LDH, lactate dehydrogenase. Each value represents mean of two animals.

Methods for preventing and/or treating organ or organ system dysfunction and/or failure are described herein, as are methods of treating unwanted necrosis and/or apoptosis associated with organ failure. The methods include contacting an organ of interest with at least one oxygenated cholesterol sulfate (OCS). If the organ of interest is within a patient (in vivo), then contact generally involves administering to the patient an amount of at least one OCS that is effective or sufficient to prevent and/or treat dysfunction and/or failure of one or more organs or organ systems in the patient, e.g. is sufficient to prevent or treat at least one symptom of organ dysfunction or failure exhibited by the patient. If an organ has already been harvested from a subject (i.e. from a donor), and is thus ex vivo, then contact generally involves contacting the organ with at least one OCS, i.e. applying at least one OCS to the organ, to preserve the organ, i.e. maintain the viability of the organ, and/or enhance maintenance of the organ, until it is transplanted.

Methods of preventing and/or treating conditions which lead to, cause or are caused by, or which are associated with organ dysfunction and failure are also described, e.g. prevention and/or treatment of inflammation, cell death (e.g. necrosis), consequences of ischemia, sepsis, and others. The methods involve administering, to a subject in need thereof, an amount of at least one OCS that is effective or sufficient to prevent and/or treat the condition.

In some aspects, the populations of subjects treated by the methods described herein may or may not have symptoms of and/or been diagnosed with high levels of cholesterol (hypercholesterolemia, e.g. cholesterol levels in serum in the range of about 200 mg/dl or more), or with a condition associated with high levels of cholesterol e.g. hyperlipidemia, atherosclerosis, heart disease, stroke, Alzheimer's, gallstone diseases, cholestatic liver diseases, etc. In some aspects, the populations of subjects described herein do not have symptoms of and/or have not been diagnosed with high levels of cholesterol (hypercholesterolemia, e.g. cholesterol levels in serum in the range of about 200 mg/dl or more), or with a condition associated with high levels of cholesterol e.g. hyperlipidemia, atherosclerosis, heart disease, stroke, Alzheimer's, gallstone diseases, cholestatic liver diseases, etc.

In further aspects, the populations of subjects treated by the methods described herein may or may not have symptoms of and/or been diagnosed with liver disorders such as hepatitis, inflammation of the liver, caused mainly by various viruses but also by some poisons (e.g. alcohol); autoimmunity (autoimmune hepatitis) or hereditary conditions; non-alcoholic fatty liver disease, a spectrum in disease, associated with obesity and characterized by an abundance of fat in the liver, which may lead to hepatitis, i.e. steatohepatitis and/or cirrhosis; cirrhosis, i.e. the formation of fibrous scar tissue in the liver due to replacing dead liver cells (the death of liver cells can be caused, e.g. by viral hepatitis, alcoholism or contact with other liver-toxic chemicals); haemochromatosis, a hereditary disease causing the accumulation of iron in the body, eventually leading to liver damage; cancer of the liver (e.g. primary hepatocellular carcinoma or cholangiocarcinoma and metastatic cancers, usually from other parts of the gastrointestinal tract); Wilson's disease, a hereditary disease which causes the body to retain copper; primary sclerosing cholangitis, an inflammatory disease of the bile duct, likely autoimmune in nature; primary biliary cirrhosis, an autoimmune disease of small bile ducts; Budd-Chiari syndrome (obstruction of the hepatic vein); Gilbert's syndrome, a genetic disorder of bilirubin metabolism, found in about 5% of the population; glycogen storage disease type II; as well as various pediatric liver diseases, e.g. including biliary atresia, alpha-1 antitrypsin deficiency, alagille syndrome, and progressive familial intrahepatic cholestasis, etc. In addition, liver damage from trauma may also be treated, e.g. damage caused by accidents, gunshot wounds, etc. Further, liver damage caused by certain medications may be prevented or treated, for example, drugs such as the antiarrhythmic agent amiodarone, various antiviral drugs (e.g. nucleoside analogues), aspirin (rarely as part of Reye's syndrome in children), corticosteroids, methotrexate, tamoxifen, tetracycline, etc. are known to cause liver damage. In further aspects, the populations of subjects treated by the methods described herein do not have symptoms of and/or have not been diagnosed with liver disorders such as hepatitis, inflammation of the liver, caused mainly by various viruses but also by some poisons (e.g. alcohol); autoimmunity (autoimmune hepatitis) or hereditary conditions; non-alcoholic fatty liver disease, a spectrum in disease, associated with obesity and characterized by an abundance of fat in the liver, which may lead to hepatitis, i.e. steatohepatitis and/or cirrhosis; cirrhosis, i.e. the formation of fibrous scar tissue in the liver due to replacing dead liver cells (the death of liver cells can be caused, e.g. by viral hepatitis, alcoholism or contact with other liver-toxic chemicals); haemochromatosis, a hereditary disease causing the accumulation of iron in the body, eventually leading to liver damage; cancer of the liver (e.g. primary hepatocellular carcinoma or cholangiocarcinoma and metastatic cancers, usually from other parts of the gastrointestinal tract); Wilson's disease, a hereditary disease which causes the body to retain copper; primary sclerosing cholangitis, an inflammatory disease of the bile duct, likely autoimmune in nature; primary biliary cirrhosis, an autoimmune disease of small bile ducts; Budd-Chiari syndrome (obstruction of the hepatic vein); Gilbert's syndrome, a genetic disorder of bilirubin metabolism, found in about 5% of the population; glycogen storage disease type II; as well as various pediatric liver diseases, e.g. including biliary atresia, alpha-1 antitrypsin deficiency, alagille syndrome, and progressive familial intrahepatic cholestasis, etc. In addition, liver damage from trauma may also be treated, e.g. damage caused by accidents, gunshot wounds, etc. Further, liver damage caused by certain medications may be prevented or treated, for example, drugs such as the antiarrhythmic agent amiodarone, various antiviral drugs (e.g. nucleoside analogues), aspirin (rarely as part of Reye's syndrome in children), corticosteroids, methotrexate, tamoxifen, tetracycline, etc. are known to cause liver damage.

In further aspects, the populations of subjects treated by the methods described herein may or may not have symptoms of non-alcoholic fatty liver disease (NAFLD) and/or nonalcoholic steatohepatitis (NASH). In further aspects, the populations of subjects treated by the methods described herein do not have symptoms of non-alcoholic fatty liver disease (NAFLD) and/or nonalcoholic steatohepatitis (NASH).

Definitions

The following definitions are used throughout:

Prevent and Treat

As used herein, "prophylactically treat" ("prophylactic treatment", "prophylactically treating" etc.) and "prevent" ("prevention", preventing" etc.) refer to warding off or averting the occurrence of at least one symptom of a disease or unwanted condition such as organ dysfunction or failure, by prophylactic administration of at least one OCS to a subject in need thereof. Generally, "prophylactic" or "prophylaxis" relates to a reduction in the likelihood of the patient developing a disorder. Typically, the subject is considered by one of skill in the art to be at risk of or susceptible to developing at least one symptom of the disease or unwanted condition, or is considered to be likely to develop at least one symptom of the disease/condition in the absence of medical intervention. Generally, however, for "prevention" or "prophylactic treatment", administration occurs before the subject has, or is known or confirmed to have, symptoms of the disease (condition, disorder, syndrome, etc.; unless otherwise indicated, these terms are used interchangeably herein). In other words, symptoms may not yet be overt or observable. The subject may be considered at risk due to a variety of factors, including but not limited to: genetic predisposition; an impending medical or surgical procedure (e.g. surgery, use of a contrast dye in imaging, chemotherapy, etc.); recent certain or suspected or unavoidable future exposure to a toxic agent (e.g. a toxic chemical or medication, radiation, etc.); or exposure to or experience of another stressor or combination of stressors that is/are linked to or associated with the development of the disease/condition which is being prevented. In some aspects of the prevention of organ dysfunction/failure, the subject may already display symptoms of a potential precursor of organ dysfunction/failure, for example, ischemic, sepsis, a harmful or inappropriate level of inflammation, deleterious cell death, necrosis, etc. In such aspects, treatment of the subject may prevent the noxious or harmful effects or outcomes (results) of the precursor condition. "Prevention" or "prophylactic treatment" of a disease or condition may involve completely preventing the occurrence of detectable symptoms, or, alternatively, may involve lessening or attenuating the degree, severity or duration of at least one symptom of the disease that would occur in the absence of the medical interventions provided herein, i.e. unless one or more OCSs is administered. Alternatively, the subject may be experiencing early stage symptoms and what is prevented is the progression to full-blown disease.

In some aspects, the disease outcome or result that is prevented is death of the subject.

"Treat" (treatment, treating, etc.) as used herein refers to administering at least one OCS to a subject that already exhibits at least one symptom of the disease. In other words, at least one parameter that is known to be associated with the disease has been measured, detected or observed in the subject. Organ dysfunction/failure and/or precursors thereof that are treated as described herein are caused by somewhat predictable factors (e.g. see the above description of diseases and conditions which may lead to organ dysfunction/failure), or by unexpected causes such as trauma due to accidents (recreational and non-recreational), war, undiagnosed allergies or other risk factors, etc. "Treatment" of a disease involves the lessening or attenuation, or in some instances, the complete eradication, of at least one symptom of the disease that was present prior to or at the time of administration of one or more OCSs. Thus, for example, treatment of ischemia includes preventing or treating damage associated with ischemia and, for example treatment of sepsis includes preventing or treating damage associated with sepsis.

Those of skill in the art will recognize that one or more of organ dysfunction, organ failure, and/or one or more conditions which are precursors of organ dysfunction or failure may be comorbid, i.e. may be present in a subject or individual at the same time. For example, a subject may have active sepsis that results in organ failure. Thus, preventing and/or treating may overlap in that treating sepsis may, at the same time, prevent the occurrence of organ failure; or treating ischemia may prevent or treat inflammation that occurs following an ischemic event, that would lead to organ failure but for the administration of an OCS.

Examples of OCS that are used in the methods and compositions described herein include but are not limited to 5-cholesten-3, 25-diol, 3-sulfate (25HC3S); 5-cholesten, 3b, 25-diol, disulfate (25HCDS); (5-cholestene, 3, 27-diol, 3-sulfate); (5-cholestene, 3, 27-diol, 3, 27-disulfate); (5-cholestene, 3,7-diol, 3-sulfate); (5-cholestene, 3,7-diol, 3,7-disulfate); (5-cholestene, 3, 24-diol, 3-sulfate); (5-cholestene, 3, 24-diol, 3, 24-disulfate); and (5-cholestene, 3-ol, 24, 25-epoxy 3-sulfate). Disclosure of 25HC3S is found in, e.g., U.S. Pat. No. 8,399,441, which is incorporated herein by reference in its entirety. Disclosure of 25HCDS is found, e.g., in WO 2013/154752, which is incorporated by reference in its entirety. In certain aspects, the OCS are selected from 5-cholesten-3, 25-diol, 3-sulfate (25HC3S) and 5-cholesten, 3b, 25-diol, disulfate (25HCDS) (either alone or in combination). In further aspects, the OCS is 5-cholesten-3, 25-diol, 3-sulfate (25HC3S).

The OCSs are typically synthetic versions of OCSs that occur naturally in the body. The exogenous OCS may be administered forms not naturally found in the body, and in concentrations that are significantly higher than those which occur naturally. For 25HC3S, natural levels typically range from e.g. about 2 ng/ml or less up to about 5 ng/ml. The concentration of OCS (e.g. 25HC3S) in the blood or plasma of a patient that is treated with an OCS (e.g. 25HC3S) is generally greater than about 5 ng/ml, and generally ranges from about 50 ng/ml to about 5000 ng/ml, such as about 80 ng/ml to about 3000 ng/ml, e.g. from about 100 to about 2000 ng/ml, or from about 200 to about 1000 ng/ml.

As used herein, "organ" refers to a differentiated and/or relatively independent body structure comprising cells and tissues that performs some specialized function in the body of an organism. An "organ system" refers to two or more organs that work together in the execution of a body function. A hollow organ is an internal visceral organ (viscus) that forms a hollow tube or pouch, or that includes a cavity. Exemplary organs, the dysfunction or failure of which are prevented and/or treated by the administration of or contact with one or more OCS, include but are not limited to: heart, lungs, (e.g., lungs damaged by pulmonary fibrosis, e.g., associated with chronic asthma), liver, pancreas, kidneys, brain, intestines, colon, thyroid, etc. In some cases, the dysfunction or failure which is prevented and/or treated by the administration of the one or more OCS involves an organ other than the liver, for example heart, lungs, pancreas, kidneys, brain, intestines, colon, etc. In general, methods and compositions described herein that refer to "organs" should also be understood to include "organ systems", unless otherwise specified.

"Organ dysfunction" denotes a condition or a state of health where an organ does not perform its expected function. Organ function represents the expected function of the respective organ within physiologic ranges. The person skilled in the art is aware of the respective function of an organ during medical examination. Organ dysfunction typically involves a clinical syndrome in which the development of progressive and potentially reversible physiological dysfunction in an organ, optionally in the absence of anatomic injuries.

"Organ failure" denotes an organ dysfunction to such a degree that normal homeostasis cannot be maintained without external clinical intervention.

"Acute organ dysfunction" refers to reduced organ function that occurs rapidly—in days or weeks (e.g., within 26 weeks, within 13 weeks, within 10 weeks, within 5 weeks, within 4 weeks, within 3 weeks, within 2 weeks, within 1 week, within 5 days, within 4 days, within 3 days, or within 2 days)—usually in a person who has no pre-existing disease.

"Acute organ failure" refers to loss of organ function that occurs rapidly—in days or weeks (e.g., within 26 weeks, within 13 weeks, within 10 weeks, within 5 weeks, within 4 weeks, within 3 weeks, within 2 weeks, within 1 week, within 5 days, within 4 days, within 3 days, or within 2 days)—usually in a person who has no pre-existing disease. For instance, the term "acute renal failure" means a rapid deterioration in renal function sufficient to result in accumulation of waste products in the body. Acute liver failure is discussed in more detail below.

As used herein, "ischemia" refers to a reduction in blood flow to an organ.

The terms "sepsis" and "septicemia" refer to a morbid condition resulting from the invasion of the bloodstream by microorganisms and their associated endotoxins.

"Endotoxin" refers to any harmful components of microbial cells such as lipopolysaccharides from the Gram-negative bacterial cell wall, peptidoglycans from Gram-positive bacteria, and mannan from fungal cell walls.

Description of Administration of Oxygenated Cholesterol Sulfates (OCS)

Implementation of the methods generally involves identifying patients suffering from or at risk of developing organ dysfunction or failure, or a condition associated with organ dysfunction or failure, and administering one or more OCS in an acceptable form by an appropriate route. The exact dosage to be administered may vary depending on the age, gender, weight and overall health status of the individual patient, as well as the precise etiology of the disease. However, in general for administration in mammals (e.g. humans), dosages in the range of from about 0.001 to about 100 mg or more of compound per kg of body weight per 24 hr., and preferably about 0.01 to about 50 mg of compound per kg of body weight per 24 hr., and more preferably about 0.1 to about 10 mg of compound per kg of body weight per 24 hr. are effective. Daily doses generally range from about 0.1 milligrams to about 5000 milligrams of OCS such as 25HC3S (or a pharmaceutically acceptable salt thereof) per person per day. In some aspects, the dose is from about 10 milligrams to about 2000 milligrams per person per day, or about 100 milligrams to about 1000 milligrams per person per day. The dose will vary with the route of administration, the bioavailability, and the particular formulation that is administered, as well as according to the nature of the malady that is being prevented or treated. Further, the effective dose can vary depending upon factors such as gender, age, and other conditions of the patient, as well as the extent or progression of the disease condition being treated.

Administration may be oral or parenteral, including intravenously, intramuscularly, subcutaneously, intradermal injection, intraperitoneal injection, etc., or by other routes (e.g. transdermal, sublingual, rectal and buccal delivery, inhalation of an aerosol, intravaginally, intranasally, topically, as eye drops, via sprays, etc.). The route of administration will depend on the nature or the condition that is treated, e.g. on the type or degree of organ injury and/or organ failure and/or associated necrosis and/or apoptosis, and whether the treatment is prophylactic or intended to effect a cure. For example, to achieve a preventative effect before organ dysfunction has occurred, oral dosing may be sufficient, especially in view of the excellent bioavailability of orally administered OCS. Further, administration of the compound by any means may be carried out as a single mode of therapy, or in conjunction with other therapies and treatment modalities, e.g. diet regimens, etc.

The subject to whom the OCS is administered is generally a mammal, frequently a human, but this is not always the case. Veterinary applications of this technology are also contemplated, e.g. for companion pets (cats, dogs, etc.), or for livestock and farm animals, for horses, and even for "wild" animals that have special value or that are under the case of a veterinarian, e.g. animals in preserves or zoos, injured animals that are being rehabilitated, etc.

In some aspects, the compositions are administered in conjunction with other treatment modalities such as various pain relief medications, anti-arthritis agents, various chemotherapeutic agents, antibiotic agents, and the like, depending on the malady that is afflicting the subject. "In conjunction with" refers to both administration of a separate preparation of the one or more additional agents, and also to inclusion of the one or more additional agents in a composition of the present disclosure. In particular, the OCS may be administered in conjunction with an agent that is known to cause organ damage in order to prevent the organ damage. For example, aspirin, ibuprofen and acetaminophen all have potential serious organ-damaging side effects when taken long term, or when taken by certain venerable groups (e.g. the very young, the elderly, etc.), or when overdoses are ingested, etc. Accordingly, dosage forms comprising at least one OCS and one or more of such agents are contemplated.

The amount of OCS that is effective in protecting against aspirin-, ibuprofen- or acetaminophen-induced organ injury can be determined by standard clinical techniques. In addition, in vitro or in vivo assays can optionally be employed to help identify optimal dosage ranges. The precise dose to be employed will also depend on the route of administration, and can be decided according to the judgment of the practitioner and each patient's circumstances. However, suitable daily doses for oral administration generally from about 0.1 milligrams to about 5000 milligrams of OCS such as 25HC3S (or a pharmaceutically acceptable salt thereof) per person per day. In some aspects, an oral dose is from about 10 milligrams to about 2000 milligrams per person per day, or about 100 milligrams to about 1000 milligrams per person per day. Oral compositions are generally contemplated for prophylactic use, e.g. when the potentially dangerous agent is taken for a long period of time (weeks, months or years) and it is desired to prevent organ damage or other adverse effects. However, when treatment is needed for damage that has already occurred, the compositions are generally formulated for parenteral or, more usually, for intravenous administration.

The compounds may be administered in the pure form or in a pharmaceutically acceptable formulation including suitable elixirs, binders, and the like (generally referred to a "carriers") or as pharmaceutically acceptable salts (e.g. alkali metal salts such as sodium, potassium, calcium or lithium salts, ammonium, etc.) or other complexes. It should be understood that the pharmaceutically acceptable formulations include liquid and solid materials conventionally utilized to prepare both injectable dosage forms and solid dosage forms such as tablets and capsules and aerosolized dosage forms. In addition, the compounds may be formulated with aqueous or oil based vehicles. Water may be used as the carrier for the preparation of compositions (e.g. injectable compositions), which may also include conventional buffers and agents to render the composition isotonic. Other potential additives and other materials (preferably those which are generally regarded as safe [GRAS]) include: colorants; flavorings; surfactants (TWEEN®, oleic acid, etc.); solvents, stabilizers, elixirs, and binders or encapsulants (lactose, liposomes, etc). Solid diluents and excipients include lactose, starch, conventional disintegrating agents, coatings and the like. Preservatives such as methyl paraben or benzalkium chloride may also be used. Depending on the formulation, it is expected that the active component (at least one OCS) will be present as about 1% to about 99% of the composition and the vehicular "carrier" will constitute about 1% to about 99% of the composition. The pharmaceutical compositions of the present disclosure may include any suitable pharmaceutically acceptable additives or adjuncts to the extent that they do not hinder or interfere with the therapeutic effect of the OCS(s). Additional suitable agents that may be co-administered or co-formulated also include other agents that are used to e.g. combat acetaminophen toxicity, including but not limited to: metabolites of the methionine and/or glutathione biosynthetic pathways such as S-adenosylhomocysteine (SAH), S-methylmethionine (SMM), cystine, betaine, etc. or various forms and/or salts thereof e.g. acetylcysteine (e.g. intravenous N-acetylcysteine), various neutraceuticals, etc.

The administration of the compound of the present disclosure may be intermittent, or at a gradual or continuous, constant or controlled rate. In addition, the time of day and the number of times per day that the pharmaceutical formulation is administered may vary and are best determined by a skilled practitioner such as a physician. For example, the compound may be administered within 1 week, such as within 1 day, within 12 hours, within 1 hour, or within 10 minutes, of an overdose e.g. of an agent that causes organ damage. The compound may be administered at least once a day (e.g., twice daily) before surgery for at least 1 month or at least 1 week, or at least 1 day before surgery, or even during surgery, e.g. surgery related to or associated with or which may cause organ failure (e.g. surgery that involves intentional ischemia/reperfusion). The compound may also be administered on at least a daily basis (e.g., twice daily) after surgery for at least 1 day, at least 1 week, or at least 1 month. For example, the surgery may be heart surgery (e.g., coronary artery bypass grafting (CABG)), cardiovascular surgery, heart-lung transplant, lung surgery (e.g., pulmonary embolism surgery), deep vein thrombosis (DVT) surgery, brain surgery, liver surgery, bile duct surgery, kidney surgery (e.g., kidney stone surgery), gastrointestinal surgery (e.g., intestinal, intestinal blockage, diverticulitis, or intestinal torsion surgery), or aneurysm surgery. In some cases, such as when the one or more organs to be treated comprises a liver, the administering may occur for not more than 14 days, such as not more than 10 days, not more than 8 days, not more than 5 days, or not more than 1 day.

The OCS are typically administered as compositions that are prepared in solid forms such as tablets, pills, powders, suppositories, various slow- or extended-release formulations, and the like, or as liquid solutions, suspensions, emulsions, etc. or liquids suitable for injection and/or intravenous administration. Solid forms suitable for solution in, or suspension in, liquids prior to administration may also be prepared. The active ingredients may be mixed with excipients which are pharmaceutically acceptable and compatible with the active ingredients, e.g. pharmaceutically and physiologically acceptable carriers. Suitable excipients include, for example, water, saline, dextrose, glycerol, ethanol and the like, or combinations thereof. In addition, the composition may contain minor amounts of auxiliary substances such as wetting or emulsifying agents, pH buffering agents, and the like. Oral dosage forms may include various thickeners, flavorings, diluents, emulsifiers, dispersing aids, binders, coatings and the like. The composition of the present disclosure may contain any such additional ingredients so as to provide the composition in a form suitable for the intended route of administration. The final amount of OCS in a formulation may also vary but in general will be from about 1-99%. Still other suitable formulations for use in the present disclosure can be found, for example in Remington's Pharmaceutical Sciences, Philadelphia, Pa., 19th ed. (1995); and Akers, Michael J. Sterile Drug Products: Formulation, Packaging, Manufacturing and Quality; publisher Informa Healthcare (2010).

The compositions (preparations) of the present disclosure may be formulated for and administered by any of the many suitable means which are known to those of skill in the art, including but not limited to: orally, by injection, rectally, by inhalation, intravaginally, intranasally, topically, as eye drops, via sprays, etc. In some aspects, the mode of administration is oral, by injection or intravenously. Typically, oral administration is particularly effective when used prophylactically, e.g. to prevent organ damage (e.g. caused by or necrosis and/or apoptosis) and that would otherwise occur in a patient who is taking an organ-damaging agent for a prolonged period of time, e.g. weeks, months or years. When damage has already occurred, and especially when acute organ failure is diagnosed, the route of administration is generally parenteral or intravenous to speed delivery of the OCS.

Prevention and/or Treatment of Organ and/or Organ System Dysfunction and/or Failure In some aspects, the present disclosure provides methods for preventing and/or treating the dysfunction and/or failure of one or more organs or organ systems in a subject in need thereof. In some aspects, the organ and/or organ system dysfunction and/or failure is acute.

The methods may include administering to the subject a therapeutically effective or sufficient amount of one or more OCS. The amount is sufficient to prevent and/or treat dysfunction of the organ(s) being treated, or to prevent and/or treat failure of the organ(s) being treated. In some aspects, the organ failure that is treated is Multiple Organ Dysfunction Syndrome (MODS). The methods generally include identifying or diagnosing subjects who are in need of such treatment, e.g. subjects that would benefit from such treatment e.g. due to being susceptible to organ dysfunction or failure, or already exhibiting at least one sign or symptom of organ dysfunction or failure. For example, the subject may be a member of a particular patient population such as those with disease resulting from acute insult (acute organ injury resulting from bacterial infection, severe burns, trauma, etc), or chronic conditions (long-term exposure to organ-damaging medication), and/or from other causes which are discussed in more detail below.

The patient group(s) addressed by the present disclosure can also be defined as follows. The SOFA system was created in a consensus meeting of the European Society of Intensive Care Medicine in 1994 and further revised in 1996. The SOFA is a six-organ dysfunction/failure score measuring multiple organ failure daily. Each organ is graded from 0 (normal) to 4 (the most abnormal), providing a daily score of 0 to 24 points. The objective of the SOFA is to create a simple, reliable, and continuous score for clinical staff. Sequential assessment of organ dysfunction during the first few days of intensive care unit (ICU) or hospital admission is a good indicator of prognosis. Both the mean and highest SOFA scores are particularly useful predictors of outcome.

In a specific aspect, the patient group pursuant to the invention is one having as a lower threshold at least one SOFA score, being at 1 for one of the clinical criteria of respiration, or liver, or coagulation, or cardiovascular, or CNS, or renal on the day of admission to hospital or Intensive Care Unit (ICU). Thus, said patient group is in need of therapeutic intervention pursuant to the present invention, and thus in need for prevention or reduction of organ dysfunction or organ failure.

In another specific aspect, the patient group pursuant to the present disclosure is one having as lower threshold at least two SOFA scores, being at 1 each for two of the clinical criteria respiration, and/or liver, and/or coagulation, and/or cardiovascular, and/or CNS, and/or renal on the day of admission to hospital or Intensive Care Unit (ICU). Thus, said patient group is in need of therapeutic intervention pursuant to the present disclosure, and thus in need for prevention or reduction of organ dysfunction or organ failure.

In another specific aspect, the patient group pursuant to the present disclosure is one having as a lower threshold at least three SOFA scores, being at 1 each for three of the clinical criteria respiration, and/or liver, and/or coagulation, and/or cardiovascular, and/or CNS, and/or renal on day of admission to hospital or Intensive Care Unit (ICU). Thus, said patient group is in need of therapeutic intervention pursuant to the present disclosure, and thus in need for prevention or reduction of organ dysfunction or organ failure.

In another specific aspect, the patient group pursuant to the present disclosure is one having as a lower threshold at least four SOFA scores, being at 1 each for four of the clinical criteria respiration, and/or liver, and/or coagulation, and/or cardiovascular, and/or CNS, and/or renal on the day of admission to hospital or Intensive Care Unit (ICU). Thus, said patient group is in need of therapeutic intervention pursuant to the present disclosure, and thus in need for prevention or reduction of organ dysfunction or organ failure.

In another specific embodiment, the patient group in need of prevention or reduction of renal organ dysfunction or renal organ failure pursuant to the present disclosure is having a renal SOFA score of at least 1, or of 2, or of 3, or of 4.

In another specific embodiment, the patient group in need of prevention or reduction of liver organ dysfunction or liver organ failure pursuant to the present disclosure is having a liver SOFA score of at least 1, or of 2, or of 3, or of 4.

In another specific embodiment, the patient group in need of prevention or reduction of heart organ dysfunction or heart organ failure pursuant to the present disclosure is having a cardiovascular SOFA score of at least 1, or of 2, or of 3, or of 4.

In another specific embodiment the patient group in need of prevention or reduction of lung organ dysfunction or lung organ failure pursuant to the present disclosure is having a respiratory SOFA score of at least 1, or of 2, or of 3, or of 4.

Independent of the initial score, generally an increase in SOFA score during the first 48 hours in the ICU or in the hospital predicts a mortality rate of at least 50%.

Thus, in another specific embodiment the patient group in need of therapeutic intervention for organ dysfunction/failure in accordance with present disclosure is characterized by having at least one SOFA score increased within the initial 48 hours after admission to hospital or ICU.

In some aspects, the organ, organs or organ systems which is/are subject to failure comprise at least one member of the following: cardiovascular, respiratory, renal, haematological, neurological, gastrointestinal organs, hepatic organs, heart, liver, lungs, intestines, colon, kidneys, spleen, and brain.

In some embodiments, the OCS is to be used in combination with fluids administered intravenously, wherein said combination is for use in therapy of a subject having a chronic or acute disease or acute condition of a patient for protecting the organs of said patient. The fluids to be administered intravenously are, of course, administered systemically.

In one embodiment, the subject having a chronic or acute disease or condition being in need for protecting its organs is characterized by the need of the subject to receive intravenous fluids.

The at least one OCS of the present disclosure may be applied for sake of prevention or reduction of organ dysfunction and organ failure, and thus the at least one OCS is not necessarily intended for any methods of primary treatment or first line treatment to the chronic or acute disease or acute condition itself, which therefore can be termed as underlying disease(s). This means the present disclosure does not necessarily provide for a therapy of healing/curing e.g. infections, cancer, or tumors located in the respective organ, but for resuscitating the respective organ towards physiologic function. Accordingly, the therapy for a chronic or acute disease or acute condition of a patient within the scope of the present disclosure includes any kind of organ insufficiency, or poor organ function as an acute event.

Prevention and/or Treatment of Kidney Dysfunction and/or Failure

Kidney disease may be acute or chronic, or even acute-on-chronic renal failure as discussed below.

Acute kidney injury (AKI, previously called acute renal failure (ARF)) refers to an abrupt loss of kidney function that develops e.g. within about 7 days. AKI generally occurs because of damage to the kidney tissue caused by decreased renal blood flow (renal ischemia) from any cause e.g. low blood pressure, exposure to substances harmful to the kidney, an inflammatory process in the kidney, or an obstruction of the urinary tract which impedes the flow of urine. Causes of acute kidney injury include accidents, injuries, or complications from surgeries in which the kidneys are deprived of normal blood flow for extended periods of time. Heart-bypass surgery is an example of one such procedure. Drug overdoses, either accidental or from chemical overloads of drugs such as antibiotics or chemotherapy, may also cause the onset of acute kidney injury. AKI is diagnosed on the basis of characteristic laboratory findings, such as elevated blood urea nitrogen (BUN) and creatinine, or inability of the kidneys to produce sufficient amounts of urine (e.g. less than 400 mL per day in adults, less than 0.5 mL/kg/h in children or less than 1 mL/kg/h in infants). Thus, the present methods may include measuring or detecting one or more of these parameters in a subject and, if one or more or the measured parameters is positive and thus indicative of the presence of kidney malfunction developing within about 7 days, then diagnosing acute kidney injury and administering at least one OCS to the subject, as described herein.

Chronic kidney disease (CKD) usually develops slowly and, initially, patients may show few symptoms. CKD can be the long term consequence of irreversible acute disease or part of a disease progression. CKD has numerous causes, including diabetes mellitus, long-term, uncontrolled hypertension, polycystic kidney disease, infectious diseases such as hantavirus, and certain genetic predisposition e.g. APOL1 gene variants. The present methods include administering at least one OCS to a subject having CKD.

In some cases, the clinical criteria denoting the patient group(s) for kidney dysfunction/failure are as follows:
Patients at risk for kidney dysfunction/failure: GFR decrease >25%, serum creatinine increased 1.5 times or urine production of <0.5 ml/kg/hr for 6 hours
Patients with present kidney injury: GFR decrease >50%, doubling of creatinine or urine production <0.5 ml/kg/hr for 12 hours
Patients with kidney failure: GFR decrease >75%, tripling of creatinine or creatinine >355 mol/l (with a rise of >44) (>4 mg/dl) or urine output below 0.3 ml/kg/hr for 24 hours
Patients with loss of kidney function: persistent acute kidney injury (AKI) or complete loss of kidney function for more than 4 weeks
End-stage renal disease: complete loss of kidney function for more than 3 months.

The overuse of drugs such as aspirin, ibuprofen, and acetaminophen (paracetamol) can also cause chronic kidney disease. This type of damage can be avoided by administering these agents in combination with at least one OCS, either via administration of the OCS in coordination with administration of the agent (e.g. before or after or at the same time but in a separate preparation); or, alternatively, by administering compositions comprising 1) liver-toxic drug such as aspirin, ibuprofen, and/or acetaminophen; and 2) at least one OCS. Accordingly, compositions comprising aspirin plus one or more OCS are provided, as are compositions comprising ibuprofen plus one or more OCS and compositions comprising acetaminophen plus one or more OCS.

In compositions comprising aspirin plus one or more OCS, the aspirin is generally present in an approximate range of 80 mg to 1000 mg per unit dose (e.g. a single oral dosage form such as a pill, tablet, liquid etc.), i.e. about 80, 90, 100, 150, 200, 250, 300, 350, 400, 450, 500, 550, 600, 650, 700, 750, 800, 850, 900, 950, or 1000 mg. In compositions comprising ibuprofen plus one or more OCS, the ibuprofen is present in a range of approximately 50 mg to 500 mg, usually approximately 100 mg to 350 mg, and most usually approximately 125 mg to 250 mg per unit dose (e.g. in a single oral dosage form such as a pill, tablet, liquid, etc.). Exemplary doses of ibuprofen include 50, 60, 70, 80, 90, 100, 150, 200, 250, 300, 350, 400, 450 and 500 mg. The dosage of acetaminophen ranges from about 50 to about 4000 mg per dose, e.g. about 50, 75, 100,125,150, 200, 225, 250, 275, 300, 325, 350, 375, 400, 425, 450, 475, 500, 525, 550, 575, 600, 625, 650, 675, 700, 725, 750, 775, 800. 825, 850, 875, 900, 925, 950, 975, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900 or about 4000 mg/dose.

Such compositions may be prepared in solid forms such as tablets, pills, powders, suppositories, various slow- or extended-release formulations, and the like, or as liquid solutions, suspensions, emulsions, etc. or liquids suitable for injection and/or intravenous administration. Solid forms suitable for solution in, or suspension in, liquids prior to administration may also be prepared. The active ingredients may be mixed with excipients which are pharmaceutically acceptable and compatible with the active ingredients. Suitable excipients include, for example, water, saline, dextrose, glycerol, ethanol and the like, or combinations thereof. In addition, the composition may contain minor amounts of auxiliary substances such as wetting or emulsifying agents, pH buffering agents, and the like. Oral dosage forms may include various thickeners, flavorings, diluents, emulsifiers, dispersing aids, binders, coatings and the like. The compositions of the present disclosure may contain any such additional ingredients so as to provide the composition in a form suitable for the intended route of administration. The final amount of aspirin, ibuprofen and/or acetaminophen in a formulation may vary but in general will be from about 1-99%. The final amount of OCS in a formulation may also vary but in general will be from about 1-99%, with particular recommended doses being those described above. Still other suitable formulations for use in the present disclosure can be found, for example in Remington's Pharmaceutical Sciences, Philadelphia, Pa., 19th ed. (1995); and Akers, Michael J. Sterile Drug Products: Formulation, Packaging, Manufacturing and Quality; publisher Informa Healthcare (2010).

Acetaminophen formulations that may be used in the compositions of the present disclosure (which also include at least one OCS such as 25HC3S) are described, for example, in U.S. Pat. Nos. 6,936,601; 6,926,907; 6,924,273; 6,916, 788; 6,855,310; 6,852,336; 6,841,544; 6,833,362; 6,828, 328; 6,787,164; 6,740,333; 6,702,850; 6,696,066; 6,686, 390; 6,642,243; 6,627,234; 6,622,856; 6,613,346; 6,602, 518; 6,593,331; 6,586,023; 6,569,439; 6,566,401; 6,566, 361; 6,544,548; 6,528,097; 6,524,623; 6,511,982; 6,509, 380; 6,492,334; 6,485,747; 6,482,831; 6,479,551; 6,475, 526; 6,475,494; 6,458,809; 6,444,665; 6,440,983; 6,429, 223; 6,413,512; 6,406,716; 6,391,886; 6,391,337; 6,391, 294; 6,384,054; 6,383,527; 6,383,515; 6,375,957; 6,369, 084; 6,369,082; 6,355,666; 6,350,467; 6,335,034; 6,309, 669; 6,306,842; 6,303,632; 6,284,274; 6,277,384; 6,254, 891; 6,245,802; 6,245,357; 6,242,493; 6,225,295; 6,221, 377; 6,217,911; 6,217,907; 6,214,386; 6,187,338; 6,162, 647; 6,159,500; 6,139,861; 6,127,352; 6,126,967; 6,077, 533; 6,077,530; 6,057,347; 6,054,451; 6,048,540; 6,028, 222; 6,007,841; 5,998,434; 5,972,916; 5,968,551; 5,965, 167; 5,965,166; 5,945,416; 5,942,530; 5,919,826; 5,914, 129; 5,897,880; 5,891,801; 5,891,477; 5,872,145; 5,863, 922; 5,840,731; 5,837,729; 5,827,852; 5,776,462; 5,773,031; 5,739,139; 5,733,578; 5,724,957; 5,654,334; 5,639,475; 5,612,061; 5,603,959; 5,538,959; 5,474,757; 5,468,482; 5,466,865; 5,458,879; 5,417,980; 5,409,944; 5,409,709; 5,336,691; 5,322,689; 5,296,241; 5,273,759; 5,260,340; 5,238,686; 5,204,118; 5,154,926; 5,100,675; 5,036,097; 5,023,085; 5,011,688; 4,971,960; 4,971,785; 4,829,064; 4,822,781; 4,812,446; 4,794,112; 4,730,007; 4,703,045; 4,478,822; 4,476,115; 4,466,960; 4,460,368; 4,401,665; 4,314,989; 4,307,073; 4,260,629; 4,242,353; 4,237,140; 4,234,601; 4,233,317; 4,233,316; 4,233,315; 4,233,314; 4,233,313; 4,207,340; 4,132,788 and 4,049,803, and in pending US patent application 2012/0172324, the disclosures of which are incorporated by reference in their entireties.

Contrast and enhancing dyes used for various types of imaging, especially iodine containing dyes, are also known to cause kidney damage, especially in susceptible populations such as the elderly, diabetics, those who already have some form of kidney impairment, etc. Contrast-induced nephropathy is defined as either a greater than 25% increase of serum creatinine or an absolute increase in serum creatinine of 0.5 mg/dL in the wake of administration of a dye e.g. for X-rays or computed tomography (CT) scans. Iodine containing dyes include but are not limited to iohexol, iodixanol and ioversol, as well as other ionic iodine dyes such as Diatrizoate (Hypaque 50), Metrizoate (Isopaque 370), and Ioxaglate (Hexabrix); and non-ionic contrast media such as Iopamidol (Isovue 370), Iohexol (Omnipaque 350), Ioxilan (Oxilan 350), Iopromide (Ultravist 370), and Iodixanol (Visipaque 320). The OCS described herein can prevent or lessen the impact of such dyes when administered, for example, before administration of the dye, and/or concomitantly with the dye and/or after dye administration to maintain kidney values at a normal level in spite of exposure to the dye, or to facilitate or speed the return of those values to safe, normal ranges after dye administration.

Prevention and/or Treatment of Liver Dysfunction and/or Failure

An exemplary aspect of the present disclosure involves the treatment of acute liver failure, especially acute liver failure caused by necrosis. Acute liver failure involves the rapid development of hepatocellular dysfunction, specifically coagulopathy and mental status changes (encephalopathy) in a patient without known prior liver disease. This malady embraces a number of conditions whose common thread is severe injury of hepatocytes and/or massive necrosis e.g. loss of function of 80-90% of liver cells. Loss of hepatocyte function sets in motion a multiorgan response characterized by the rapid appearance of severe complications soon after the first signs of liver disease (such as jaundice). Complications include hepatic encephalopathy and impaired protein synthesis, e.g. as measured by the levels of serum albumin and the prothrombin time in the blood. Up to now, treatment options for acute liver failure have been limited and death often occurs suddenly, even after the liver has begun to recover from the original damage.

The diagnosis of acute liver failure (i.e. the identification of subject experiencing acute liver failure and who could benefit from the practice of the present methods) is generally based on physical exam, laboratory findings, patient history, and past medical history to establish, for example, mental status changes, coagulopathy, rapidity of onset, and absence of known prior liver disease. The exact definition of "rapid" depends on the particular convention that is used. Different sub-divisions exist which are based on the time from onset of first hepatic symptoms to onset of encephalopathy. One scheme defines "acute hepatic failure" as the development of encephalopathy within 26 weeks of the onset of any hepatic symptoms. This is sub-divided into "fulminant hepatic failure", which requires onset of encephalopathy within 8 weeks, and "subfulminant", which describes onset of encephalopathy after 8 weeks but before 26 weeks. Another scheme defines "hyperacute" liver failure as onset within 7 days, "acute" liver failure as onset between 7 and 28 days, and "subacute" liver failure as onset between 28 days and 24weeks. Subjects identified as experiencing acute liver failure by any of these criteria may be treated by the methods described herein.

In some cases, the patient group for liver dysfunction/failure is characterized by a lower threshold of Bilirubin of >1.2 mg/dL, preferably >1.9 mg/dL, more preferably >5.9 mg/dL.Acute liver failure has many potential causes and subjects identified as experiencing acute liver failure for any reason can be treated by the methods described herein. Possible causes include:

Acetaminophen (ATMP). Taking too much acetaminophen (paracetamol, Tylenol®, others) is the most common cause of acute liver failure in the United States. Acute liver failure can occur if a single very large dose of ATMP is taken all at once, or it can occur if higher-than-recommended doses are taken every day for several days. People with chronic liver disease are especially vulnerable, as are the elderly, the very young, etc. In such subjects, an ATMP "overdose" may be a dose that would be a safe or normal dose for a person that does not have chronic liver disease or is not elderly or very young. This aspect of the disclosure is discussed in detail below.

Prescription medications. Some prescription medications, including antibiotics, nonsteroidal anti-inflammatory drugs and anticonvulsants, can cause acute liver failure.

Herbal supplements. Herbal drugs and supplements, including kava, ephedra, skullcap and pennyroyal, have been linked to acute liver failure.

Hepatitis and other viruses. Hepatitis A, hepatitis B and hepatitis E can cause acute liver failure. Other viruses that can cause acute liver failure include Epstein-Barr virus, cytomegalovirus and herpes simplex virus.

Toxins. Toxins that can cause acute liver failure include the poisonous wild mushroom Amanita phalloides, which is sometimes mistaken for edible species.

Autoimmune disease. Liver failure can be caused by autoimmune hepatitis, a disease in which the immune system attacks liver cells, causing inflammation and injury.

Diseases of the veins in the liver. Vascular diseases, such as Budd-Chiari syndrome, can cause blockages to form in the veins of the liver and lead to acute liver failure.

Metabolic disease. Rare metabolic diseases, such as Wilson's disease and acute fatty liver of pregnancy, can cause acute liver failure.

Cancer. Cancer that begins in the liver or cancer that spreads to the liver from other locations in the body can cause acute liver failure.

Other. Other causes include idiosyncratic reactions to medication (e.g. tetracycline, troglitazone), excessive alcohol intake (severe alcoholic hepatitis), Reye syndrome (acute liver failure in a child with a viral infection e.g. chickenpox in which aspirin may play a role; and others. Many cases of acute liver failure have no apparent cause.

Acute liver failure from any cause may be prevented and/or treated by the methods and compositions of the present disclosure. The compositions may include at least one medicament or herbal supplement that is potentially harmful to the liver plus at least one OCS such as 25HC3S.

In addition, various symptoms of liver toxicity may be prevented and/or treated by the methods and compositions of the present disclosure prior to the development of full-blown ALF. Exemplary symptoms include but are not limited to: cerebral edema and encephalopathy (which may lead to hepatic encephalopathy, coma, brain herniation, etc.); coagulopathy (e.g. prolongation in prothrombin time, platelet dysfunction, thrombocytopenia, intracerebral bleeding, etc.); renal failure (e.g. due to original insult such as ATMP overdose resulting in acute tubular necrosis, or from hyperdynamic circulation leading to hepatorenal syndrome or functional renal failure); inflammation and infection (e.g. systemic inflammatory syndrome, which can lead to sepsis and multi-organ failure irrespective of the presence or absence of infection; various metabolic derangements such as hyponatremia, hypoglycemia, hypokalemia, hypophosphatemia, metabolic alkalosis, and lactic acidosis (occurring predominantly in acetaminophen overdose); hemodynamic and cardio-respiratory compromise (e.g. hypotension, decrease in tissue oxygen uptake, tissue hypoxia and lactic acidosis); pulmonary complications (e.g. acute respiratory distress syndrome (ARDS), with or without sepsis, pulmonary haemorrhage, pleural effusions, atelectasis, and intrapulmonary shunts, etc.); late pregnancy complications, for which early clinical manifestations of ALF include hypodynamia, decrease in appetite, dark amber urine, deep jaundice, nausea, vomiting, and abdominal distention, etc. Subjects exhibiting one or more of these symptoms or conditions may benefit from the administration of at least one OCS.

Acute Liver Failure Due to ATMP Toxicity

In some aspects, the present disclosure provides methods and compositions for preventing and/or treating ATMP associated toxicity and symptoms associated with or characteristic thereof, especially liver injury or ALF as discussed above. ATMP toxicity is one of the most common causes of poisoning worldwide and in the United States and the United Kingdom it is the most common cause of acute liver failure. Many individuals with ATMP toxicity may have no symptoms at all in the first 24 hours following overdose. Others may initially have nonspecific complaints such as vague abdominal pain and nausea. With progressive disease, signs of liver failure usually develop; these include low blood sugar, low blood pH, easy bleeding, and hepatic encephalopathy. Damage to the liver, or hepatotoxicity, results not from ATMP itself, but from one of its metabolites, N-acetyl-p-benzoquinoneimine (NAPQI), also known as N-acetylimidoquinone. NAPQI depletes the liver's natural antioxidant glutathione and directly damages cells in the liver, leading to liver failure. Risk factors for ATMP toxicity include excessive chronic alcohol intake, fasting or anorexia nervosa, and the use of certain drugs such as isoniazid.

Data presented herein show that administration of 25HC3S dramatically reduces mortality in subjects suffering from acetaminophen (ATMP)-induced acute liver failure. Methods to prevent or treat ALF in a subject in need thereof, especially liver dysfunction and/or acute liver failure associated with ATMP toxicity, are described in this disclosure. The methods may include administering at least one OCS (e.g. 25HC3S) prior to administration of ATMP, and/or concomitantly with administration of ATMP, and/or after administration of ATMP, to prevent and/or treat ATMP toxicity.

The disclosure also provides new compositions of matter which comprise acetaminophen co-formulated with at least one OCS, described above under "kidney dysfunction and failure". The at least one OCS is present in the composition in an amount sufficient to prevent (or at least lessen) toxicity of the acetaminophen in a subject to whom the composition is administered. The compositions include at least one substantially purified OCS, acetaminophen and one or more pharmacologically suitable carriers.

Prevention and/or Treatment of Pancreas Dysfunction and Failure

The pancreas is a glandular organ that functions in the digestive system and endocrine system of vertebrates. It produces several important hormones, including insulin, glucagon, somatostatin, and pancreatic polypeptide, and also secretes pancreatic juice containing digestive enzymes that assist digestion and absorption of nutrients in the small intestine. Inflammation of the pancreas (pancreatitis) has several causes and typically requires immediate treatment. It may be acute, beginning suddenly and lasting a few days, or chronic, occurring over many years. Eighty percent of cases of pancreatitis are caused by alcohol or gallstones, with gallstones being the single most common etiology of acute pancreatitis and alcohol being the single most common etiology of chronic pancreatitis. Severe pancreatitis is associated with organ failure, necrosis, infected necrosis, pseudocyst and abscess, having mortality rates around 2-9%, and higher where necrosis has occurred. Severe pancreatitis is diagnosed if at least three of the following are true: patient age is greater than 55 years; blood PO2 oxygen is less than 60 mm Hg or 7.9 kP; white blood cells >15,000 WBCs per microliter (mcL); calcium <2 mmol/L; urea >16 mmol/L; lactate dehydrogenase (LDH) >600 iu/L; aspartate transaminase (AST) >200 iu/L; albumin <32 g/L; and glucose >10 mmol/L.

An aspect of the present disclosure is the treatment of pancreatic dysfunction and/or failure by administering at least one OCS to a patient in need thereof. Suitable patients or patient populations are identified, by a skilled medical practitioner, as exhibiting at least one of the symptoms or criteria listed above.

Prevention and/or Treatment of Heart Dysfunction and Failure

Heart failure (HF), often used to mean chronic heart failure (CHF), occurs when the heart is unable to pump sufficiently to maintain blood flow to meet the needs of the body. The terms congestive heart failure (CHF) or congestive cardiac failure (CCF) are often used interchangeably with chronic heart failure. Symptoms commonly include shortness of breath (especially with exercise, when lying down, and at night while sleeping), excessive tiredness, and leg swelling. Common causes of heart failure include coronary artery disease including a previous myocardial infarction (heart attack), high blood pressure, atrial fibrillation, valvular heart disease, and cardiomyopathy. Heart failure is distinct from myocardial infarction, in which part of the heart muscle dies, and cardiac arrest, in which blood flow stops altogether.

Heart failure is typically diagnosed based on the history of the symptoms and a physical examination with confirmation by echocardiography, blood tests, and/or chest radiography. Echocardiography uses ultrasound to determine the stroke volume (SV, the amount of blood in the heart that exits the ventricles with each beat), the end-diastolic volume (EDV, the total amount of blood at the end of diastole), and the SV in proportion to the EDV, a value known as the ejection fraction (EF). Abnomialities in one or more of these may indicate or confirm heart dysfunction and/or failure. An electrocardiogram (ECG/EKG) is used to identify arrhythmias, ischemic heart disease, right and left ventricular hypertrophy, and presence of conduction delay or abnormalities (e.g. left bundle branch block). Abnormalities in one or more of these may also indicate or conform heart dysfunction and/or failure. Blood tests routinely performed to diagnose or confirm heart dysfunction/failure include electrolytes (sodium, potassium), measures of renal function, liver function tests, thyroid function tests, a complete blood count, and often C-reactive protein if infection is suspected. Abnormalities in one or more of these may also indicate or confirm the presence of heart dysfunction and/or failure. An elevated B-type natriuretic peptide (BNP) is a specific test indicative of heart failure. If myocardial infarction is suspected, various cardiac markers may be tested, including but not limited to troponin creatine kinase (CK)-MB (an isoform of creatine kinase); lactate dehydrogenase; aspartate transaminase (AST) (also referred to as aspartate aminotransferase); myoglobin; ischemia-modified albumin (IMA); pro-brain natriuretic peptide; glycogen phosphorylase isoenzyme BB, etc. Abnormal levels of one or more of these (usually abnormally high levels) are considered as identifying a subject in need of treatment for cardiac dysfunction or failure.

A subject who is confirmed to have or suspected of having cardiac dysfunction or failure is treated by administration of a therapeutically effective amount of at least one OCS as described herein (e.g. 25HC3S), the amount being sufficient to prevent symptoms of heart dysfunction or failure, or to ameliorate symptoms of heart dysfunction or failure, e.g. to at least partially restore heart function to normal or near normal, and/or to prevent further deterioration of heart function and health of the patient.

Prevention and/or Treatment of Brain Dysfuncion and Failure

Brain dysfunction and/or failure (i.e. organic brain syndrome "OBS") is a general term that describes decreased mental function due to a medical disease other than a psychiatric illness. Causes include but are not limited to brain injury caused by trauma; bleeding into the brain (intracerebral hemorrhage); bleeding into the space around the brain (subarachnoid hemorrhage); blood clot inside the skull causing pressure on brain (subdural hematoma); concussion; various breathing conditions such as low oxygen in the body (hypoxia) and high carbon dioxide levels in the body (hypercapnia); various cardiovascular disorders, e.g. dementia due to many strokes or multi-infarct dementia, heart infections (endocarditis, myocarditis), stroke (e.g. spontaneous stroke) and transient ischemic attack (TIA) or so-called "ministrokes"; or due to various degenerative disorders such as Alzheimer disease, Creutzfeldt-Jacob disease, diffuse Lewy Body disease, Huntington disease, multiple sclerosis, normal pressure hydrocephalus, Parkinson disease and Pick disease; dementia due to metabolic causes such as kidney, liver, or thyroid disease and/orvitamin deficiency (B1, B12, or folate); as well as drug and alcohol-related conditions e.g. alcohol withdrawal state, intoxication from drug or alcohol use, Wernicke-Korsakoff syndrome (a long-term effect of excessive alcohol consumption or malnutrition), and withdrawal from drugs (especially sedative-hypnotics and corticosteroids); and sudden onset (acute) or long-term (chronic) infections e.g. septicemia, encephalitis, meningitis, prion infections, and late-stage syphilis; as well as complications of cancer or cancer treatment. Symptoms of OBS include agitation, confusion; long-term loss of brain function (dementia), and severe, short-term loss of brain function (delirium), as well as impacts on the autonomic nervous system which controls e.g. breathing. Diagnosis or confirmation of the presence of OBS is determined by detecting or measuring various methodology such as blood tests, electroencephalogram (EEG), head CT scan, head MRI and/or lumbar puncture [for which normal values typically range as follows: pressure: 70-180 mm Hg; cerebral spinal fluid (CSF) appearance: clear, colorless; CSF total protein: 15-60 mg/100 mL; gamma globulin: 3-12% of the total protein; CSF glucose: 50-80 mg/100 mL (or greater than ⅔ of blood sugar level); CSF cell count: 0-5 white blood cells (all mononuclear), and no red blood cells; and CSF chloride: 110-125 mEq/L).

If one or more of these tests or analyses or indicia are abnormal, the subject is generally considered as susceptible to or already suffering from OBS. A subject who is confirmed to have or suspected of having OBS (either early stage or advanced) is treated by administration of a therapeutically effective amount of at least one OCS as described herein (e.g. 25HC3S), the amount being sufficient to prevent symptoms of OBS, or to ameliorate symptoms of OBS, e.g. to at least partially restore brain function to normal or near normal, and/or to prevent further deterioration of brain function and health of the patient.

Heart failure may also occur as a side effect and/or in the aftermath of chemotherapy, e.g. chemotherapy received as treatment for cancer such as breast cancer. The administration of at least one OCS as described herein to a patient receiving or who has already received chemotherapy may prevent unwanted damage to heart (and other organs, organ systems, tissues and cells) during or after cancer chemotherapy. In other words, the at least one OCS is used as a protective agent for deleterious effects of chemotherapy.

Organ Dysfunction and/or Failure Due to Trauma

In some aspects, the organ dysfunction/failure is due to trauma. Examples of trauma injuries include but are not limited to: wounds resulting from vehicular accidents; gunshot wounds (both accidental during hunting associated activities, and intentionally inflicted such as those associated with criminal activity or war); blunt trauma or blunt injury e.g. non-penetrating blunt force trauma such as physical trauma to a body part e.g. by impact, injury or physical attack; etc. Examples of blunt trauma include but are not limited to: concussion, e.g. concussion suffered by athletes or by persons involved in accidents, falls, etc., and blunt trauma suffered as the result of an encounter with a projectile such as a falling object, and others.

Individuals who are susceptible to such blunt trauma (e.g. athletes, the elderly) may benefit from prophylactic administration of one or more OCS, and if blunt trauma such as a concussion is diagnosed in a subject, the subject will benefit by administration as soon as possible after the injury is suspected or conformed.

Prevention and/or Treatment of Conditions Caused by Ischemia

Ischemia refers to an insufficient supply of blood to a tissue or organ, causing a shortage of oxygen and glucose needed for cellular metabolism and to keep tissue alive. Hypoxia (also known as hypoxiation or anoxemia) is caused by ischemia and refers to the condition in which the body or a region of the body is deprived of adequate oxygen supply. Ischemia results in tissue damage in a process known as the ischemic cascade. Damage is largely the result of the buildup of metabolic waste products, the inability to maintain cell membranes, mitochondrial damage, and eventual leakage of autolyzing proteolytic enzymes into the cell and surrounding tissues. Ensuing inflammation also damages cells and tissues. Without immediate intervention, ischemia may progress quickly to tissue necrosis, and ultimately to, for example, organ dysfunction or failure.

In addition, restoration of blood supply to ischemic tissues can cause additional damage known as reperfusion injury. Reperfusion injury can be more damaging than the initial ischemia. Reintroduction of blood flow brings oxygen back to the tissues, causing a greater production of free radicals and reactive oxygen species that damage cells. It also brings more calcium ions to the tissues, which may cause calcium overloading and can result in potentially fatal cardiac arrhythmias, and which may accelerate cellular self-destruction. The restored blood flow may also exaggerate the inflammation response of damaged tissues, causing white blood cells to destroy damaged but still viable cells.

The present disclosure provides methods of preventing and/or treating the untoward effects or outcomes of ischemia, including ischemia/reperfusion injury, in a subject in need thereof. The methods may comprise administering a therapeutically effective amount of one or more OCS sufficient to prevent or treat symptoms of ischemia and/or ischemia/reperfusion. The methods may also include identifying or diagnosing a subject who will experience, or is experiencing or who has experienced ischemia and/or ischemia/reperfusion. The ischemia and/or ischemia/reperfusion may be due to a disease process (e.g. artherosclerosis, a blood clot, etc.), or due to an accident (e.g. severing of an artery or other blood conduit), or may be intentional (planned), e.g. as occurs during some heart or other surgeries in order to temporarily stop blood flow to a defined or circumscribed region of the body.

Types of ischemia that are relevant to the methods described herein include but are not limited to:

Cardiac ischemia, e.g., myocardial ischemia, occurring when the heart muscle, or myocardium, receives insufficient blood flow. This most frequently results from atherosclerosis, which is the long-term accumulation of cholesterol-rich plaques in coronary arteries.

Bowel ischemia: Both large and small bowel can be affected by ischemic injury. Ischemic injury of the large intestine may result in an inflammatory process known as ischemic colitis and also as a result of surgery and adhesion development. Ischemia of the small bowel is called mesenteric ischemia.

Brain ischemia is insufficient blood flow to the brain, and can be acute (i.e., rapid) or chronic (i.e., long-lasting). Acute ischemic stroke is a neurologic emergency that may be reversible if treated rapidly. Chronic ischemia of the brain may result in a form of dementia called vascular dementia. A brief episode of ischemia affecting the brain is called a transient ischemic attack (TIA), often erroneously referred to as a "mini-stroke".

Limb ischemia: Lack of blood flow to a limb results in acute limb ischemia.

Cutaneous ischemia refers to reduced blood flow to the skin layers, which may result in mottling or uneven, patchy discoloration of the skin, and may lead to the development of cyanosis, or other conditions such as pressures sores (e.g. decubitus ulcers, bedsores, etc.).

Reversible ischemia refers to a condition which results in a lack of blood flow to a particular organ which can be reversed through use of medications or surgery. It most often refers to hindered blood flow to the heart muscle, but it can refer to an obstruction blocking any organ in the body, including the brain. Whether or not a case of ischemia can be reversed will depend on the underlying cause. Plaque buildup in the arteries, weakened arteries, low blood pressure, blood clots, and unusual heart rhythms can all be causes of reversible ischemia.

Apical ischemia refers to lack of blood flow to the apex or bottom tip of the heart.

Mesenteric ischemia refers to inflammation and injury of the small intestine occurs due to inadequate blood supply. Causes of the reduced blood flow can include changes in the systemic circulation (e.g. low blood pressure) or local factors such as constriction of blood vessels or a blood clot.

Ischemia of various organs, including but not limited to liver (hepatic ischemia), kidney, intestines, etc.

Ischemia, ischemia/reperfusion may also be causally related to inflammation and organ dysfunction/failure. For example, cerebral (brain) ischemia is typically accompanied by a marked inflammatory reaction that is initiated by ischemia-induced expression of cytokines, adhesion molecules, and other inflammatory mediators, including prostanoids and nitric oxide. It is known that interventions aimed at attenuating such inflammation reduce the progression of brain damage that occurs e.g. during the late stages of cerebral ischemia. In addition, the most frequent cause of intrarenal (kidney) failure (ARF) is transient or prolonged renal hypoperfusion (ischemia).

Other types of ischemia, the effects of which can be treated or prevented as described herein, include but are not limited to: ischemic stroke, small vessel ischemia, ischemia/reperfusion injuries, etc.

Diagnosis of ischemia is generally carried out by identifying one or more symptoms of malfunction in the particular organ or organ system or tissue or cell that is affected. Thus, symptoms include those listed herein for dysfunction/failure of individual organs, plus documentation of ischemia per se, such as by noting the history of the patient (e.g. known occlusion, blockage or severance of an artery that otherwise supplies blood to the organ or tissue, imaging which shows or is consistent with such observations, etc.

If one or more suitable tests or analyses or indicia are abnormal, the subject is generally considered as susceptible to or already suffering from ischemia. A subject who is confirmed to have or suspected of having ischemia (or is known to be undergoing future planned ischemia, e.g. during a surgical procedure) may be treated by administration of a therapeutically effective amount of at least one OCS as described herein (e.g. 25HC3S), the amount being sufficient to prevent symptoms of ischemia and/or ischemia-reperfusion injury, or to ameliorate symptoms of ischemia and/or ischemia-reperfusion injury, e.g. to at least partially restore organ or tissue function to normal or near normal when blood flow is reestablished, and/or to prevent further deterioration of organ or tissue function and health of the patient.

Prevention and/or Treatment of Effects of Unwanted Cell Death

Active, regulated cell death is referred to as "programmed cell-death" or "PCD" and is a regulated process mediated by intracellular pathways. While PCD is generally beneficial to an organism, aberrations in signaling or the presence of overwhelming stresses on the cell may cause undesirable PCD to occur. The forms of PCD include apoptosis, the initiation of controlled intracellular signaling in response to a stress, which brings about cell suicide; and necroptosis, a form of PCD that serves as a backup to apoptosis, e.g. when the apoptosis signaling is blocked by endogenous or exogenous factors such as viruses or mutations.

In contrast to PCD, necrosis refers to unregulated, passive cell death which results in the harmful, premature death of cells in living tissue. Necrosis is typically caused by factors external to the cell or tissue, such as infection, toxins, trauma, ischemia, etc. Without being bound by theory, it is believed that necrosis involves the loss of cell membrane integrity and an uncontrolled release of products of cell death into the intracellular space, thereby initiating an inflammatory response in the surrounding tissue which prevents nearby phagocytes from locating and eliminating the dead cells by phagocytosis. While surgical removal of necrotic tissue can halt the spread of necrosis, in some cases surgical intervention is not possible or practical e.g. when internal tissues or organs are involved. Thus, necrosis of internal organs often leads to dangerous and often deadly organ dysfunction and/or failure.

The present disclosure provides methods of preventing and/or treating the effects of unwanted cell death in a subject in need thereof, especially unwanted apoptosis and necrosis associated with organ dysfunction and/or organ failure. The cell death may result from or be associated with unwanted PCD (e.g. unwanted or deleterious apoptosis, autophagy, or necroptosis) or with necrosis, which is unwanted by definition; and/or combinations of these. The methods comprise administering a therapeutically effective amount of one or more OCS, the amount being sufficient to prevent unwanted cell death from occurring, or to treat the effects of unwanted cell death that has already occurred in a subject.

Unwanted or deleterious cell death via apoptosis occurs, for example, in the aftermath of ischemia and in Alzheimer's disease. Unwanted apoptosis is extremely harmful, causing extensive tissue damage.

Types of necrosis that may be prevented and/or treated by the methods described herein include but are not limited to:

Aseptic necrosis is necrosis without infection, usually in the head of the femur after traumatic hip dislocation.

Acute tubular necrosis refers to acute renal failure with mild to severe damage or necrosis of tubule cells, usually secondary to either nephrotoxicity, ischemia after major surgery, trauma (crush syndrome), severe hypovolemia, sepsis, or burns.

Avascular necrosis is the consequence of temporary or permanent cessation of blood flow to the bones. The absence of blood causes the bone tissue to die, resulting in fracture or collapse of the entire bone.

Balser's fatty necrosis is gangrenous pancreatitis with omental bursitis and disseminated patches of necrosis of fatty tissues.

Bridging necrosis is necrosis of the septa of confluent necrosis bridging adjacent central veins of hepatic lobules and portal triads characteristic of subacute hepatic necrosis.

Caseous or "cheesy" necrosis is necrosis in which the tissue is soft, dry, and cottage cheese-like, most often seen in tuberculosis and syphilis; in contrast to moist necrosis in which the dead tissue is wet and soft.

Central necrosis is necrosis affecting the central portion of an affected bone, cell or lobule of the liver.

Coagulation necrosis refers to necrosis of a portion of an organ or tissue, with formation of fibrous infarcts, the protoplasm of the cells becoming fixed and opaque by coagulation of the protein elements, the cellular outline persisting for a long time.

Colliquative or liquefaction necrosis is that in which the necrotic material becomes softened and liquefied.

Contraction band necrosis refers to a cardiac lesion characterized by hypercontracted myofibrils and contraction bands, and mitochondrial damage caused by calcium influx into dying cells resulting in arrest of the cells in the contracted state.

Fat necrosis is that in which the neutral fats in adipose tissue are broken down into fatty acids and glycerol, usually affecting the pancreas and peripancreatic fat in acute hemorrhagic pancreatitis.

Gangrenous necrosis is that is which ischemia combined with bacterial action causes putrefaction to set in. "Gangrene" includes dry gangrene, wet gangrene, gas gangrene, internal gangrene and necrotizing fasciitis.

Gingival necrosis refers to the death and degeneration of the cells and other structural elements of the gingivae (e.g., necrotizing ulcerative gingivitis).

Interdental necrosis is a progressive disease that destroys the tissue of the papillae and creates interdental craters. Advanced interdental necrosis leads to a loss of periodontal attachment.

Ischemic necrosis refers to death and disintegration of a tissue resulting from interference with its blood supply, thus depriving the tissues of access to substances necessary for metabolic sustenance.

Macular degeneration: Macular degeneration (both wet and dry forms) occurs when the small central portion of the retina, known as the macula, deteriorates. Because the disease develops as a person ages, it is often referred to as age-related macular degeneration (AMD).

Massive hepatic necrosis refers to massive, usually fatal, necrosis of the liver, a rare complication of viral hepatitis (fulminant hepatitis) that may also result from exposure to hepatotoxins or from drug hypersensitivity.

Phosphorus necrosis is necrosis of the jaw bone due to exposure to phosphorus.

Postpartum pituitary necrosis refers to necrosis of the pituitary during the postpartum period, often associated with shock and excessive uterine bleeding during delivery, and leading to variable patterns of hypopituitarism.

Radiation necrosis is the death of tissue caused by radiation.

Selective myocardial cell necrosis refers to myofibrillar degeneration.

Zenker's necrosis refers to hyaline degeneration and necrosis of striated muscle; also called Zenker's degeneration.

Such unwanted or pathological cell death may be prevented or treated by contacting affected cells with one or more OCSs in an amount sufficient to prevent or treat death of the cells, and or to prevent the spread of cell death signaling to adjacent cells. Candidate cells for treatment, or organs containing candidate cells for treatment, are identified by any or several known techniques, e.g. by observation of overt effects of cell death (tissue breakdown, liquification, odor, etc.), detecting release of lactate dehydrogenase (LDH), by various scans such as tomography or nuclear magnetic resonance, by detecting the presence of causative bacteria (e.g. using PCR), using antibodies, etc.

Prevention and/or Treatment of Symptoms Related to or Caused by Sepsis (Inflammatory Response Syndrome, or SIRS)

Sepsis is a potentially life-threatening whole-body inflammation caused by a serious infection which triggers an immune response. The infection is typically caused by bacteria, but can also be due to fungi, viruses, or parasites in the blood, urinary tract, lungs, skin, or other tissues. Unfortunately, symptoms can continue even after the infection is gone. Severe sepsis is sepsis causing poor organ function or insufficient blood flow as evidenced e.g. by low blood pressure, high blood lactate, and/or low urine output. In fact, sepsis is considered to fall within a continuum from infection to multiple organ dysfunction syndrome (MODS). Septic shock is low blood pressure due to sepsis that does not improve after reasonable amounts of intravenous fluids are given.

Up to now, sepsis was typically treated with intravenous fluids and antibiotics, often in an intensive care unit. Various medications and other interventions may be used, e.g. mechanical ventilation, dialysis, and oxygen saturation may also be used. Outcomes depend on the severity of disease with the risk of death from sepsis being as high as 30%, severe sepsis as high as 50%, and septic shock as high as 80%.

Provided herein are methods of preventing or treating sepsis by administering to a subject or patient in need thereof, a therapeutically effective amount of at least one OCS. For instance, the present disclosure includes the treatment of mammalian endotoxemia and septicemia and renal and mesenteric vasoconstriction that is induced by catecholamines that are used to treat endotoxemia and septic shock. The term "endotoxemia" refers to the presence of microbial endotoxins in the bloodstream. Subjects inflicted with endotoxemia usually also have septicemia. The present disclosure includes a method for treating septicemia/endotoxemia. The present disclosure also includes a method for treating acute renal failure caused by septicemia/endotoxemia. Further, the present disclosure includes a method for treating renal vasoconstriction caused by septicemia/endotoxemia. Still further, the present disclosure provides a method for attenuating catecholamine-induced renal and mesenteric vasoconstriction. Yet further, the present disclosure includes a method to prevent damage to a patient's intestines and kidney due to the effects of endotoxin and/or vasopressor agents.

Sepsis is associated with mitochondrial dysfunction, which leads to impaired oxygen consumption and may lead to sepsis-induced multiple organ failure. This holds especially true for raised tissue oxygen tensions in septic patients, suggesting reduced ability of the organs to use oxygen. Because ATP production by mitochondrial oxidative phosphorylation accounts for more than 90% of total oxygen consumption mitochondrial dysfunction may directly results in organ failure, possibly due to nitric oxide, which is known to inhibit mitochondrial respiration in vitro and is produced in excess in sepsis. Therefore, in a specific embodiment of the present disclosure, the OCS is used in methods of prevention for organ dysfunction and failure in Systemic Inflammatory Response-Syndrome (SIRS), sepsis, severe sepsis, and septic shock patients.

The methods may include identifying a suitable patient in need of such treatment, e.g. by detecting or measuring at least one symptom of sepsis, e.g. abnormal temperature (body temperature above 101 F (38.3 C, "fever") or below 96.8 F (36 C), increased heart rate, increased breathing rate, probable or confirmed infection, and possibly confusion. Patients with severe sepsis exhibit at least one of the following signs and symptoms, which indicate an organ may be failing: significantly decreased urine output, abrupt change in mental status, decrease in platelet count, difficulty breathing, abnormal heart pumping function, and abdominal pain. A diagnosis of septic shock is generally based on observing the signs and symptoms of severe sepsis plus measuring extremely low blood pressure that does not adequately respond to simple fluid replacement.

In some cases, a subject may be a candidate for prophylactic or therapeutic treatment with OCS of sepsis is based on cough/sputum/chest pain; abdominal pain/distension/diarrhea; line infection; endocarditis; dysuria; headache with neck stiffness; cellulitis/wound/joint infection; and/or positive microbiology for any infection.

In other cases, a subject may be a candidate for prophylactic or therapeutic treatment with OCS of severe sepsis based on a diagnosis of sepsis and at least one clinical suspicion of any organ dysfunction selected from: blood pressure systolic <90/mean; <65 mm HG; lactate >2 mmol/L; Bilirubine >34 µmol/L; urine output <0.5 mL/kg/h for 2 h; creatinine >177 µmol/L; platelets <100×10$^9$/L; and SpO$_2$>90% unless O$_2$ given.

In some cases, a subject may be a candidate for prophylactic or therapeutic treatment with OCS of septic shock if there is refractory hypotension that does not respond to treatment and intravenous systemic fluid administration alone is insufficient to maintain a patient's blood pressure from becoming hypotensive.

Patients with a diagnosis of (exhibiting signs of) early sepsis, severe sepsis or septic shock are candidates for treatment with the OCS described herein, e.g. by administration of a therapeutically effective amount of at least one OCS as described herein (e.g. 25HC3S). The amount administered may be sufficient to prevent symptoms of sepsis from developing or continuing, or to at least lessen the impact of symptoms of sepsis.

Prevention of Post-Harvest Damage to Harvested Organs, Tissues and Cells

Provided herein are methods, compositions and systems (e.g. apparatuses) for preserving the viability and/or preventing (protecting against) damage to and deterioration of extracorporeal cells, tissues or organs. In some aspects, the length of time for which an organ or tissue is useable for transplant may be extended, and/or organs that are otherwise not suitable for transplant may be "rescued", by contact with one or more OCS. In some aspects, the cells, tissues or organs are harvested from a donor and are ex vivo. The donor may be a living donor or a cadaver, and may be of any species, although frequently the donor is a mammal such as a human. In other aspects, the cells, tissues or organs are engineered, i.e. artificially generated by growth under controlled conditions in a laboratory. In some aspects, the organs are intended to be implanted or grafted into a transplant recipient. The recipient may be of any species, although frequently the recipient is a mammal such as a human. In some aspects, the cells, tissues and/or organs are not intended for transplant into a living donor per se but are intended for use in experimental procedures.

Application of the OCSs generally occurs after the material that is to be transplanted is removed from the body of a donor, especially if the donor is a live donor; however, if removal is from a cadaver, application may occur at any time after death of the donor is confirmed. In such cases, the OCS may be provided to several cells, tissues and/or organs at the same time within the cadaver, e.g. by artificially circulating or pumping a composition comprising the OCS through the circulatory or other system of the cadaver, or in a directed manner through one or more tissues or organs to be harvested until the material to be transplanted is harvested. If the material is artificially generated, application/contact may occur at any convenient stage of development or use of the material.

The methods generally involve contacting a harvested cell, tissue or organ with one or more OCS e.g. by applying the one or more OCS to the cell, tissue or organ, e.g. by bathing, flushing or submerging the cell, tissue or organ in or with a composition comprising the one or more OCS, and/or, in the case of tissue and organs, by perfusing the tissue or organ by pumping or circulating the composition into and through the tissue or organ. Suitable OCS for use in the composition include but are not limited to 5-cholesten-3,25-diol, 3-sulfate (25HC3S) and 5-cholesten, 3b, 25-diol, disulfate (25HCDS); (5-cholestene, 3, 27-diol, 3-sulfate); (5-cholestene, 3, 27-diol, 3, 27-disulfate); (5-cholestene, 3,7-diol, 3-sulfate); (5-cholestene, 3,7-diol, 3,7-disulfate); (5-cholestene, 3, 24-diol, 3-sulfate); (5-cholestene, 3, 24-diol, 3, 24-disulfate); and (5-cholestene, 3-ol, 24, 25-epoxy 3-sulfate).

In general, the one or more OCS are present in a suitable biologically compatible liquid carrier or solution (medium), and may be appropriate for either cold (e.g. 0-4° C.) or warm (e.g. up to about 37° C.) transport and/or storage.

The transplant medium including the at least one OCS is typically aqueous. In addition to the at least one OCS, the aqueous medium may include at least one of electrolytes, buffers, impermeants, colloids, ROS scavengers, and substrates. Examples of electrolytes include, but are not limited to, calcium, chloride, magnesium, phosphate, potassium, sodium, and sulphate. Examples of buffers include, but are not limited to, citrate, histidine, $K_2HPO_4$, $KH_2PO_4$, $Na_2HPO_4$, $NaHCO_3$, and $NaH_2PO_4$. Examples of impermeants include, but are not limited to, glucose, histidine, lactobionate, mannitol, raffinose, and sucrose. Examples colloids include, but are not limited to, hydroxyethyl starch (HES) and polyethylene glycol (PEG). Examples of ROS scavengers include, but are not limited to, allopurinol, glutathionine, mannitol, and tryptophan. Examples of substrates include, but are not limited to, adenosine, glutamate, and ketoglutarate.

In some cases, the aqueous medium includes at least one OCS and at least one of lactobionate, raffinose, HES, steroids, and insulin. In other cases, the aqueous medium includes at least one OCS and at least one of potassium lactobionate, $KH_2PO_4$, $MgSO_4$, raffinose, adenosine, glutathionine, allopurinol, and HES. In some cases, the aqueous medium includes at least one OCS and at least one of a phosphate buffer and glucose. In certain cases, the aqueous medium includes at least one OCS and at least one of phosphate buffer and sucrose. In some cases, the aqueous medium includes at least one OCS and at least one of citrate buffer, mannitol, citrate, and magnesium. In some cases, the aqueous medium includes at least one OCS and at least one of histidine buffer, mannitol, and histidine bionate. In certain cases, the aqueous medium includes at least one OCS and at least one of phosphate buffer, raffinose, and lactobionate. In some case, the aqueous medium includes at least one OCS and at least one phosphate buffer, mannitol, and lactobionate. In other cases, the aqueous medium includes at least one OCS and at least one of trehalose, gluconate, and HES. In still other cases, the aqueous medium includes potassium lactobionate, $KH_2PO_4$, $MgSO_4$, raffinose, adenosine, glutathionine, allopurinol, and PEG. In some cases, the aqueous medium includes a scavenger, such as at least one of mannitol and glutathion. In some cases, the aqueous medium includes at least one of ketoglutarate, adenosine, and glutamate.

The aqueous medium typically has a pH ranging from about 7.1 to about 7.4. The aqueous medium typically has an osmolality ranging from about 300 to about 400, such as from 310 to about 390.

Some transplant media are oxygenated (e.g. using oxygen microbubbles, see U.S. Pat. No. 7,749,692). The media may include various biologically compatible preservatives such as cryopreservatives. The media may comprise or be whole blood. Examples of suitable media include but are not limited to: Steen Solution™; Perfadex®; Histidine-tryptophan-ketoglutarate solution or Custodiol HTK™; Viaspan™; TransMedics Solutions; and those described in U.S. Pat. Nos. 8,409,846; 7,981,596; 7,977,383; 7,592,023; 7,537,885; 7,476,660; 6,365,338; and 5,306,711; or in published US patents 2014/0234827; 2013/0102059; 2011/0300237; 2010/0272789; and 2005/0164156, the complete contents of each of which are hereby incorporated by reference in their entireties. The one or more OCS are generally present in the medium at a concentration of from about 1 to about 1000 mg/liter (e.g. about 0.05 mM to about 50 mM). In a further aspect, what is provided is an in vitro composition comprising 1) one or more of: a cell or a plurality of cells; tissue or a plurality of tissues; and/or at least one organ or organ system; 2) one or more OCS; and 3) a biologically compatible medium, such as one of the above-noted aqueous media. In yet a further aspect, what is provided is a medium or composition comprising one or more OCS and a biologically compatible carrier, such as one of the above-noted aqueous media.

The compositions may be incorporated into an organ preservation and/or transport system, which includes a container for containing the cells, tissues or organs and the preservation media, and, optionally, a mechanism for circulating or pumping the medium. The system may be portable. The compositions may be incorporated into existing systems (e.g. TransMedics' proprietary Organ Care System, XVIVO's Lung Perfusion system, etc., or may be included in a newly developed system.

Exemplary organs which are treated and transported in this manner include but are not limited to kidney (single, en bloc and double kidney), heart, heart and lung together, liver (including portions thereof, right or left lobes, and lateral or other segments), lung (including single lungs, double lungs, and lung lobes), pancreas (which may include a spleen and splenic artery), stomach, etc. The organs, tissues and cells may be allografts, isografts or even xenografts (e.g. porcine heart valves used for transplant into humans). In some cases, the organ(s) which are treated and transported in this manner do not include liver. Exemplary tissues which are treated and transported in this manner include but are not limited to bones, tendons, ligaments, skin, heart valves, blood vessels, corneas, nerve tissue, etc. Exemplary cells which are treated and transported in this manner include but are not limited to stem cells, pancreatic islet cells, nerve cells, etc.

The present invention will be further illustrated by way of the following Examples. These Examples are non-limiting and do not restrict the scope of the invention. Unless stated otherwise, all percentages, parts, etc. presented in the Examples are by weight.

EXAMPLES

Examples 1A and 1B

Impact of 25HC3S Administration in Mice Subjected to a High Dose of Acetaminophen (ATMP)

Example 1A

Materials and Methods

Female mice were peritoneally-injected with acetaminophen (500 mg/kg, in 10% ethanol in PBS) either 0.5 or 2 hrs before being treated by administration of 25HC3S (20 or 25 mg/kg, 10% propylene glycol in PBS). Sera were collected 24 or 48 hrs following acetaminophen administration and enzymatic activities and other serum parameters were measured. Normal values were obtained from 10 mice who did not receive any injection, control mice received only acetaminophen (ATMP) plus vehicle, and experimental mice received ATMP plus 25HC3S.

Results

The results showed that ATMP administration significantly damaged liver tissues, increasing serum ALT activities 6-fold; and AST and LDH 20-fold. As shown in FIGS. 1A-D, treatment with 25HC3S 2 hours after ATMP administration decreased LDH by 60%; ALT by 58%; and AST by 45% within 24 hrs. In addition, treatment with 25HC3S 0.5 hours after ATMP administration returned most markers of liver and kidney function to normal levels in 48 hrs (FIG. 2), whereas untreated control values remained elevated.

Figure 3A:
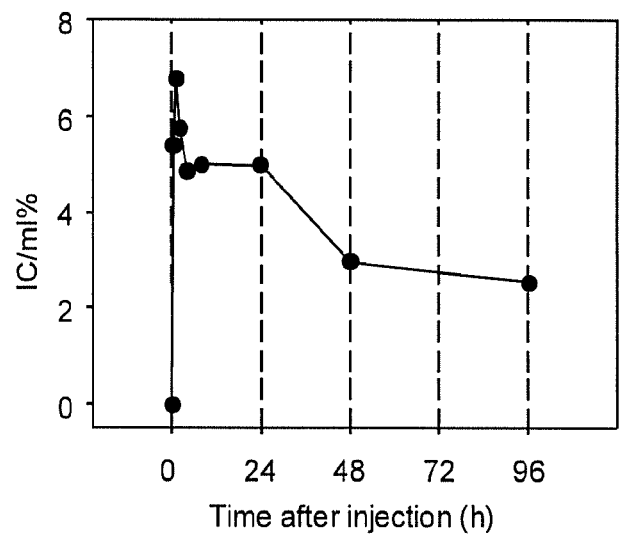
FIGS. 3A and B. Concentration of 25HC3S in A, blood and B, the indicated tissues of rats subjected to high levels of ATMP.
Figure 3B:
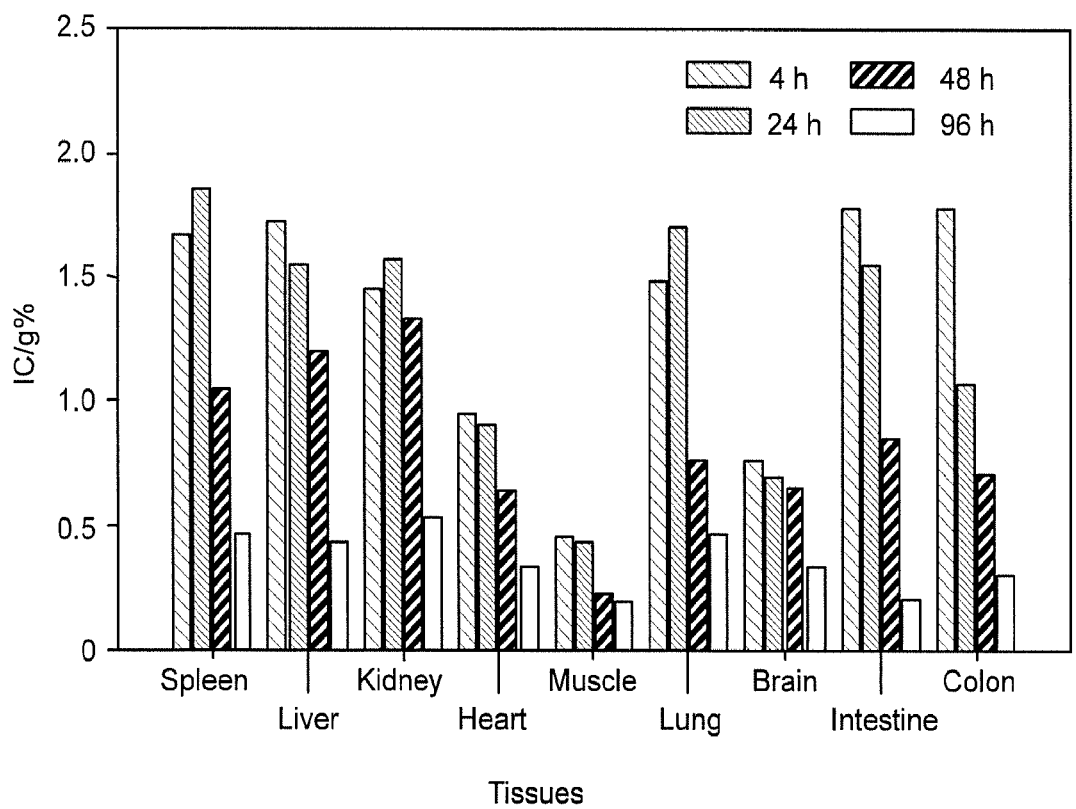

FIGS. 3A and 3B show the level of 25HC3S in blood (3A) and the indicated tissues (3B) at the indicated times after administration. As can be seen, the half life of 25HC3S in circulation is about 30 hrs, and the compound is widely distributed in different tissues in the body.

Example 1B

Materials and Methods

In another set of experiments, female mice were peritoneally-injected with acetaminophen (600 mg/kg, in 20% EtOH in PBS) and were then further treated by peritoneal injection of 25HC3S (25 mg/kg in 10% PG in PBS) 2 and 24 hrs later. Control mice received ATMP without 25HC3S. Mortality was monitored for 10 days.

Results

Figure 4:
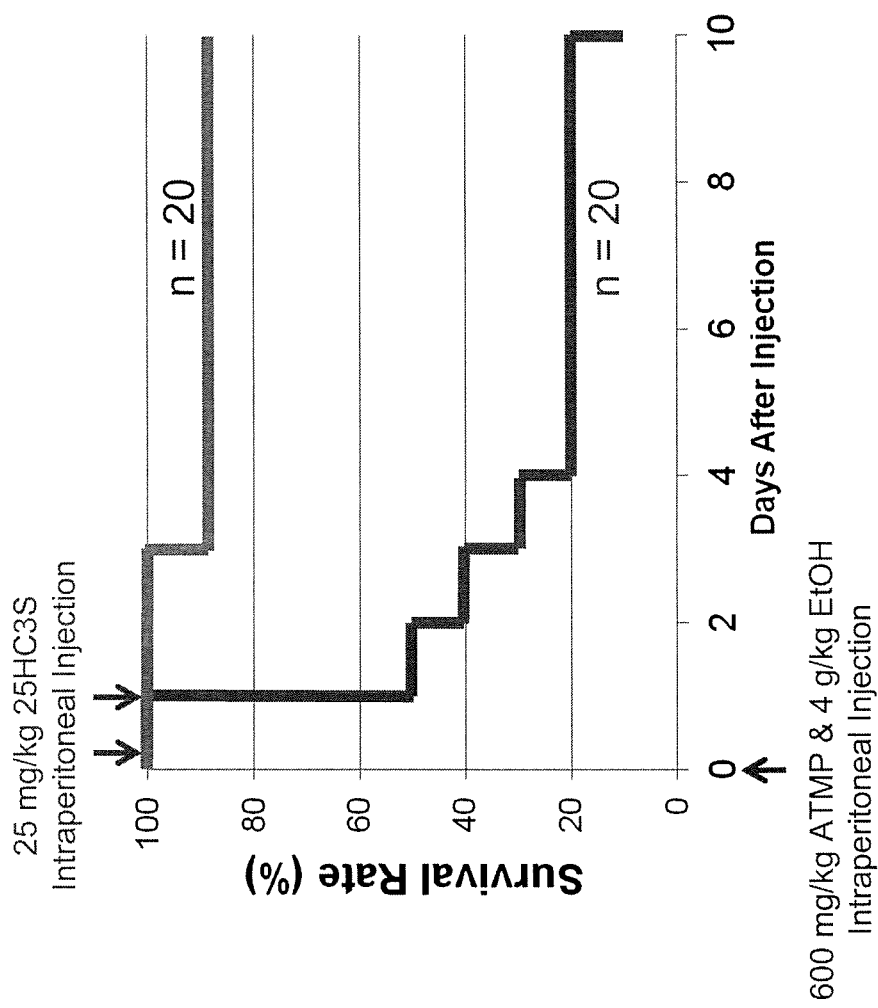
FIG. 4. Mortality data of control and 25HC3S treated rats at days 1, 2, 3, 4, and 10 days after liver ischemia.

As seen in FIG. 4, the survival rate of animals treated with 25HC3S was much higher than that of control animals, indicating that 25HC3S protected the animals from death due to high levels of ATMP.

FIGS. 5A-D show the values for the liver function (damage) markers ALT, AST, AKP and ADH for individual surviving mice. The mice are grouped as either controls who received ATMP and vehicle ("CON") or mice who received ATMP and 25HC3S. Sera were sampled at 48 hours. As can be seen, animals to whom 25HC3S was administered in general tended to have lower values of each enzyme (i.e. values nearer normal) than control animals who did not receive 25HC3S. (Note that FIG. 5 does not include data from animals that died before sampling.)

Summary of Examples 1A and 1B: Treatment with 25HC3S significantly decreased serum levels of ALT, AST, and ADH activity in mice who received ATMP, and subsequently substantially decreased the mortality of mice who received ATMP. These observations are consistent with efficacy of 25HC3S in protecting the animals from liver damage caused by high levels of ATMP, and indicate that 25HC3S can be used as biomedicine for therapy of acute liver failure induced by ATMP.

Example 2

Impact of 25HC3S on Serum Chemistry Values in Mice Subjected to a High Dose of Acetaminophen Materials and Methods.

Mice were challenged with acetaminophen (300 mg/kg PO) and then treated with vehicle or 25HC3S (25 mg/kg) by IP injection or PO gavage, one (1) hour and 24 hours after acetaminophen challenge. Measurements and samples included whole blood for serum and clinical chemistry analysis (ALT, AST, ALK, LDH, BUN and glucose) and livers and kidneys for formalin fixation and histology.

Results

Among acetaminophen-challenged groups, it was noted that groups treated with PO vehicle exhibited higher clinical chemistry values when compared with groups treated with the IP vehicle and this was also true for groups that received 25HC3S. Similarly and in general support of this, body weight loss was greater in PO-treated groups vs. IP-treated groups.

Challenge with acetaminophen resulted in body weight loss and markedly elevated clinical chemistry parameters (LDH, AST and ALT) that peaked at 24 hours post-challenge and were returning to normal at 48 hours. When 25HC3S-treated groups were compared with the appropriate administration route vehicle controls, there was no statistically significant attenuation of body weight loss or elevated clinical chemistry parameters.

In conclusion and under the conditions tested, one (1) hour post-treatment of acetaminophen challenged mice with 25HC3S (25 mg/kg, IP or PO) did not significantly alter serum chemistry values following acute liver failure, as induced by PO administration of acetaminophen at 300 mg/kg.

Example 3

Kidney Ischemia-Reperfusion

Materials and Methods
Formulation Preparation Procedure:
Preparation of the Formulation for IP Injection:

25HC3S was dissolved in propylene glycol, at 20 mg/mL, and stored at room temperature as the stock solution. Before use, 3 parts of PBS was mixed with 1 part of DV928 stock solution. The final concentration for injection was 5 mg/ml.

Preparation of the Formulation for oral gavage:

25HC3S was suspended in 0.5% carboxymethylcellulose (CMC) containing 0.05% tween-80, at 10 mg/mL, and stored at room temperature and mixed well before use.

Methods
Animals:

Adult (9- to 11-week-old) male Lewis (LEW, RE11) rats, 225-250 gram, were housed in a controlled 12-hr light-dark cycle environment and allowed free access to water and regular rat chow. All rats were anesthetized with pentobarbital 40 mg/kg i.p.

Ischemia of the left kidney was performed by transient occlusion of the left renal artery and vein, and ureter for 50 min with a vascular micro-clip. The skin was temporarily closed during the ischemia period, and the rats were put on a heating pad maintained at a temperature of 37° C. At reperfusion, the right kidney was removed before closing the abdomen with 4-0 silk suture.

Experiment Design

Animals were randomly divided into 5 groups:
Group A. 25HC3S—i.p. dosing (as pre-treatment) N=12
Group B. 25HC3S—i.p. dosing (as post-treatment) N=12
Group C. 25HC3S—oral dosing (as pre-treatment) N=12
Group D. Vehicle control, i.p. (as pre-treatment) N=6
Group E. Vehicle control, oral (as pre-treatment) N=6

Figure 11:
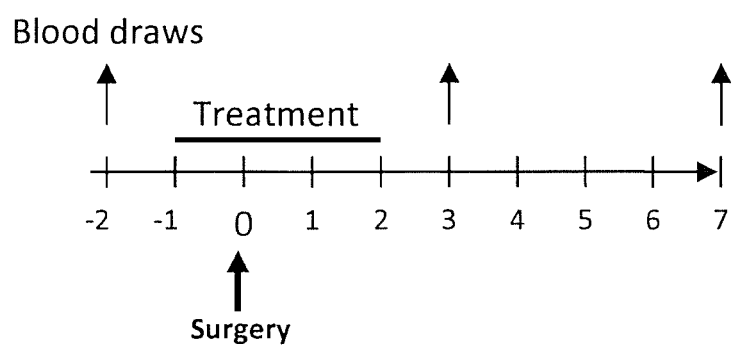
FIG. 11. Schematic representation illustrating timing (days) of blood draws, surgery, treatment and sacrifice of animals.

All animals received either active (25HC3S) or vehicle once daily for the designated period of time as indicated in FIG. 11. Rats in the pre-treatment groups received active or vehicle 1 day before (Day −1) the surgical intervention (I/R event) and continued for a total of 4 days. Rats in the post-treatment group received the 1$^{st}$ treatment at 30 min after the renal artery occlusion and continued for a total of 3 days. Blood samples were taken from all rats 2 days before the surgery (as baseline), 3 days after the surgery, and 7 days after the surgery for serum creatinine and blood urea nitrogen (BUN) analysis. All rats were sacrificed on Day 7.

Results

Figure 6A:
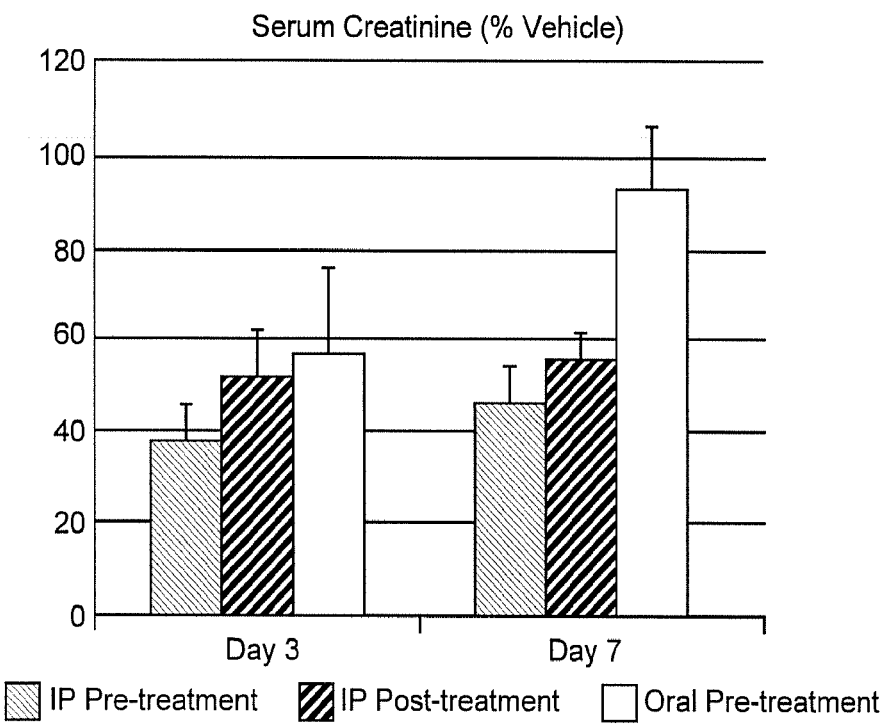
FIGS. 6A and B. Serum creatine and BUN values for renal ischemia/reperfusion experiment. A, serum creatine levels as a percentage of vehicle; B, serum BUN levels as a percentage of vehicle.
Figure 6B:
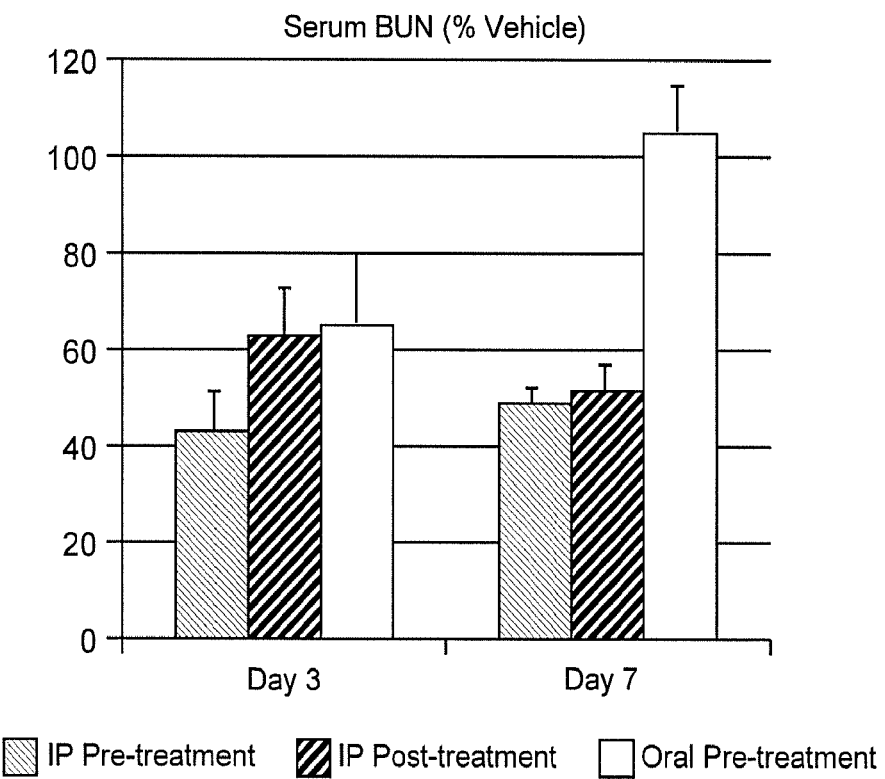

The results are presented in FIGS. 6A and B. As can be seen, pretreatment by IP injection of 25HC3S a day before the surgery significantly improved rat serum creatinine and BUN levels. Post-treatment by TP injection also reduced rat serum creatinine and BUN levels. Administration of 25HC3S by oral gavage, although given a day before the surgery and at a higher dose, reduced rat serum creatinine and BUN levels on Day 3, but to a lesser extent than administration by injection.

Example 4

Heart Ischemia-Reperfusion

Materials and Methods

Wild-type C67B16 mice, both males and females, were used in the experiment. After anesthesia, the thorax of each mouse was opened and the heart was subject to a 45-minute ischemic period by ligation of the left anterior descending coronary artery, and then reperfusion was allowed by removing the coronary arterial obstruction. The thorax was closed, and mice were allowed to recover for 24 hours. All animals were sacrificed at the end of the study, 24 h after the procedure, to gain access to the heart tissue. The heart was frozen, sectioned into slices, and then stained to determine the infarct size.

Given the experience that 25-30% of the animals may die within the 24-hour period because of the procedure (occlusion of coronary artery), all groups included 12 animals. The vehicle treated group (12 mice) was compared with 25HC3S treated groups (24 mice). One group of mice received the drug (25HC3S) just before ischemia/reperfusion (FR) and another group received drug about 16-20 h before FR. Administration was via the i.p. route with either vehicle (10% propylene glycol in PBS) or 25HC3S at a dose of 25 mg/kg in the same vehicle.

Results

Figure 7:
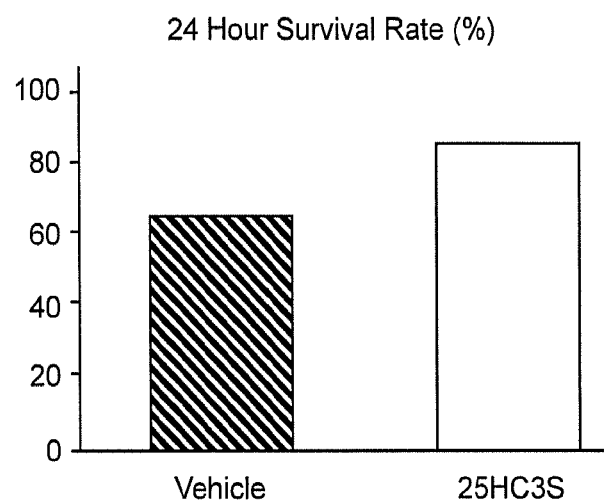
FIG. 7. 24 hour survival rates for heart ischemia/reperfusion experiment.

The data showed no statistically significant difference in sizes of infarction when comparing vehicle and drug treated mice. However, the 24-hour survival rate in the vehicle treated group was 64% vs. 86% in the 25HC3S treated group (FIG. 7), indicating that administration of 25HC3S reduces mortality after heart ischemia-reperfusion injury.

Example 5

Brain Stroke Study in Rats

Methods and Materials

Transient focal cerebral ischemia was produced by right side middle cerebral artery (MCA) occlusion in male Sprague Dawley rats under anesthesia. After 120 min of ischemia, the MCA blood flow was restored. The procedure was therefore named tMCAO. All rats were given an i.p. injection of saline (4 ml per rat) after the surgery. Three groups of rats were used in the study:
Group A: 12 sham operated rats received vehicle by ip injection
Group B: 12 tMCAO rats received vehicle by ip injection
Group C: 12 tMCAO rats received 25HC3S by ip injection The parameters measured were as follows:
Mean body weight over time
Mean 7- and 20-point Neuroscore over time
Limb Placing test results over time
Mean infarct volumes (mm3), edema volumes (mm3) and T2-relaxation times (ms)

Behavioral testing was conducted at 24 hours, 3 days, and 7 days post transient middle cerebral artery occlusion (tMCAO). Both 20-point Neuroscore and 7-point Neuroscore tests were conducted to assess post-ischemic motor and behavioral deficits. The Limb Placing test was conducted to assess the sensory motor integration of fore- and hind-limbs responses to tactile and proprioceptive stimulation.

MRI acquisitions in vivo for all rats were performed at 24 h and 7 days after tMCAO. Lesion size, tissue viability (T2 in milliseconds), and brain edema were determined using absolute T2-MRI. Eighteen (18) coronal slices of thickness 1 mm were acquired using field-of-view imaging matrix. Absolute T2-values from contra-lateral cortex were used as a reference for tissue viability. All MRI data were analyzed using Matlab software. The infarct volume/oedema analysis was done by an observer blinded to the treatment groups.

Results

The surgery of tMCAO typically introduces 20-25% mortality in animals. In this study, two animals in the treatment group died immediately after the brain surgery. One animal in the sham group, one animal in the vehicle group, and two animals in the treatment group died during the MRI measurement at 24 hour after the surgery. One animal from the vehicle group and one animal from the treatment group died 2 days or 3 days after the surgery. In addition, one animal in the vehicle group did not show any sign of tMCAO injury by all three behavioral tests, MRI measurements (criteria for exclusion), or body weight changes, indicating no surgical occlusion happened. The data from this animal was excluded from analysis. Another animal in the vehicle group also showed minimal sign of tMCAO injury by all three behavioral tests and tissue viability (T2 in ms), while no sign of injury by lesion volume and brain edema (same values as sham). Its body weight did not drop as did that of all other animals but increased after the surgery. However, the data from this animal was included in all analysis.

Figure 8A:
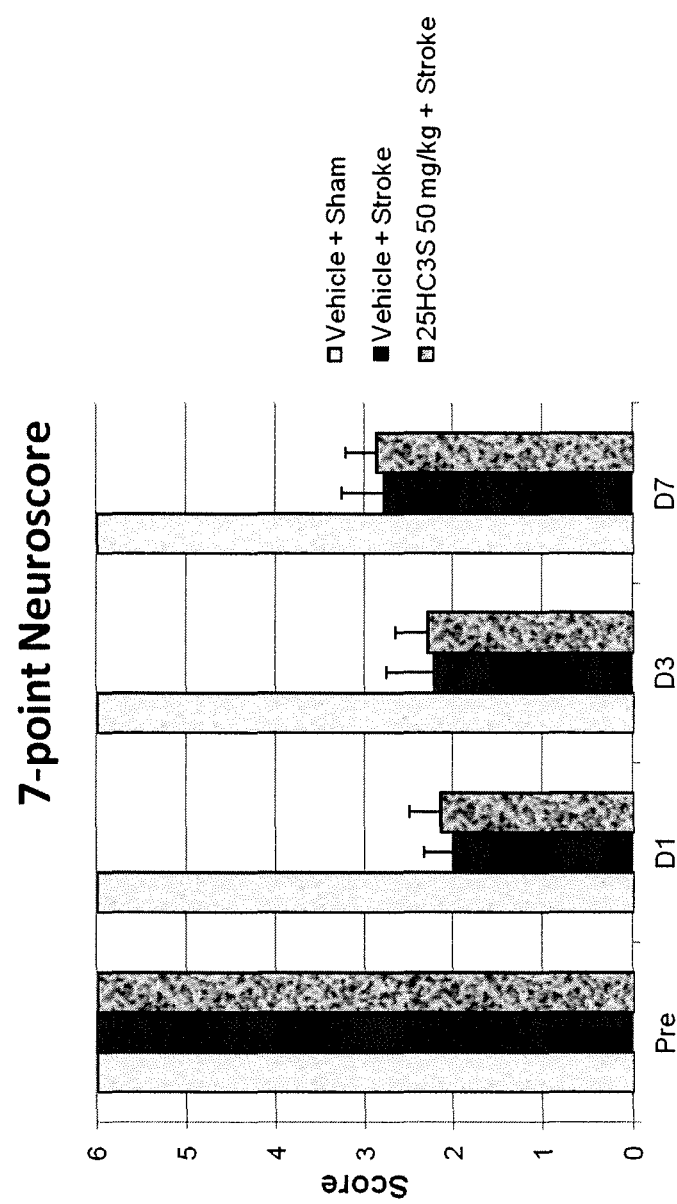
Figure 8B:
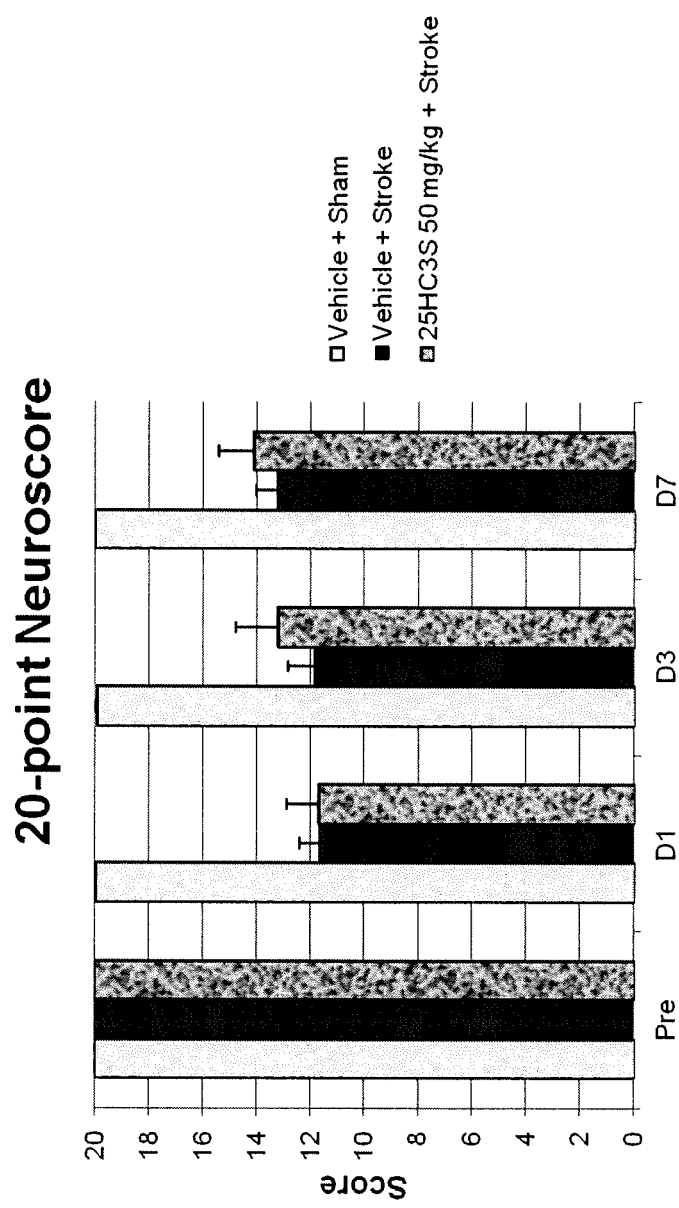
Figure 8C:
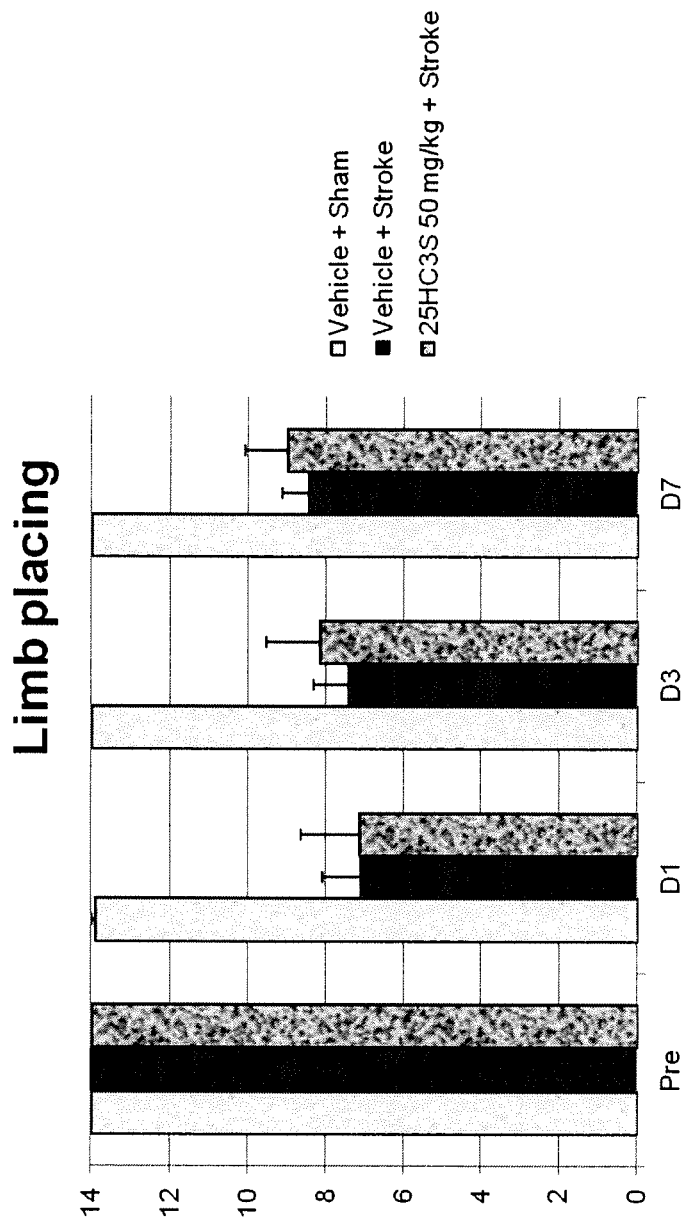

In this study, tMCAO characteristically induced both functional deficits (by behavioral tests) and brain pathology (by MRI) in all animals. Although there was a consistent trend of better scores in every test and every time point in animals receiving 25HC3S than those receiving vehicle, there were no statistically significant differences between vehicle group and treated group in 7-point Neuroscore (FIG. 8A), 20-point Neuroscore (FIG. 8B), or Limb Placing (FIG. 8C) test. A trend of recovery over time post tMCAO among all 3 behavioral tests was also noticeable in all animals. The lack of differences, if not a better trend, in treated animals relative to vehicle group in all 3 behavioral tests indicated that the treatment with 25HC3S did not cause irritation, discomfort, or any adverse side effects in these animals.

Figure 8F:
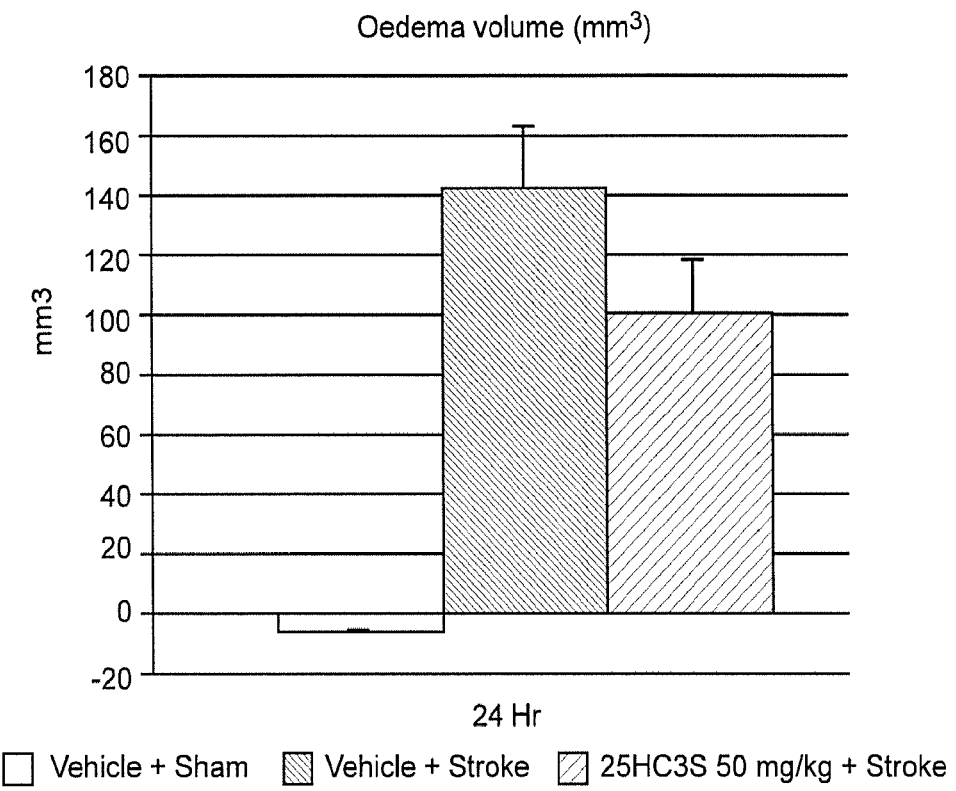
Figure 8G:
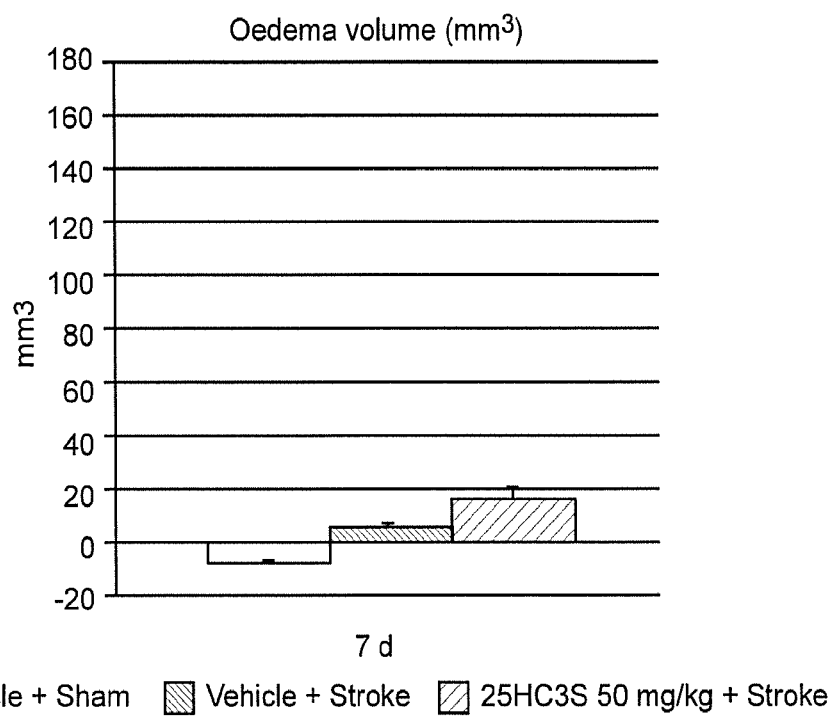
Figure 8H:
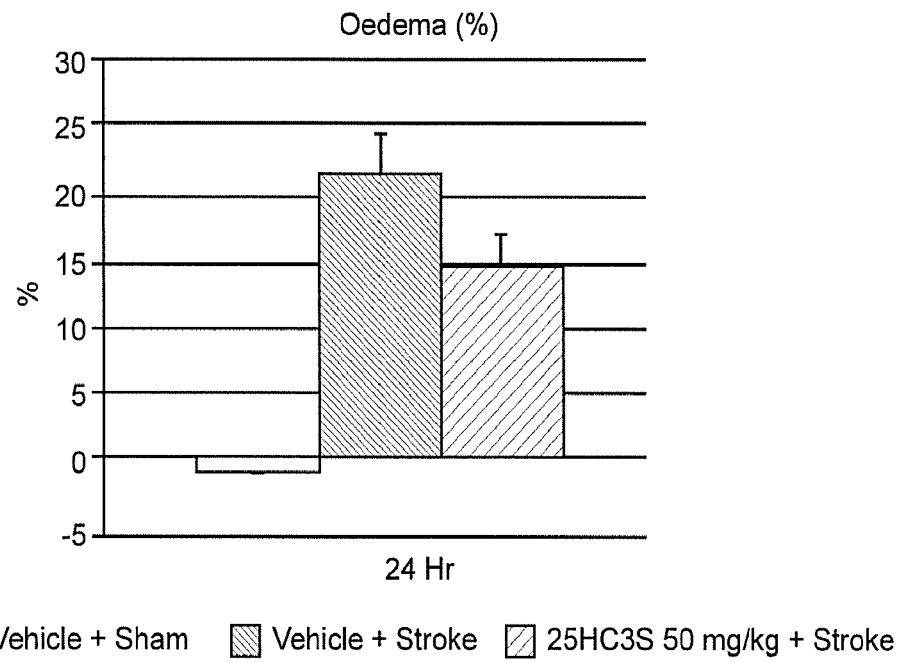
Figure 8I:
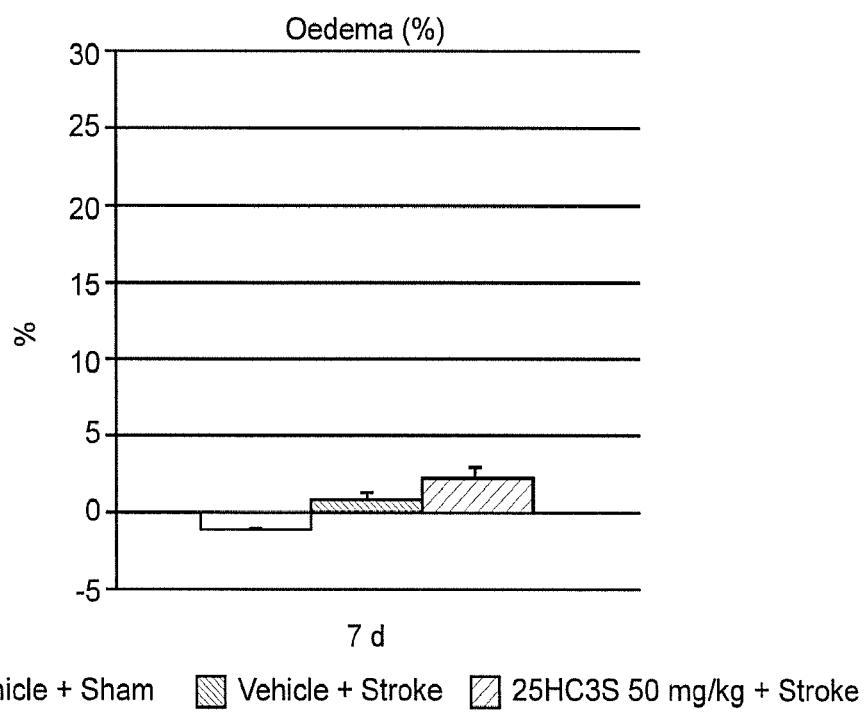

Brain edema is an acute response after ischemia/reperfusion injury, which typically peaks within 3 days after tMCAO and mostly recovers at 7 days after the procedure. In this study, all animals showed characteristic brain edema after tMCAO. Animals receiving 25HC3S showed smaller edema volume (FIG. 8F) or % edema (FIG. 8H) at 24 hours post tMCAO as compared to animals in the vehicle group, although the differences were not statistically significant. At 7 days post tMCAO, the brain edema, either edema volume or % edema, in both vehicle and treated groups were nearly recovered (FIGS. 8G and 8I).

Animals treated with 25HC3S appeared to have smaller brain lesion volumes than those receiving the vehicle at both 24 hours (FIG. 8D) and 7 days (FIG. 8E) after tMCAO, although the differences were not statistically significant.

The lesion volume tended to decrease or recover in both groups over time, comparing 24 hours with 7 days post tMCAO.

Animals treated with 25HC3S showed statistically higher tissue viability, as expressed by lower T2 relaxation time in ms, than those animals receiving the vehicle. This higher brain tissue viability (or lower T2 in ms) in treated animals than that in vehicle group was apparent at both 24 hours (FIG. 8J) and 7 days (FIG. 8K) post tMCAO. A trend of recovery was seen in both groups.

Figure 8L:
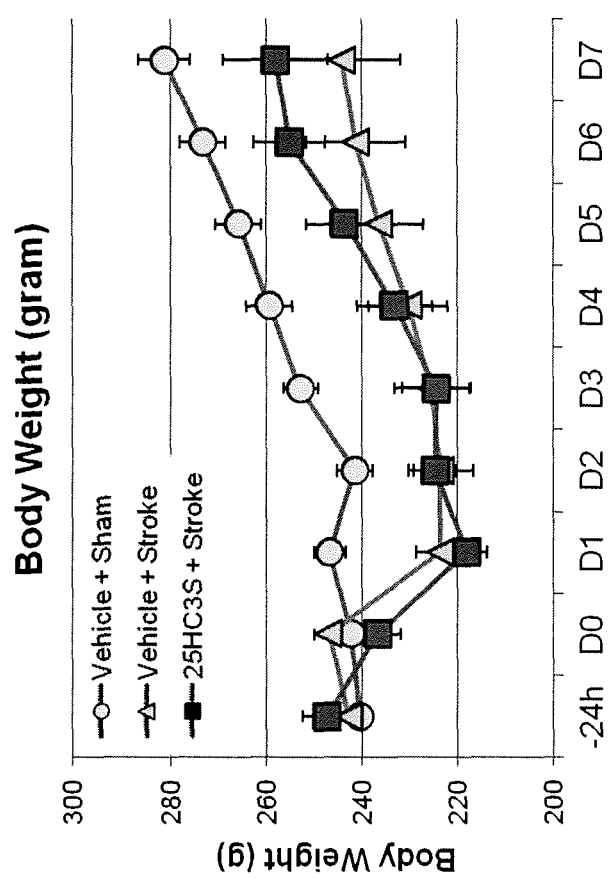

A significant but expected body weight drop was observed in all animals receiving the tMCAO procedure (FIG. 8L), although the body weights in the treatment group were decreased one day after the dosing or before the tMCAO procedure. However, consistent with other differences, regardless of statistical significance, including trends seen in brain pathology and behavioral tests, animals receiving 25HC3S showed a faster recovery in body weights than the vehicle animals receiving vehicle starting from Day 4 after the procedure.

SUMMARY

The results suggest a beneficial effect of 25HC3S in this rat tMCAO model. For instance, the MRI results indicate that 25HC3S appeared to protect the brain from acute ischemia injuries. At 24 hr after the surgery, 25HC3S treated rats showed smaller brain lesion volume and statistically significantly smaller T2 lesion. The brain edema values (both edema volume and % edema) tended to be less than those rats in the vehicle group. Although some higher levels of edema (both edema volume and % edema) were found in 25HC3S treated rats at 7 days after the surgery, the lesion volume and T2 lesion were again smaller in 25HC3S treated rats than in rats receiving vehicle. In particular, the treatment resulted in statistically significantly improved brain T2 lesion values in 25HC3S treated rats, compared to untreated rats, at both 24 hr and 7 days after the surgery.

Examples 6A-C

Sepsis

Examples 6A and 6B

Materials and Methods

To examine the effect of 25HC3S on sepsis induced by the endotoxin lipopolysaccaride (LPS), 11-week-old female C57BL/6J mice were IV-injected with LPS (30 mg/kg or 40 mg/kg, in PBS) 2 hrs before being treated by administration of 25HC3S (25 mg/kg, 10% propylene glycol in PBS), and mortality was monitored (% survival).

Results

Figure 9A:
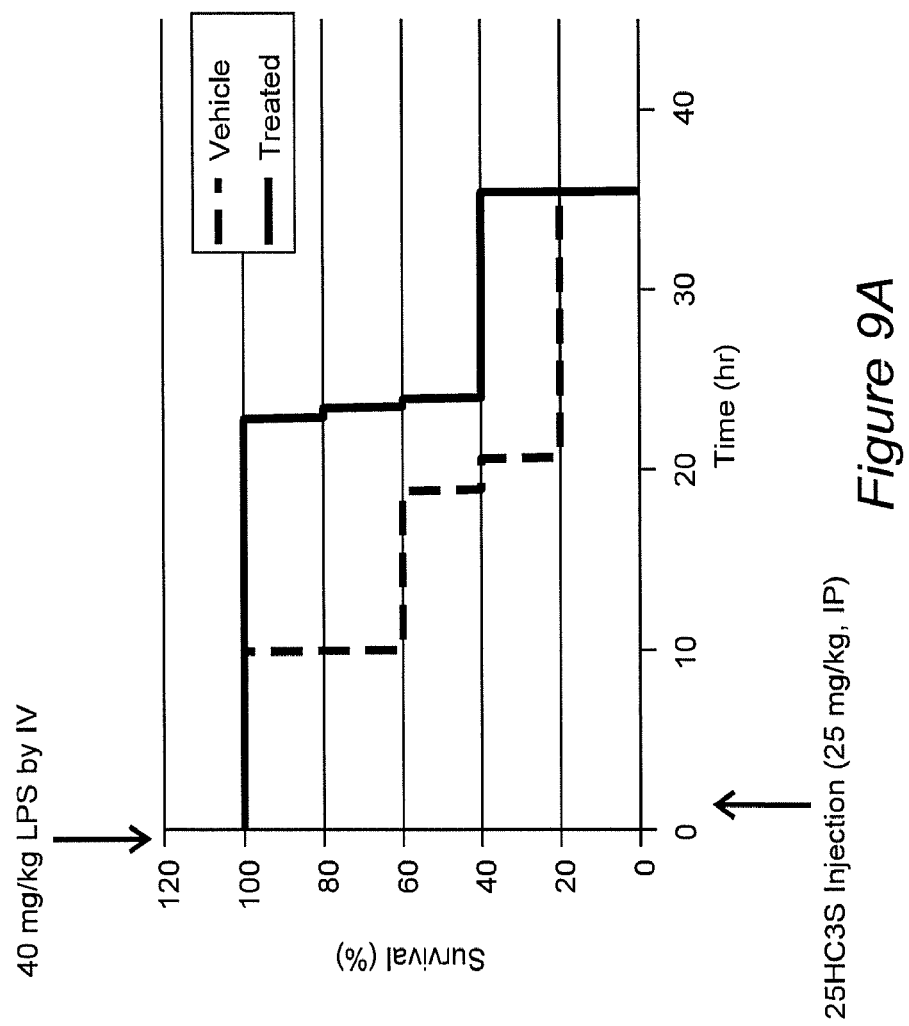
FIG. 9A-C. Sepsis studies. Mice were intravenously injected with two different concentrations of lipopolysaccharide and then with vehicle or 25 HC3S. A, 40 mg/kgLPS; B, 30 mg/kg LPS; C, 4 mg/ml LPS.
Figure 9B:
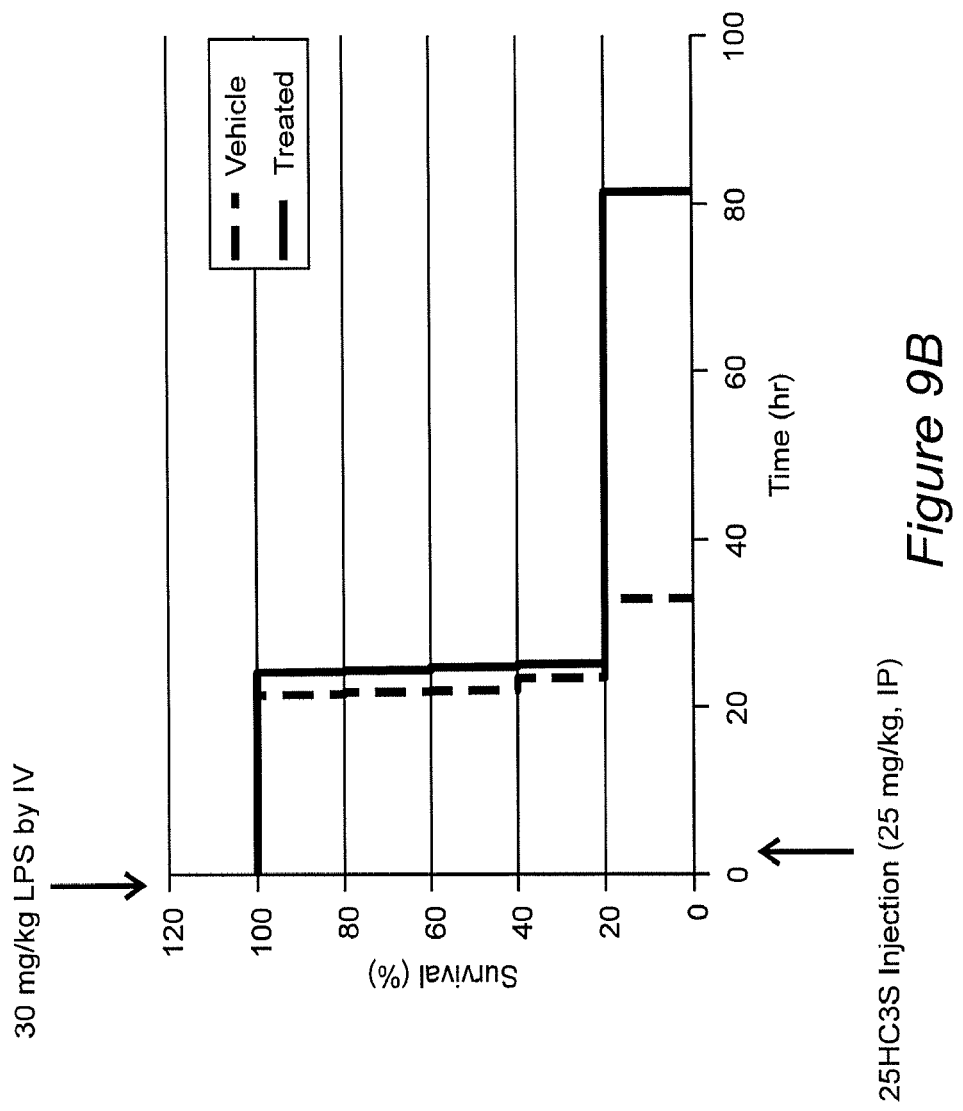

Data from these two experiments is depicted in FIGS. 9A and B. As can be seen, in both experiments, mice that received 25HC3S lived significantly longer than mice that received only vehicle.

Example 6C

Materials and Methods

Figure 9C:
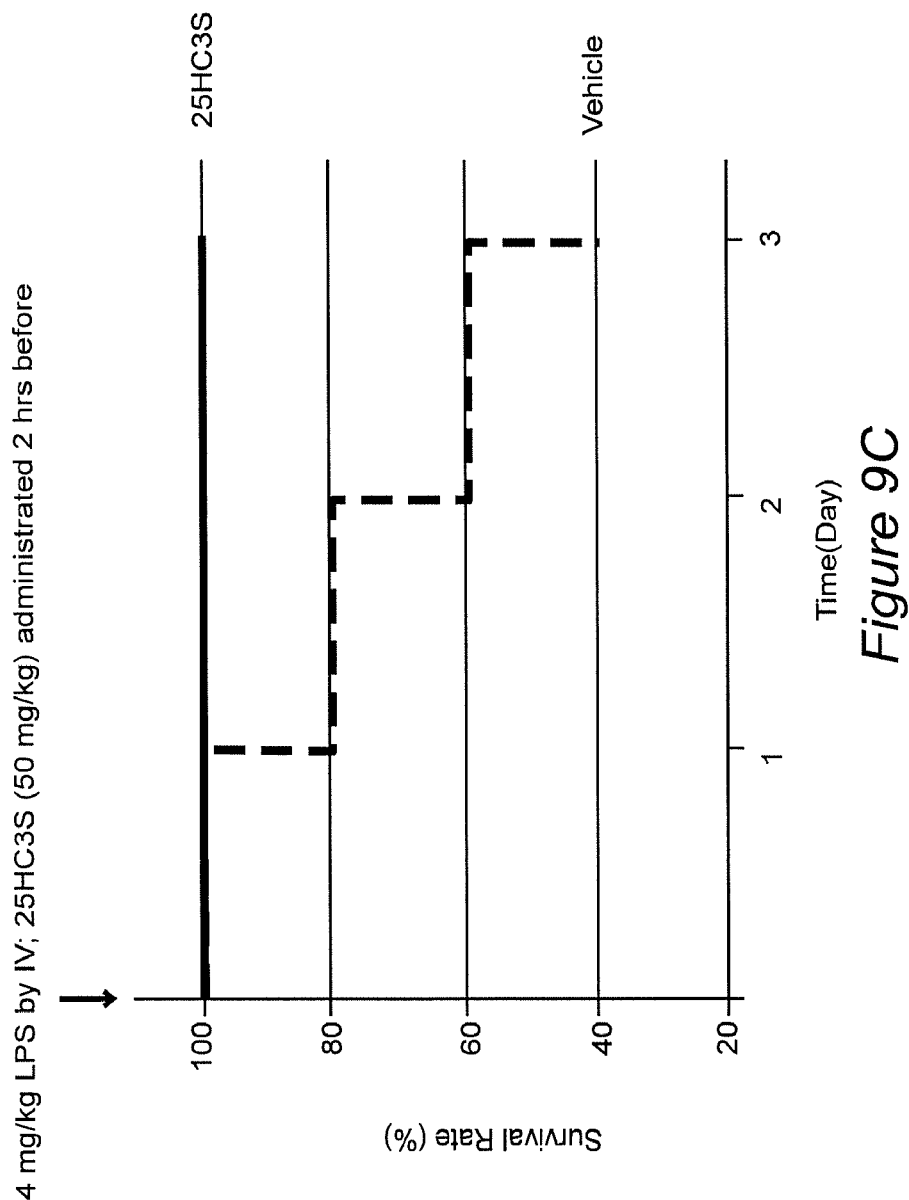

A further experiment to examine the effects of pretreatment of 25HC3S on mortality induced by LPS was conducted. In this experiment, 11-week-old female C57BL/6J mice were IV-injected with LPS (4 mg/kg in PBS). The mice were treated by administration of 25HC3S (50 mg/kg, 10% propylene glycol in PBS) 2 hrs before LPS administration, and mortality (% survival) was monitored. The results are presented below and in FIG. 9C. As can be seen:

Results

Control Group:
  At day 1, one of five (1/5) mice died, i.e. the survival rate was 80%;
  By day two, two of five (2/5) mice had died, i.e. the survival rate was 60%;
  By day 3, three of five (3/5) mice had died, i.e. the survival rate was 40%.

25HC3S treated group: As of day 3, none of the five mice treated with 25HC3S had died, i.e. the survival rate was 100%.

SUMMARY

Administration of 25HC3S prolongs life in mice exposed to LPS.

Example 7

Human Phase I Single Dose Ascending Study

Figure 10:
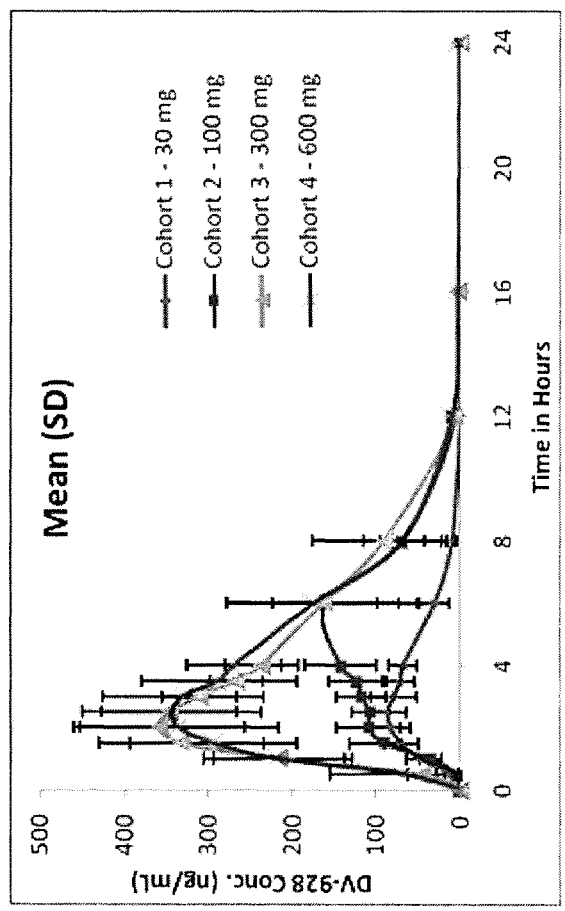
FIG. 10. Level of 25HC3S in plasma samples from Phase I cohorts 1-4.

A randomized, double blind, and placebo controlled single dose ascending First-in-human Phase 1 study was conducted. The active agent, 25HC3S, was suspended at 30, 100, 300, and 600 mg in 60 mL of ORA-Blend® SF sugar-free flavored oral suspending vehicle. As Placebo dosage form, calcium carbonate, USP, was suspended at 30, 100, 300, and 600 mg in 60 mL of ORA-Blend® SF sugar-free flavored oral suspending vehicle. The suspension, either active or Placebo, was orally administered to each subject. Each dose group had 4 subjects receiving a single dose of active and 2 subjects receiving a single dose of Placebo. All subjects were monitored by health professionals for any potential adverse events for 7 days following administration. Plasma samples were collected at selected time intervals before and after the administration, as indicated in FIG. 10.

No adverse effects were observed in any dose group, including those who received 600 mg of 25HC3S. Both active and placebo were well tolerated. Phainiacokinetically, the drug exhibited high bioavailability (FIG. 10).

Unless otherwise stated, a reference to a compound or component includes the compound or component by itself, as well as in combination with other compounds or components, such as mixtures of compounds.

As used herein, the singular forms "a," "an," and "the" include the plural reference unless the context clearly dictates otherwise.

For all numeric ranges provided herein, it should be understood that the ranges include all integers between the highest and lowest value of the range, as well as all decimal fractions lying between those values, e.g. in increments of 0.1.

For all numeric values provided herein, the value is intended to encompass all statistically significant values surrounding the numeric value.

While the invention has been described in terms of its preferred embodiments, those skilled in the art will recognize that the invention can be practiced with modification within the spirit and scope of the appended aspects and claims. Accordingly, the present invention should not be limited to the embodiments as described above, but should further include all modifications and equivalents thereof within the spirit and scope of the description provided herein.

The invention claimed is:

1. A method of treating acute liver dysfunction or acute liver failure in a human subject in need thereof, comprising administering to the human subject an amount of a sodium salt of 5-cholesten-3,25-diol, 3-sulfate (25HC3S) that is sufficient to treat the acute liver dysfunction or acute liver failure, wherein the acute liver dysfunction or acute liver failure comprises alcoholic hepatitis.

2. The method of claim 1, wherein the alcoholic hepatitis is characterized by reduced liver function that occurs within 13 weeks of onset.

3. The method of claim 1, wherein the alcoholic hepatitis is characterized by reduced liver function that occurs within 10 weeks of onset.

4. The method of claim 1, wherein the alcoholic hepatitis is characterized by loss of liver function that occurs within 13 weeks of onset.

5. The method of claim 1, wherein the alcoholic hepatitis is characterized by loss of liver function that occurs within 10 weeks of onset.

6. The method of claim 1, wherein the administering is performed by at least one of orally, subcutaneously, and intramuscularly.

7. The method of claim 1, wherein the administering is performed intravenously.

8. The method of claim 1, wherein the administering comprises injection.

9. The method of claim 1, wherein the sodium salt of 25HC3S is administered in a formulation further comprising a pharmaceutically acceptable carrier.

10. The method of claim 1, wherein the sodium salt of 25HC3S is administered at a dose ranging from about 0.001 mg/kg to about 100 mg/kg.

11. The method of claim 1, wherein the sodium salt of 25HC3S is administered at a dose ranging from about 0.001 mg/kg to about 10 mg/kg.

12. The method of claim 1, wherein the sodium salt of 25HC3S is administered at a dose ranging from about 0.1 mg/kg to about 10 mg/kg.

13. The method of claim 1, wherein the administering is performed from once to 3 times per day.

14. The method of claim 2, wherein the sodium salt of 25HC3S is administered at a dose ranging from about 0.001 mg/kg to about 10 mg/kg.

15. The method of claim 3, wherein the sodium salt of 25HC3S is administered at a dose ranging from about 0.001 mg/kg to about 10 mg/kg.

16. The method of claim 4, wherein the sodium salt of 25HC3S is administered at a dose ranging from about 0.001 mg/kg to about 10 mg/kg.

17. The method of claim 5, wherein the sodium salt of 25HC3S is administered at a dose ranging from about 0.001 mg/kg to about 10 mg/kg.

18. The method of claim 7, wherein the sodium salt of 25HC3S is administered at a dose ranging from about 0.001 mg/kg to about 10 mg/kg.

19. The method of claim 8, wherein the sodium salt of 25HC3S is administered at a dose ranging from about 0.001 mg/kg to about 10 mg/kg.

20. The method of claim 9, wherein the sodium salt of 25HC3S is administered at a dose ranging from about 0.001 mg/kg to about 10 mg/kg.

21. The method of claim 1, wherein the human subject has jaundice prior to treatment.

* * * * *

UNITED STATES PATENT AND TRADEMARK OFFICE
CERTIFICATE OF CORRECTION

| | |
|---|---|
| PATENT NO. | : 11,612,609 B2 |
| APPLICATION NO. | : 16/983492 |
| DATED | : March 28, 2023 |
| INVENTOR(S) | : Shunlin Ren et al. |

It is certified that error appears in the above-identified patent and that said Letters Patent is hereby corrected as shown below:

In the Specification

At Column 1, in the paragraph at Line 18, please insert the Government Support Clause so the paragraph reads:
-- GOVERNMENT RIGHTS
This invention was made with government support under a Veteran's Administration Merit Review Research Career Scientist Award. The government has certain rights in the invention. --

Signed and Sealed this
Twenty-seventh Day of June, 2023

Katherine Kelly Vidal
*Director of the United States Patent and Trademark Office*